(12) United States Patent
Arora et al.

(10) Patent No.: US 7,435,731 B2
(45) Date of Patent: *Oct. 14, 2008

(54) SUBSTITUTED PYRAZOLO[3,4-D]PYRIMADINES AND METHODS OF USING THE SAME

(75) Inventors: Nidhi Arora, Cupertino, CA (US); Roland Joseph Billedeau, Santa Clara, CA (US); Nolan James Dewdney, San Jose, CA (US); Tobias Gabriel, San Francisco, CA (US); David Michael Goldstein, San Jose, CA (US); Counde O'Yang, Sunnyvale, CA (US); Michael Soth, Milpitas, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 240 days.

This patent is subject to a terminal disclaimer.

(21) Appl. No.: 11/067,336

(22) Filed: Feb. 25, 2005

(65) Prior Publication Data

US 2005/0197340 A1    Sep. 8, 2005

Related U.S. Application Data

(60) Provisional application No. 60/548,583, filed on Feb. 27, 2004.

(51) Int. Cl.
*C07D 487/04* (2006.01)
*C07D 413/04* (2006.01)
*C07D 413/12* (2006.01)
*A61K 31/519* (2006.01)
*A61K 31/541* (2006.01)
*A61K 31/5355* (2006.01)
*C07D 471/04* (2006.01)
*A61K 31/437* (2006.01)
*A61P 19/02* (2006.01)
*A61P 11/16* (2006.01)

(52) U.S. Cl. .............. 514/222.2; 514/262.1; 514/234.2; 514/303; 514/249; 544/262; 544/118; 544/3; 544/350; 546/119

(58) Field of Classification Search ................. 544/262, 544/118; 514/262.1, 234.2
See application file for complete search history.

(56) References Cited

U.S. PATENT DOCUMENTS

| 3,821,382 | A | * | 6/1974 | Hoyle et al. | ............. | 514/262.1 |
| 4,020,072 | A | | 4/1977 | Hoehn | | |
| 2003/0207900 | A1 | | 11/2003 | Chen et al. | | |
| 2004/0176325 | A1 | | 9/2004 | Munson et al. | | |
| 2004/0180896 | A1 | | 9/2004 | Munson et al. | | |
| 2005/0277655 | A1 | * | 12/2005 | Ding et al. | ............... | 514/262.1 |

FOREIGN PATENT DOCUMENTS

| DE | 2052719 A1 | 9/1971 |
|---|---|---|
| EP | 0 104 522 B1 | 5/1991 |
| EP | 1 148 054 A1 | 10/2001 |
| WO | WO 98/09961 A1 | 3/1998 |
| WO | WO 99/23077 A1 | 5/1999 |
| WO | WO 00/27627 A1 | 5/2000 |
| WO | WO 01/98301 A1 | 12/2001 |
| WO | WO 02/22586 A1 | 3/2002 |
| WO | WO 02/051837 A2 | 7/2002 |
| WO | WO 02/059088 A1 | 8/2002 |
| WO | WO 03/000187 A2 | 1/2003 |
| WO | WO 03/009852 A1 | 2/2003 |
| WO | WO 03/029209 A2 | 4/2003 |
| WO | WO 03/062392 A2 | 7/2003 |
| WO | WO 03/068754 A1 | 8/2003 |
| WO | WO 03/099820 A1 | 12/2003 |
| WO | WO 2005085248 | * 9/2005 |

OTHER PUBLICATIONS

Fijen (Clinical & Experimental Immunology, 2001, 124, 16-20).*
Gong et. al. (Chinese Chemical Letters, 2002, 13(7), 613-616).*

(Continued)

*Primary Examiner*—Brenda Coleman
*Assistant Examiner*—Susanna Moore
(74) *Attorney, Agent, or Firm*—Robert C. Hall

(57) ABSTRACT

Compounds of the formula Ia or Ib:

wherein A, B, X, Y, Z, W, k, $R^1$, $R^2$, $R^3$, $R^4$ and $R^5$ are those defined herein, and compositions comprising the same. The present invention also provides methods for preparing compounds of formula I and using the same in treating p38 mediated disorders in a subject.

16 Claims, No Drawings

OTHER PUBLICATIONS

Hashimoto (J Pharmacol Exp Ther., 2000, 293(2), 370-375).*
Esper et. al. (Expert. Opin. Investig. Drugs, 2005, 14(5), 633-645).*
Jones et al, "British Society of Gastroenterology guidelines for the management of the irritable bowel syndrome." Gut 2000, (Suppl II)47:ii1-ii19.*
Fijen (Clinical & Experimental Immunology, 2001, 124, 16-20).*
Gong et. al. (Chinese Chemical Letters, 2002, 13(7), 613-616).*
Hashimoto (J Pharmacol Exp Ther., 2000, 293(2), 370-375).*
Esper et. al. (Expert. Opin. Investig. Drugs, 2005, 14(5), 633-645).*
Badger, A. M., et al. "Pharmacological Profile of SB 203580, a Selective Inhibitor of Cytokine Suppressive Binding Protein/p38 Kinase, in Animal Models of Arthritis, Bone Resorption, Endotoxin shock and Immune Function," *J. Pharm. Exp. Therap.* (1996) vol. 279 (1) pp. 1453-1461.
Badger, A. M., et al, "SB 203580 Inhibitors p38 Mitogen-Activated Protein Kinase, Nitric Oxide Production, and Inducible Nitric Oxide Synthase in Bovine Cartilage-Derived Chondrocytes," *J. Immunol.* (1998) vol. 161, pp. 467-473.
Badger, A. M., et al. "Disease-Modifying Activity of SB242235, A Selective Inhibitor of p38 Mitogen-Activated Protein Kinase, in Rat Adjuvant-induced Arthritis," *Arthritis & Rheumatism* (2000) vol. 43, (1) pp. 175-183.

Jackson, J.R. et al., "Pharmacological Effects of SB 220025, a Selective Inhibitor of P38 Mitogen-Activated Protein Kinase, in Angiogenesis and Chronic Inflammatory Disease Models," *J. Pharma. Exp. Therap.* (1998) vol. 284, (2) pp. 687-692.
Parasrampuria, D. A., et al., "Single-Dose Pharmocokinetics and Pharmacodynamics of RWJ 67657, a Specific p38 Mitogen-Activated Protein Kinase Inhibitors: A First-in-Human Study," *J. Clin. Pharmacol.* (2003) vol. 43, pp. 406-413.
Pargellis, C. et al., "Inhibitors of p38 Mitogen-Activated Protein Kinase for the Treatment of Rheumatoid Arthritis," *Current Opin. Investigational Drugs* (2003) vol. 4 (5) pp. 566-571.
Studer, R. K., et al., "Chrondrocyte Response to Growth Factors is Modulated by p38 Mitogen-Activated protein Kinase Inhibitors," *Arthritis Research Ther.* (2004) vol. 6, pp. R56-64.
Wada, Y., et al., "R-130823, a Novel Inhibitor of p38 MAPK, Ameliorates Hyperalgesia and Swelling in Arthritis Models," *Europ. J. Pharmacol.* (2005) vol. 506, pp. 285-295.
Wadsworth, S. A., et al., "RWJ 67657, a Potent, Orally Active Inhibitor of p38 Mitogen-Activated Protein Kinase," *J. Pharm. Exp. Therapeutics* (1999) vol. 291 (2) pp. 680-687.

* cited by examiner

SUBSTITUTED PYRAZOLO[3,4-D]PYRIMADINES AND METHODS OF USING THE SAME

CROSS REFERENCE TO RELATED APPLICATIONS

This application claims benefit under 35 U.S.C. 119(e) of U.S. Provisional Application No. 60/548,583 filed Feb. 27, 2004, which is hereby incorporated by reference in its entirety.

FIELD OF THE INVENTION

The present invention relates to azaindazoles, derivatives thereof, a process for their manufacture, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group that includes various isoforms (e.g., p38α, p39β, p38γ and p38δ). The p38 kinases are responsible for phosphorylating and activating transcription factors as well as other kinases, and are activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

Additionally, the involvement of p38 has been implicated in stroke, Alzheimer's disease, osteoarthritis, lung injury, septic shock, angiogenesis, dermatitis, psoriasis and atopic dermatitis. *J. Exp. Opin. Ther. Patents,* 2000, 10(1).

The inhibition of these cytokines by inhibition of the p38 kinase is of benefit in controlling, reducing and alleviating many of these disease states.

SUMMARY

The invention provides compounds of formula Ia or 1b:

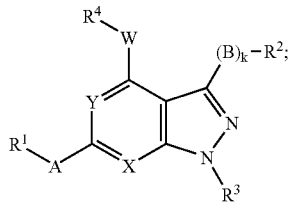

Ia

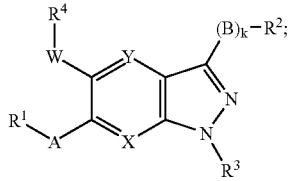

Ib

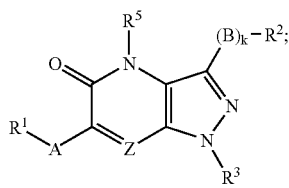

Ic or a pharmaceutically acceptable salt thereof,
wherein:
  $R^1$ is aryl, heteroaryl, aralkyl or cycloalkyl;
  $R^2$ is aryl, heteroaryl, cycloalkyl, branched alkyl or heterocyclyl;
  $R^3$ is hydrogen or alkyl;
  $R^4$ is hydrogen, alkyl, hydroxy, amino, heteroalkyl, heterocyclyl, heterocyclylalkyl, hydroxycycloalkyl, cycloalkylalkyl, alkylsulfonyl, alkylsulfonamido, aryl, heteroaryl, aralkyl, heteroaralkyl, —(CHR$^a$)$_r$—C(=O)—R$^b$, —(CHR$^a$)$_r$—O—C(=O)—R$^b$, —(CHR$^a$)$_r$—NH—C(=O)—R$^b$ or —SO$_2$—R$^b$,
  wherein
    $R^a$ is hydrogen, alkyl or heteroalkyl;
    $R^b$ is alkyl, hydroxy, amino, heteroalkyl, aryl, aralkyl, heteroaryl, or heterocyclyl;
    r is from 0 to 4;
  $R^5$ is hydrogen, alkyl, heteroalkyl, aralkyl, heteroaralkyl, heterocyclyl, hydroxycycloalkyl, —C(=O)—R$^c$ or —SO$_2$—R$^c$,
  wherein
    $R^c$ is alkyl, heteroalkyl, aryl, aralkyl, heteroaryl or heterocyclyl;
  X and Y are nitrogen, or one of X and Y is nitrogen and the other is CR$^d$;
  Z is N or CR$^d$,
  wherein
    $R^d$ is hydrogen, alkyl, hydroxy, alkoxy, amino, haloalkyl, cyano, halo, heteroalkyl, C(=O)—R$^e$ or —SO$_2$—R$^e$,
  wherein
    $R^e$ is hydrogen or alkyl;
  W is O, S(O)$_m$, CH$_2$ or NR$^f$,
  wherein
    m is from 0 to 2, and
    $R^f$ is hydrogen, alkyl, heteroalkyl, heterocyclyl, hydroxycycloalkyl, —C(=O)—R$^g$ or —SO$_2$—R$^g$,
  wherein
    $R^g$ is alkyl, aryl, aralkyl, heteroaryl, heteroalkyl or heterocyclyl;

or $R^4$ and $R^f$ together with the atoms to which they are attached may form a heterocyclic ring;

A is O, $CH_2$, $S(O)_m$, $C(=O)$, $NR^h$, or $CH(OR^h)$,
wherein
m is from 0 to 2, and
$R^h$ is hydrogen or alkyl,
or $R^1$ and $R^h$ may form a heterocyclyl;
k is 0 or 1;
B is O, $S(O)_j$, $CH(OR^i)$, $NR^j$, or or $C(=O)$,
wherein
j is 0, 1 or 2;
$R^i$ is hydrogen or alkyl,
$R^j$ is hydrogen, alkyl, $-C(=O)-R^k$, or $-SO_2R^m$,
wherein
$R^k$ is alkyl, aryl or aralkyl; and
$R^m$ is alkyl.

Another aspect of the invention provides a pharmaceutical formulation comprising one or more compounds of formula I and a pharmaceutically acceptable carrier, diluent, and/or excipient therefor.

Compounds of the invention are inhibitors of protein kinases, and exhibit effective activity against p38 in vivo. They are selective for p38 kinase relative to cyclin-dependent kinases and tyrosine kinases. Therefore, compounds of the present invention can be used for the treatment of diseases mediated by the pro-inflammatory cytokines such as TNF and IL-1. Thus, another aspect of the present invention provides a method for treating p38 mediated diseases or conditions in which a therapeutically effective amount of one or more compounds of formula I is administered to a patient.

DETAILED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means a linear saturated monovalent hydrocarbon moiety of one to six carbon atoms or a branched saturated monovalent hydrocarbon moiety of three to six carbon atoms, e.g., methyl, ethyl, propyl, 2-propyl, n-butyl, iso-butyl, tert-butyl, pentyl, and the like.

"Alkylene" means a linear saturated divalent hydrocarbon moiety of one to six carbon atoms or a branched saturated divalent hydrocarbon moiety of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylsulfonylalkyl" means a moiety of the formula $R^a$—$SO_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Alkylamino means a moiety of the formula —NR—R' wherein R is hyrdogen or alkyl and R' is alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Alkylsulfonyl" means a moiety of the formula —$SO_2$R wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein. "Alkylsulfonylamido" means a moiety of the formula —NR'$SO_2$—R wherein R is alkyl and R' is hydrogen or alkyl.

"Amino" means a radical —NR'R, where R' and R each independently is hydrogen or alkyl.

"Aryl" means a monovalent monocyclic or bicyclic aromatic hydrocarbon moiety which is optionally substituted with one or more, preferably one, two or three, substituents, each of which is preferably selected from the group consisting of alkyl, hydroxy, alkoxy, haloalkyl, haloalkoxy, halo, nitro, cyano, amino, mono- and dialkylamino, methylenedioxy, ethylenedioxy, acyl, heteroalkyl, optionally substituted aryl, optionally substituted heteroaryl, optionally substituted aralkyl, and optionally substituted heteroaralkyl. A particularly preferred aryl substituent is halide. More specifically the term aryl includes, but is not limited to, phenyl, 1-naphthyl, 2-naphthyl, and the like, each of which can be substituted or unsubstituted.

"Aralkyl" refers to a moiety of the formula $Ar^a$—$R^z$—, where $Ar^a$ is optionally substituted aryl and $R^z$ is alkylene as defined herein.

"Substituted aralkyl" or "optionally substituted aralkyl" refers to aralkyl in which the aryl moiety is substituted or optionally substituted, respectively.

"Cycloalkyl" refers to a saturated monovalent cyclic hydrocarbon moiety of three to seven ring carbons e.g., cyclopropyl, cyclobutyl, cyclohexyl, 4-methyl-cyclohexyl, and the like. Cycloalkyl may optionally be substituted with one or more substituents, preferably one, two or three, substituents. Preferably, cycloalkyl substituent is selected from the group consisting of alkyl, hydroxy, alkoxy, haloalkyl, haloalkoxy, halo, amino, mono- and dialkylamino, heteroalkyl, acyl, aryl and heteroaryl.

"Cycloalkylalkyl" refers to a moiety of the formula $R^c$—$R^d$—, where $R^c$ is cycloalkyl and $R^d$ is alkylene as defined herein.

"Halo", "halogen" and "halide" are used interchangeably herein and refer to fluoro, chloro, bromo, or iodo. Preferred halides are fluoro and chloro with fluoro being a particularly preferred halide.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroalkyl" means an alkyl moiety as defined herein wherein one or more, preferably one, two or three, hydrogen atoms have been replaced with a substituent independently selected from the group consisting of —OR$^a$, —NR$^b$R$^c$ (where n is 0 or 1 if R$^b$ and R$^c$ are both independently alkyl, cycloalkyl or cycloalkylalkyl, and 0 if not) and —S(O)$_n$R$^d$ (where n is an integer from 0 to 2), with the understanding that the point of attachment of the heteroalkyl moiety is through a carbon atom, wherein R$^a$ is hydrogen, acyl, alkoxycarbonyl, alkyl, hydroxyalkyl, alkoxyalkyl, alkylsulfonyl, aminocarbonyl, aminosulfonylamino, cycloalkyl, or cycloalkylalkyl; R$^b$ and R$^c$ are independently of each other hydrogen, acyl, alkoxycarbonyl, aminocarbonyl, aminocarbonyl, aminosulfonylamino, hydroxyalkyl, alkoxyalkyl, alkylsulfonyl, cycloalkyl, cycloalkylalkyl, alkylsulfonyl, aminosulfonyl, mono- or di-alkylaminosulfonyl, aminoalkyl, mono- or di-alkylaminoalkyl, hydroxyalkyl, alkoxyalkyl, hydroxyalkylsulfonyl or alkoxyalkylsulfonyl; and when n is 0, R$^d$ is hydrogen, alkyl, cycloalkyl, cycloalkylalkyl, or aryl, and when n is 1 or 2, R$^d$ is alkyl, cycloalkyl, cycloalkylalkyl, hydroxyalkyl, alkoxyalkyl, alkylamino, aminocarbonyl, aminosulfonylamino, alkylsulfonyl, amino, or optionally substituted phenyl. Representative examples include, but are not limited to, 2-hydroxyethyl, 3-hydroxypropyl,2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like. Accordingly, hydroxyalkyl and alkoxyalkyl are subset of heteroalkyl.

"Heteroaryl" means a monovalent monocyclic or bicyclic moiety of 5 to 12 ring atoms having at least one aromatic ring containing one, two, or three ring heteroatoms selected from N, O, or S (preferably N or O), the remaining ring atoms being C, with the understanding that the attachment point of the heteroaryl moiety will be on an aromatic ring. The heteroaryl ring is optionally substituted independently with one or more substituents, preferably one, two or three substituents, each of which is independently selected from alkyl, haloalkyl, hydroxy, alkoxy, halo, nitro and cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2a]-pyridinyl, imidazo[2,1-b]thiazolyl, and the derivatives thereof.

"Heteroarylalkyl" refers to a moiety of the formula Ar$^z$—R$^y$—, where Ar$^z$ is heteroaryl and R$^y$ is alkylene as defined herein.

"Heterocyclyl" means a saturated or unsaturated non-aromatic cyclic moiety of 3 to 8 ring atoms in which one or two ring atoms are heteroatoms selected from N, O, or S(O)$_n$, (where n is an integer from 0 to 2), preferably N or O, the remaining ring atoms being C, where one or two C atoms may optionally be replaced by a carbonyl group. The heterocyclyl ring may be optionally substituted independently with one or more, preferably one, two, or three, substituents, each of which is independently selected from alkyl, haloalkyl, hydroxyalkyl, halo, nitro, cyano, cyanoalkyl, hydroxy, alkoxy, amino, mono- and dialkylamino, aralkyl, —(X)$^n$—C(O)R$^e$ (where X is O or NR$^f$, n is 0 or 1, R$^e$ is hydrogen, alkyl, haloalkyl, hydroxy (when n is 0), alkoxy, amino, mono- and dialkylamino, or optionally substituted phenyl, and R$^f$ is H or alkyl), -alkylene-C(O)R$^g$ (where R$^g$ is alkyl, —OR$^h$ or NR$^i$R$^j$ and R$^h$ is hydrogen, alkyl or haloalkyl, and R$^i$ and R$^j$ are independently hydrogen or alkyl), and —S(O)$_n$R$^k$ (where n is an integer from 0 to 2) such that when n is 0, R$^k$ is hydrogen, alkyl, cycloalkyl, or cycloalkylalkyl, and when n is 1 or 2, R$^k$ is alkyl, cycloalkyl, cycloalkylalkyl, amino, acylamino, monoalkylamino, or dialkylamino. A particularly preferred group of heterocyclyl substituents include alkyl, haloalkyl, hydroxyalkyl, halo, hydroxy, alkoxy, amino, mono- and dialkylamino, aralkyl, and —S(O)$_n$R$^k$. In particular, the term heterocyclyl includes, but is not limited to, tetrahydrofuranyl, pyridinyl, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin4-yl, and the derivatives thereof, each of which may be optionally substituted.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" refers to a subset of cycloalkyl moiety as defined herein and specifically refers to a cycloalkyl moiety as defined herein where one or more, preferably one, two or three, hydrogen atoms in the cycloalkyl moiety have been replaced with a hydroxy substituent. Representative examples include, but are not limited to, 2-, 3-, or 4-hydroxycyclohexyl, and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted phenyl" means a phenyl ring which is optionally substituted independently with one or more substituents, preferably one or two substituents selected from the group consisting of alkyl, hydroxy, alkoxy, haloalkyl, haloalkoxy, halo, nitro, cyano, amino, methylenedioxy, ethylenedioxy, and acyl.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, or sulfhydryl group, respectively. Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p 1-92, Elesevier, N.Y.-Oxford (1985).

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, $2^{nd}$ ed. 1991) and Harrison and Harrison et al., *Compendium of Synthetic Organic Methods*, Vols. 1-8 (John Wiley and Sons, 1971-1996).Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

As used herein, the terms "those defined above" and "those defined herein" are used interchangeably herein and, when referring to a variable, incorporates by reference the broad definition of the variable as well as preferred, more preferred and most preferred definitions, if any.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The terms "those defined above" and "those defined herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen.

Compounds of the Invention

The invention provides compounds of formula Ia or Ib:

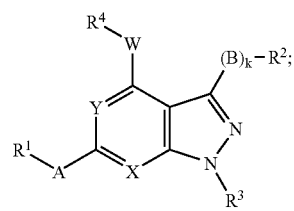

Ia

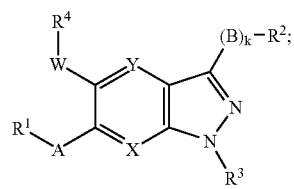

Ib

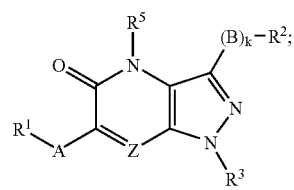

Ic or a pharmaceutically acceptable salt thereof, wherein:
$R^1$ is aryl, heteroaryl, aralkyl or cycloalkyl;
$R^2$ is aryl, heteroaryl, cycloalkyl, branched alkyl or heterocyclyl;
$R^3$ is hydrogen or alkyl;
$R^4$ is hydrogen, alkyl, hydroxy, amino, heteroalkyl, heterocyclyl, heterocyclylalkyl, hydroxycycloalkyl, cycloalkylalkyl, alkylsulfonyl, alkylsulfonamido, aryl, heteroaryl, aralkyl, heteroaralkyl, —(CHR$^a$)$_r$—C(=O)—R$^b$, —(CHR$^a$)$_r$—O—C(=O)—R$^b$, —(CHR$^a$)$_r$—NH—C(=O)—R$^b$ or —SO$_2$—R$^b$,
wherein
$R^a$ is hydrogen, alkyl or heteroalkyl;
$R^b$ is alkyl, hydroxy, amino, heteroalkyl, aryl, aralkyl, heteroaryl, or heterocyclyl;
r is from 0 to 4;

$R^5$ is hydrogen, alkyl, heteroalkyl, aralkyl, heteroaralkyl, heterocyclyl, hydroxycycloalkyl, —C(=O)—R$^c$ or —SO$_2$—R$^c$,
wherein
$R^c$ is alkyl, heteroalkyl, aryl, aralkyl, heteroaryl or heterocyclyl;
X and Y are nitrogen, or one of X and Y is nitrogen and the other is CR$^d$;
Z is N or CR$^d$,
wherein
$R^d$ is hydrogen, alkyl, hydroxy, alkoxy, amino, haloalkyl, cyano, halo, heteroalkyl, C(=O)—R$^e$ or —SO$_2$—R$^e$,
wherein
$R^e$ is hydrogen or alkyl;
W is O, S(O)$_m$, CH$_2$ or NR$^f$,
wherein
m is from 0 to 2, and
$R^f$ is hydrogen, alkyl, heteroalkyl, heterocyclyl, hydroxycycloalkyl, —C(=O)—R$^g$ or —SO$_2$—R$^g$,
wherein
$R^g$ is alkyl, aryl, aralkyl, heteroaryl, heteroalkyl or heterocyclyl;
or $R^4$ and $R^f$ together with the atoms to which they are attached may form a heterocyclic ring;
A is O, CH$_2$, S(O)$_n$, C(=O), NR$^h$, or CH(OR$^h$),
wherein
m is from 0 to 2, and
$R^h$ is hydrogen or alkyl,
or $R^1$ and $R^h$ may form a heterocyclyl;
k is 0 or 1;
B is O, S(O)$_j$, CH(OR$^i$), NR$^j$, or or C(=O),
wherein
j is0, 1 or 2;
$R^i$ is hydrogen or alkyl,
$R^j$ is hydrogen, alkyl, —C(=O)R$^k$, or —SO$_2$R$^m$,
wherein
$R^k$ is alkyl, aryl or aralkyl; and
$R^m$ is alkyl.

In many embodiments, the compounds of the invention are of formula Ia.

In certain embodiments of formula Ia, k is 0.

In certain embodiments of formula Ia, $R^3$ is hydrogen.

In certain embodiments of formula Ia, X and Y are nitrogen. In other embodiments, one of X and Y is nitrogen and the other is CR$^d$.

In many embodiments of formula Ia the subject compounds may be of the formula II:

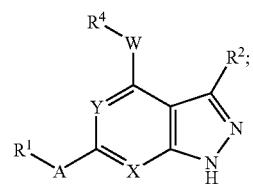

II wherein X, Y, Z, A, $R^1$, $R^2$ and $R^4$ are as defined in claim herein.

In certain embodiments of formula II, X and Y are nitrogen. In other embodiments, one of X and Y is nitrogen and the other is CR$^d$.

In certain embodiments of formula Ia the compounds of the invention may be of the formula III:

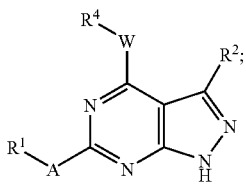

wherein A, W, $R^1$, $R^2$ and $R^4$ are as defined herein.

In certain embodiments of formulas Ia, II or III, A may be O, S or $NR^h$, and more preferably O.

In certain embodiments of formula Ia the compounds of the invention may be of the formula IV:

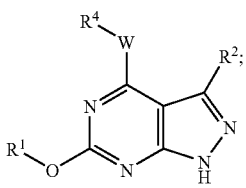

wherein W, $R^1$, $R^2$ and $R^4$ are as defined herein.

In embodiments of formulas Ia, II, III or IV, $R^1$ may be optionally substituted phenyl.

In certain embodiments of formulas Ia, II, III or IV, $R^1$ is 2-halophenyl or 2,4-dihalophenyl.

In certain embodiments of formulas Ia, II, III or IV, $R^2$ is optionally substituted phenyl, optionally substituted thienyl, or optionally substituted pyridyl. More preferably $R^2$ is optionally substituted phenyl.

In certain embodiments of formulas Ia, II, III or IV, $R^2$ is 2-halophenyl, 2,4-dihalophenyl, 2-alkoxyphenyl, 2-alkoxy4-halophenyl or 2-alkoxy-5-halophenyl.

In certain embodiments of formulas Ia, II, III or IV, $R^2$ is phenyl optionally substituted with halo, alkyl, amino, alkoxy, haloalkyl, hydroxy, hydroxyalkoxy, alkylsulfanyl, alkoxyamino, heteroaryl, heterocyclyl, heterocyclylalkyl, heterocyclyloxy, heterocyclylalkoxy, aminoalkoxy, hydroxyalkylamino, hydroxyalkylaminoalkyl, aralkyloxy, or pyridylalkyloxy. In certain embodiments $R^2$ is 2-chlorophenyl, 4-hydroxyphenyl, 4rmethoxyphenyl, 4-benzyloxyphenyl, 3-benzyloxyphenyl, 4-dimethylaminophenyl, 4-aminophenyl, 4-fluorophenyl, 3-fluorophenyl, 2-fluorophenyl, 3-trifluoromethyiphenyl, pyrid-3-yl, 4-(pyrid-2-yl)phenyl, 3-isopropoxyphenyl, 3,5-dimethyiphenyl, 1,3-benzodioxol-5-yl, 3-morpholinophenyl, 4-morpholinophenyl, 3-(4-methyl-piperazin-1-yl)-phenyl, 4-(4-methyl-piperazin-1-yl)-phenyl, N-methyl-N-(2-methoxyethyl)-phenyl, 2,4- difluorophenyl, 4-isopropyloxyphenyl, 3-{2-pyridin-2-yl-ethoxy)-phenyl, or thien-2-yl.

In certain embodiments of formulas Ia, II, III or IV, $R^2$ is phenyl optionally substituted with chloro, fluoro, bromo, methyl, methoxy, trifluoromethyl, pyridyl, morpholino, benzyloxy, 4-methylpiperidinyl, 2-methoxyethyl-methylamino, isopropoxy, pyridin-2-ylethoxy, amino, methylsulfanyl, 2,3-dihydroxypropoxy, 2-hydroxyethoxy, 2-(morpholin-4-yl)-ethoxy, 2-(dimethylamino)-ethoxy, 3,4-dihydroxybutyloxy, morpholin-4-ylmethyl, (2-hydroxypropyl)-aminomethyl, hydroxymethyl, ethoxy, piperidin-4-yloxy, or pyran-4-yloxy.

In certain embodiments of formula Ia the compounds of the invention may be of the formula V:

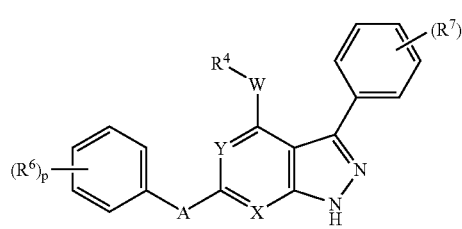

wherein:
each of p and q is independently from 0 to 4;
each $R^6$ is independently halo, alkyl, alkoxy, haloalkyl, or cyano;
each $R^7$ is independently halo, alkyl, haloalkyl, cyano, heteroalkyl, heterocyclyl, hydroxycycloalkyl or —C(=O)$R^n$,
wherein
$R^n$ is alkyl, heteroalkyl, aryl, aralkyl, heteroaryl or heterocyclyl; and
X, Y, A, W and $R^4$ are as defined herein.

In certain embodiments of formula V, X and Y are nitrogen. In other embodiments, one of X and Y is nitrogen and the other is $CR^d$.

In certain embodiments of formula Ia the compounds of the invention may be of the formula VI:

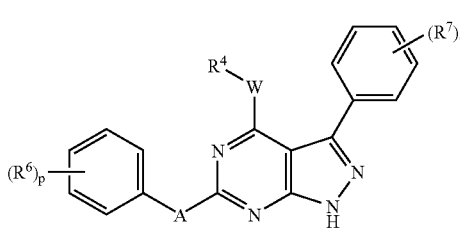

wherein p, q, A, W, $R^4$, $R^6$ and $R^7$ are as defined herein.

In certain embodiments of formulas V or VI, A may be O, S or $NR^h$, and more preferably O.

In certain embodiments of formula Ia the compounds of the invention may be of the formula VII:

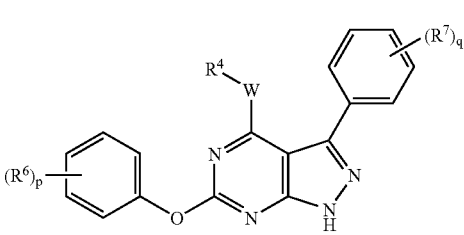

wherein p, q, W, $R^4$, $R^6$ and $R^7$ are as defined herein.

In certain embodiments of formulas Ia, II, III, IV, V, VI or VII, W may be $NR^f$ or O.

In certain embodiments of formula Ia the compounds of the invention may be of the formula VIII:

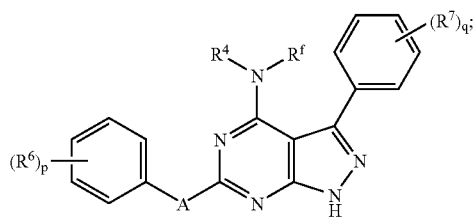

wherein p, q, A, $R^4$, $R^6$, $R^7$ and $R^f$ are as defined herein.

In certain embodiments of formula VIII, A may be O, S or $NR^h$, and more preferably O.

In certain embodiments of formula Ia the compounds of the invention may be of the formula VIII:

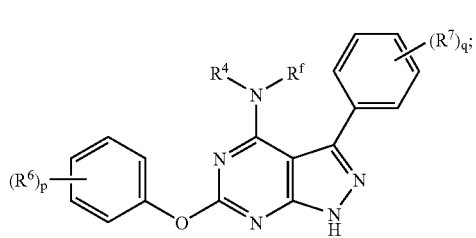

wherein p, q, $R^4$, $R^6$, $R^7$ and $R^f$ are as defined herein.

In certain embodiments of formula Ia the compounds of the invention may be of the formula X:

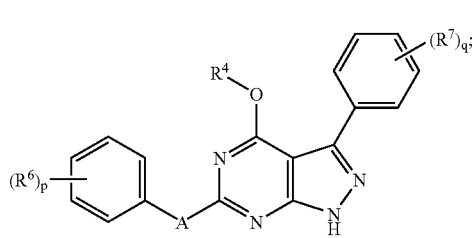

wherein p, q, A, $R^4$, $R^6$, and $R^7$ are as defined herein.

In certain embodiments of formula X, A may be O, S or $NR^f$, and more preferably O.

In certain embodiments of formula Ia the compounds of the invention may be of the formula XI:

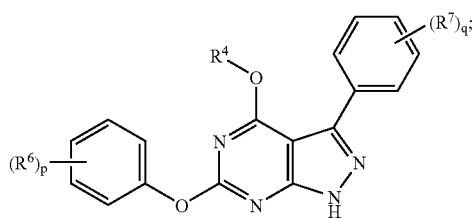

wherein p, q, $R^4$ $R^6$, and $R^7$ are as defined herein.

In certain embodiments of formulas V, VI, VII, VIII, IX, X or XI, p is 1 or 2 and $R^6$ is halo. Preferably $R^6$ is fluoro or chloro, and more preferably fluoro.

In certain embodiments of formulas V, VI, VII, VIII, IX, X or XI, $R^2$ is halo, alkyl, amino, alkoxy, haloalkyl, hydroxy, hydroxyalkoxy, alkylsulfanyl, alkoxyamino, heteroaryl, heterocyclyl, heterocyclylalkyl, heterocyclyloxy, heterocyclylalkoxy, aminoalkoxy, hydroxyalkylamino, hydroxyalkylaminoalkyl, aralkyloxy, or pyridylalkyloxy.

In certain embodiments of formulas V, VI, VII, VIII, IX, X or XI, $R^2$ is chloro, fluoro, bromo, methyl, methoxy, trifluoromethyl, pyridyl, morpholino, benzyloxy, 4-methylpiperidinyl, 2-methoxyethyl-methylamino, isopropoxy, pyridin-2-ylethoxy, amino, methylsulfanyl, 2,3-dihydroxypropoxy, 2-hydroxyethoxy, 2-(morpholin-4-yl)-ethoxy, 2-(dimethylamino)-ethoxy, 3,4-dihydroxybutyloxy, morpholin-4-ylmethyl, (2-hydroxypropyl)-aminomethyl, hydroxymethyl, ethoxy, piperidin-4-yloxy, or pyran-4-yloxy.

In certain embodiments of formulas Ia, II, III, IV, V, VI, VII, VIII, IX, X or XI, $R^4$ is heteroalkyl, heterocyclyl, heterocyclylalkyl, heteroaralkyl, hydroxycycloalkyl, —$(CHR^a)_r$—C($=$O)—$R^b$, or $R^4$ and $R^f$ together with the nitrogen to which they are attached form a heterocyclyl.

In certain embodiments of formulas Ia, II, III, IV, V, VI, VII, VIII, IX, X or XI, $R^4$ is heteroalkyl.

In certain embodiments of formulasIa, II, III, IV, V, VI, VII, VIII, IX, X or XI where $R^4$ is heteroalkyl, $R^4$ may be hydroxyalkyl, alkoxyalkyl, hydroxyalkoxyalkyl, aminoalkyl, alkylsulfonylalkyl, alkylsulfonylaminoalkyl or aminosulfonylaminoalkyl.

In certain embodiments of formulas Ia, II, III, IV, V, VI, VII, VIII, IX, X or XI, $R^4$ is hydroxyalkyl.

In certain embodiments of formulas Ia, II, III, IV, V, VI, VII, VIII, IX, X or XI where $R^4$ is hydroxyalkyl, $R^4$ may be 2-hydroxypropyl, 2,3-dihydroxypropyl, 1-hydroxypropan-2-yl, 2-hydroxyethyl, 2,3,4,5,6-pentahydroxyhexyl, 1,5-dihydroxypentan-3-yl, 3,4-dihydroxybutyl, 1,3-dihydroxybutan-2-yl, 2-hydroxymethyl-1,3-dihydroxypropan-2-yl, 3-hydroxy-3-methylbutyl, 2-hydroxy-2-methylpropyl, 3-hydroxy-3-methylbutan-2-yl, 4,5-dihydroxypentyl, 3-hydroxypropyl, or 1,3-dihydroxy-2-methylpropan-2-yl. Preferred hydroxyalkyl include (R)-2-hydroxypropyl and (S)-2-hydroxypropyl In certain embodiments of formulas Ia, II, III, IV, V, VI, VII, VIII, IX, X or XI, $R^4$ is heterocyclyl.

In certain embodiments of formulas Ia, II, III, IV, V, VI, VII, VIII, IX, X or XI where $R^4$ is heterocyclyl, $R^4$ may be tetrahydropyran-4-yl, piperidin-4-yl, 1-methanesulfonylpiperidin-4-yl, 3-hydroxytetrahydropyran-4-yl, 3-hydroxytetrahydrofuran-4-yl, or 3-hydroxyhexahydrofuro-[3,2-b]furan-3-yl.

In certain embodiments of formulas Ia, II, III, IV, V, VI, VII, VIII, IX, X or XI, $R^4$ is heterocyclylalkyl.

In certain embodiments of formulas Ia, II, III, IV, V, VI, VII, VIII, IX, X or XI where $R^4$ is heterocyclylalkyl, $R^4$ may be 3-(morpholin-4-yl)-propyl, 2-(morpholin-4-yl)-ethyl, 3-(4-methylpiperazin-1-yl)-propyl, 2-(tetrahydrofuran4-yl)-ethyl, tetrahydrofuran-2-ylmethyl,3-fluorooxetan-3-ylmethyl, 3-hydroxymethyloxetan-3-ylmethyl, 2,2-dimethyl[1,3]dioxolan-4-ylmethyl, 2-(pyrrolidine-2,5-dione-1-yl)-ethyl, 2-(imidazolin-2-one-1-yl)-ethyl, 2-(2,2-dimethyl[1,3]dioxolan-4-yl)-ethyl, 3-(2,2dimethyl[1,3]dioxolan-4-yl)-propyl, 2-(pyrrolidin-2-one-1-yl)-ethyl, 2-(4-methylpiperazin-1-yl)-ethyl, 2-(4-methanesulfonylpiperazin-1-yl)-ethyl, 2-(oxazolidin-2-one-1-yl)-ethyl, 1,4-dioxan-2-ylmethyl, 2-(pyrrolidin-1-yl)-ethyl, 1-methylpiperidin-4-ylmethyl, or 2-(3-methylimidazolin-2-one-1-yl)-ethyl.

In certain embodiments of formulas Ia, II, III, IV, V, VI, VII, VII, IX, X or XI, $R^4$ is heteroaralkyl.

In certain embodiments of formulas Ia, II, III, IV, V, VI, VII, VIII, IX, X or XI where $R^4$ is heteroaralkyl, $R^4$ may be 2-(2-methylimidazol-1-yl)-ethyl, 2-(oxazdiazol-2-yl)-ethyl, 2-(4-methyl-2,3-dihydro-[1,2,4]-triazol-3-one-5-yl)-ethyl, 2-(1-methylimidazol-2-yl)-ethyl, 2-(1-methoxymethyl-[1,2,4]-triazol-3-yl)-ethyl, 2-(2-methoxymethyl-[1,2,4]-triazol-3-yl)-ethyl, 2-[1,2,4]-triazol-3-yl)-ethyl, 2-(2,4-dihydro-[1,2,4]-triazol-3-one-4-yl)-ethyl, In certain embodiments of formulas Ia, II, III, IV, V, VI, VII, VIII, IX, X or XI, $R^4$ is —(CHR$^a$)$_r$—C(=O)—R$^b$.

In certain embodiments of formulas Ia, II, III, IV, V, VI, VII, VIII, IX, X or XI where $R^4$ is —(CHR$^a$)$_r$—C(=O)—R$^b$, r is 1, 2 or 3, $R^a$ is hydrogen, and $R^b$ is tert-butoxy, hydroxy, morpholin-4-yl, dimethylamino or methyl.

In certain embodiments of formulas Ia, II, III, IV, V, VI, VII, VIII, IX, X or XI where $R^4$ is —(CHR$^a$)$_r$—C(=O)R$^b$, r is 1, $R^a$ is hydroxymethyl or 1-hydroxyethyl, and $R^b$ is tert-butoxy, hydroxy, morpholin-4-yl, dimethylamino or methyl.

In certain embodiments of formulas Ia, II, III, IV, V, VI, VII, VIII, IX, X or XI, $R^4$ and $R^f$ together with the nitrogen to which they are attached form a heterocyclyl.

In certain embodiments of formulas Ia, II, III, IV, V, VI, VII, VIII, IX, X or XI where $R^4$ and $R^f$ together with the nitrogen to which they are attached form a heterocyclyl, such heterocyclyl may be 1,1-dioxo-1lambda*6*-thiomorpholin-4-yl, 1,1-dioxo-1lambda*6*-[1,2]thiazinan-2-yl, 4-methylpiperazin-1-yl, 4-hydroxypiperidin-1-yl, 4-methanesulfonylpiperazin-1-yl, morpholin-4-yl, 4-hydroxymethylpiperidin-1-yl, 4-(2-hydroxyethyl)-piperidin-1-yl, 3-hydroxyazetidin-1-yl, 2-hydroxymethylpyrrolidin-1-yl, 3-hydroxypiperidin-1-yl, 4-(pyrimidin-2-yl)-piperazin-1-yl, or 3-hydroxypyrrolodin-1-yl.

In certain embodiments of formulas Ia, II, III, IV, V, VI, VII, VIII, IX, X or XI, $R^4$ is hydroxycycloalkyl.

In certain embodiments of formulas Ia, II, III, IV, V, VI, VII, VIII, IX, X or XI where $R^4$ is hydroxycycloalkyl, $R^4$ may be hydroxycyclohexan-2-yl, hydroxycyclopentan-2-yl, or 1,3-dihydroxycyclohexan-5-yl.

In certain embodiments of formula Ib, X and Y are nitrogen. In other embodiments, one of X and Y is nitrogen and the other is CR$^d$.

In certain embodiments of formula Ib, the compounds of the invention may be more specifically of the formula XII:

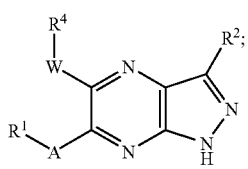

XII wherein A, W, $R^1$, $R^2$ and $R^4$ are as defined herein.

In certain embodiments of formula Ib, the compounds of the invention may be more specifically of the formula XIII:

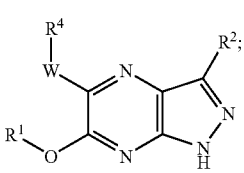

XIII wherein W, $R^1$, $R^2$ and $R^4$ are as defined herein.

In certain embodiments of formula Ib, the compounds of the invention may be more specifically of the formula XIV:

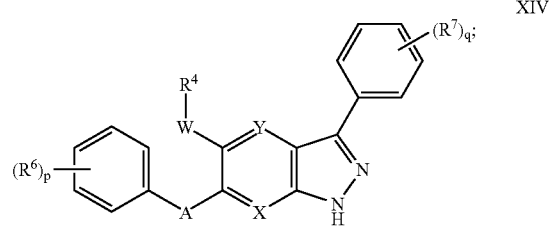

XIV wherein p, q, A, X, Y, W, $R^4$, $R^6$ and $R^7$ are as defined herein.

In certain embodiments of formula XIV, X and Y are nitrogen. In other embodiments, one of X and Y is nitrogen and the other is CR$^d$.

In certain embodiments of formula Ib, the compounds of the invention may be more specifically of the formula XV:

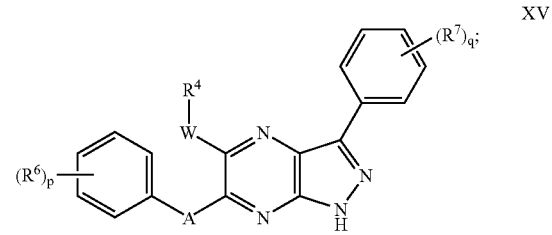

XV wherein p, q, A, W, $R^4$, $R^6$ and $R^7$ are as defined herein.

In certain embodiments of formula Ib, the compounds of the invention may be more specifically of the formula XVI:

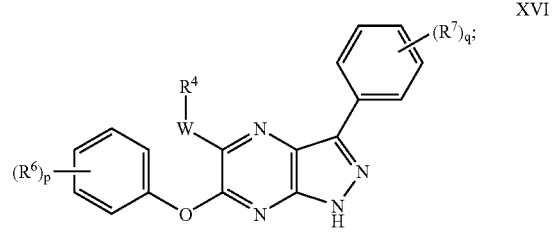

XVI wherein p, q, W, $R^4$, $R^6$ and $R^7$ are as defined herein.

In certain embodiments of formula Ic, Z is CR$^c$ such that the subject compounds can be represented by formula XVII:

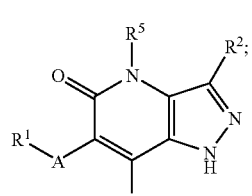

XVII wherein A, $R^1$, $R^2$, $R^5$ and $R^c$ are as defined above.

In certain embodiments of formula Ic the compounds of the invention may be represented by formula XVIII:

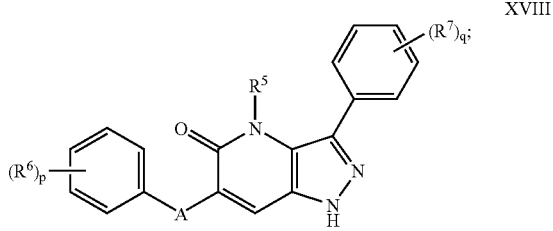

wherein
each of p and q is independently from 0 to 4;
each $R^6$ is independently halo, alkyl, alkoxy, haloalkyl, or cyano;
each $R^7$ is independently halo, alkyl, haloalkyl, cyano, heteroalkyl, heterocyclyl, hydroxycycloalkyl or —C(=O)—R″,
wherein
R″ is alkyl, heteroalkyl, aryl, aralkyl, heteroaryl or heterocyclyl; and -A and $R^5$ are as defined herein.

In specific embodiments of formula Ic, compounds of the invention may be represented by formula XIX:

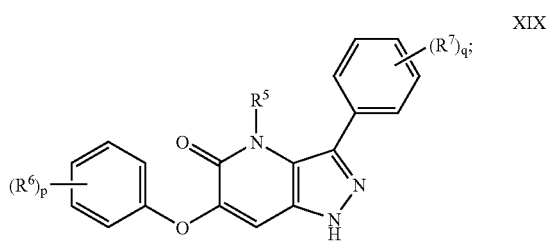

wherein p, q, $R^5$ $R^6$ and $R^7$ are as defined herein.

In embodiments of the invention where any of $R^1$, $R^2$, $R^3$, $R^4$, $R^5$, $R^6$, $R^7$, $R^a$, $R^b$, $R^c$, $R^d$, $R^e$, $R^f$, $R^g$, $R^h$, $R^i$, $R^j$ or $R^k$ is alkyl or contains an alkyl moiety, such alkyl is preferably lower alkyl, i.e. $C_1$-$C_6$alkyl, and more preferably $C_1$-$C_4$alkyl.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science*, 1977, 66, 1-19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Representative compounds in accordance with the invention are shown below in Table 1.

TABLE 1

| # | Structure | Name (Autonom ™) | MP ° C. or M + H | Example |
|---|---|---|---|---|
| 1 | 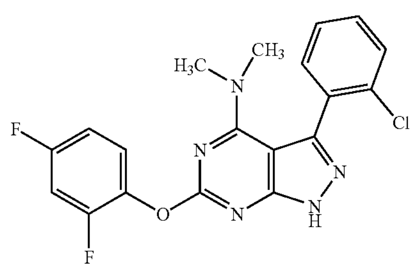 | [3-(2-Chloro-phenyl)-6-(2,4-difluoro-phenoxy)-1H-pyrazolo[3,4-d]pyrimidin-4-yl]-dimethyl-amine | 403 | 1 |
| 2 | 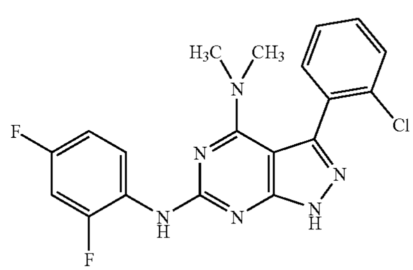 | 3-(2-Chloro-phenyl)-N-*6*-(2,4-difluoro-phenyl)-N*4*,N*4*-dimethyl-1H-pyrazolo[3,4-d]pyrimidine-4,6-diamine | 402 | 1 |

TABLE 1-continued

| # | Structure | Name (Autonom ™) | MP ° C. or M + H | Example |
|---|---|---|---|---|
| 3 | 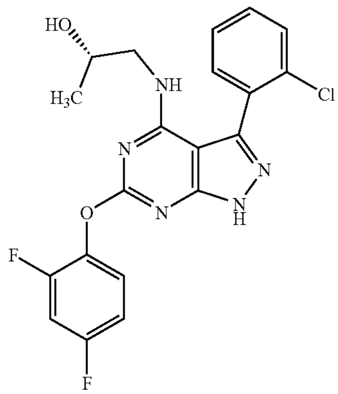 | 1-[3-(2-Chloro-phenyl)-6-(2,4-difluoro-phenoxy)-1H-pyrazolol[3,4-d]pyrimidin-4-ylamino]-propan-2-ol | 254.6-258.2° C. | 1 |
| 4 | 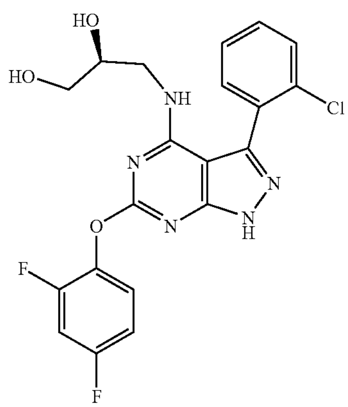 | 3-[3-(2-Chloro-phenyl)-6-(2,4-difluoro-phenoxy)-1H-pyrazolo[3,4-d]pyrimidin-4-ylamino]-propane-1,2-diol | 449 | 1 |
| 5 | 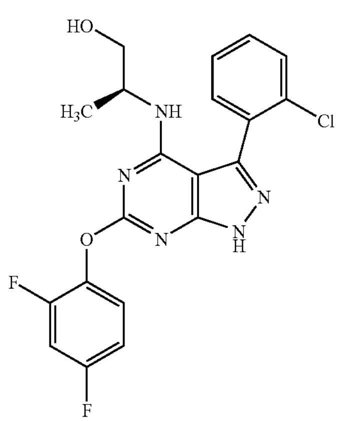 | 2-[3-(2-Chloro-phenyl)-6-(2,4-difluoro-phenoxy)-1H-pyrazolo[3,4-d]pyrimidin-4-ylamino]-propan-1-ol | 433 | 1 |

TABLE 1-continued

| # | Structure | Name (Autonom ™) | MP ° C. or M + H | Example |
|---|---|---|---|---|
| 6 | 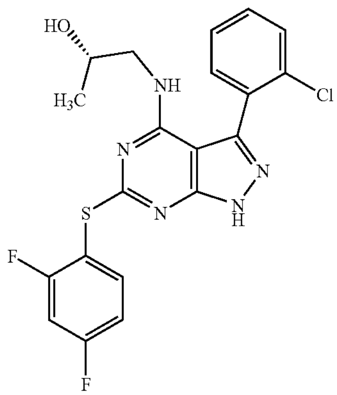 | 1-[3-(2-Chloro-phenyl)-6-(2,4-difluoro-phenylsulfanyl)-1H-pyrazolo[3,4-d]pyrimidin-4-ylamino]-propan-2-ol | 449 | 1 |
| 7 | 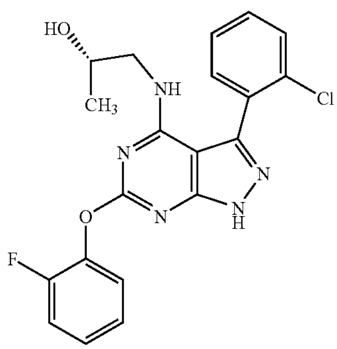 | 1-[3-(2-Chloro-phenyl)-6-(2-fluoro-phenoxy)-1H-pyrazolo[3,4-d]pyrimidin-4-ylamino]-propan-2-ol | 415 | 1 |
| 8 | 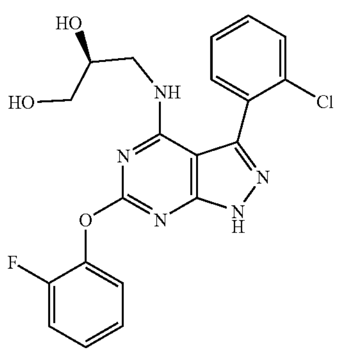 | 3-[3-(2-Chloro-phenyl)-6-(2-fluoro-phenoxy)-1H-pyrazolo[3,4-d]pyrimidin-4-ylamino]-propane-1,2-diol | 172.0-175.3° C. | 1 |
| 9 | 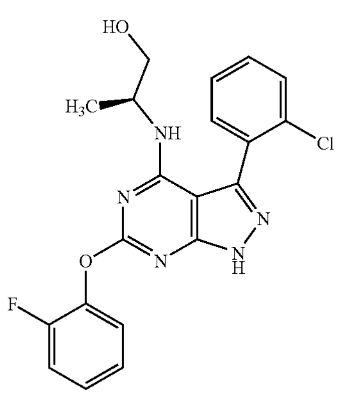 | 2-[3-(2-Chloro-phenyl)-6-(2-fluoro-phenoxy)-1H-pyrazolo[3,4-d]pyrimidin-4-ylamino]-propan-1-ol | 97.0-110.7° C. | 1 |

TABLE 1-continued

| # | Structure | Name (Autonom ™) | MP ° C. or M + H | Example |
|---|---|---|---|---|
| 10 | 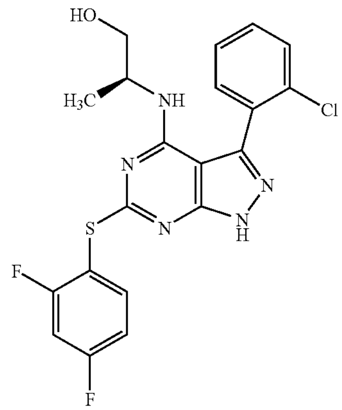 | 2-[3-(2-Chloro-phenyl)-6-(2,4-difluoro-phenylsulfanyl)-1H-pyrazolo[3,4-d]pyrimidin-4-ylamino]-propan-1-ol | 94.3-98.1° C. | 1 |
| 11 | 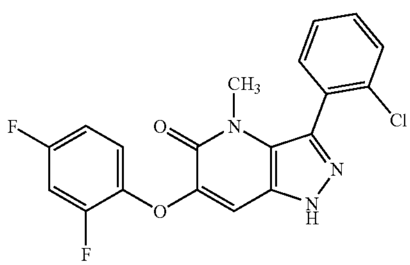 | 3-(2-Chloro-phenyl)-6-(2,4-difluoro-phenoxy)-4-methyl-1,4-dihydro-pyrazolo[4,3-b]pyridin-5-one | 389 | 2 |
| 12 | 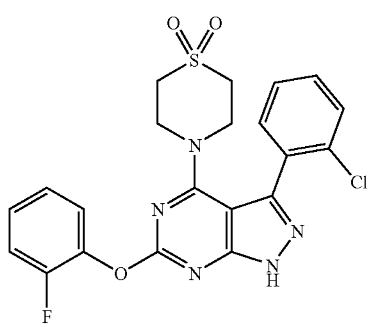 | 3-(2-Chloro-phenyl)-4-(1,1-dioxo-1lambda*6*-thiomorpholin-4-yl)-6-(2-fluoro-phenoxy)-1H-pyrazolo[3,4-d]pyrimidine | 475 | 1 |
| 13 | 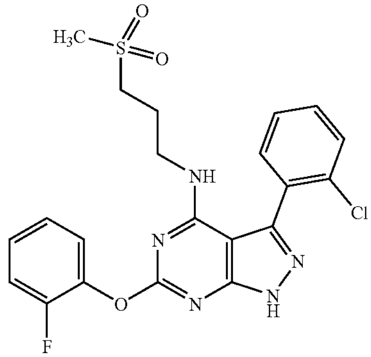 | [3-(2-Chloro-phenyl)-6-(2-fluoro-phenoxy)-1H-pyrazolo[3,4-d]pyrimidin-4-yl]-(3-methanesulfonyl-propyl)-amine | 477 | 1 |

TABLE 1-continued

| # | Structure | Name (Autonom ™) | MP ° C. or M + H | Example |
|---|---|---|---|---|
| 14 | 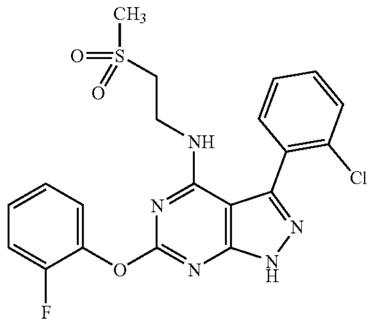 | [3-(2-Chloro-phenyl)-6-(2-fluoro-phenoxy)-1H-pyrazolo[3,4-d]pyrimidin-4-yl]-(2-methanesulfonyl-ethyl)-amine | 463 | 1 |
| 15 | 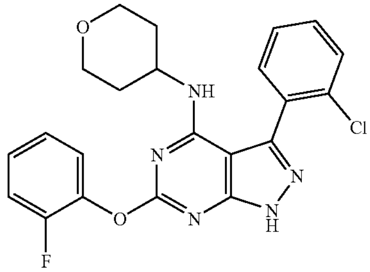 | [3-(2-Chloro-phenyl)-6-(2-fluoro-phenoxy)-1H-pyrazolo[3,4-d]pyrimidin-4-yl]-(tetrahydro-pyran-4-yl)-amine | 441 | 1 |
| 16 | 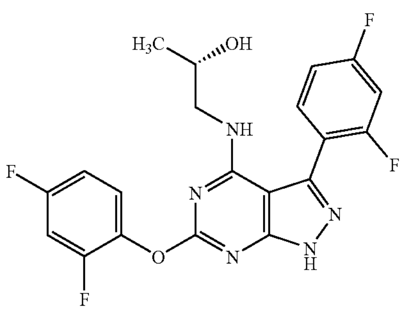 | 1-[6-(2,4-Difluoro-phenoxy)-3-(2,4-difluoro-phenyl)-1H-pyrazolo[3,4-d]pyrimidin-4-ylamino]-propan-2-ol | 434 | 1 |
| 17 | 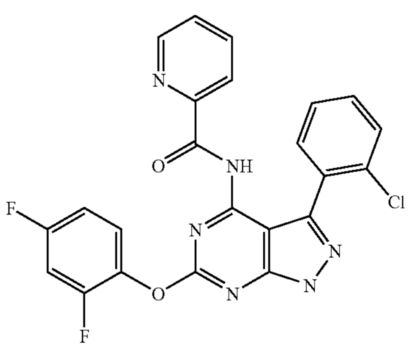 | Pyridine-2-carboxylic acid [3-(2-chloro-phenyl)-6-(2,4-difluoro-phenoxy)-1H-pyrazolo[3,4-d]pyrimidin-4-yl]-amide | 480 | 3 |
| 18 | 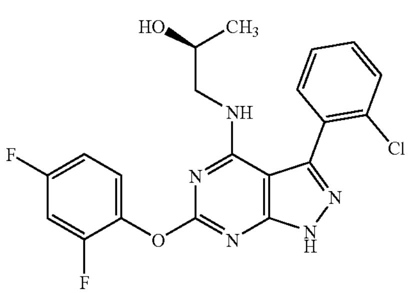 | 1-[3-(2-Chloro-phenyl)-6-(2,4-difluoro-phenoxy)-1H-pyrazolo[3,4-d]pyrimidin-4-ylamino]-propan-2-ol | 433 | 1 |

TABLE 1-continued

| # | Structure | Name (Autonom ™) | MP ° C. or M + H | Example |
|---|---|---|---|---|
| 19 | 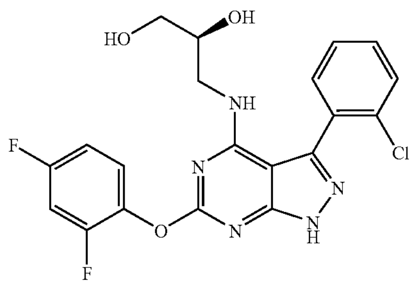 | 3-[3-(2-Chloro-phenyl)-6-(2,4-difluoro-phenoxy)-1H-pyrazolo[3,4-d]pyrimidin-4-ylamino]-propane-1,2-diol | 449 | 1 |
| 20 | 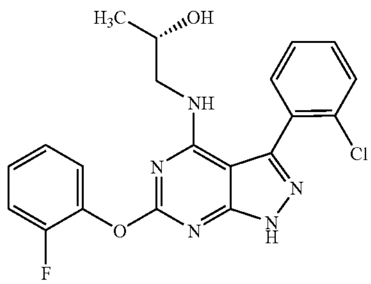 | 1-[3-(2-Chloro-phenyl)-6-(2-fluoro-phenoxy)-1H-pyrazolo[3,4-d]pyrimidin-4-ylamino]-propan-2-ol | 415 | 1 |
| 21 | 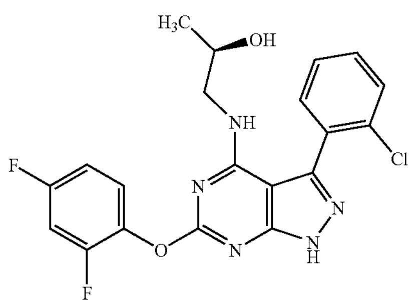 | 1-[3-(2-Chloro-phenyl)-6-(2,4-difluoro-phenoxy)-1H-pyrazolo[3,4-d]pyrimidin-4-ylamino]-propan-2-ol | 433 | 1 |
| 22 | 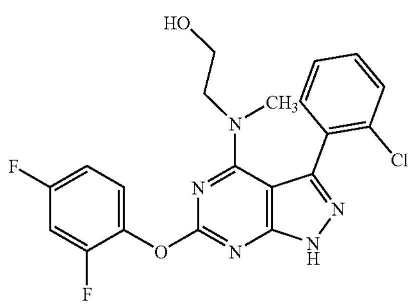 | 2-{[3-(2-Chloro-phenyl)-6-(2,4-difluoro-phenoxy)-1H-pyrazolo[3,4-d]pyrimidin-4-yl]-methyl-amino}-ethanol | 433 | 1 |
| 23 | 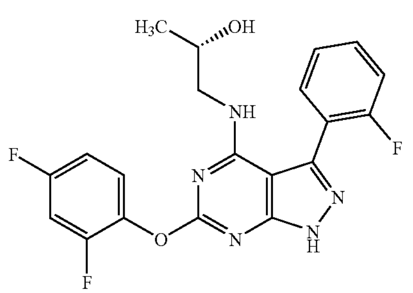 | 1-[6-(2,4-Difluoro-phenoxy)-3-(2-fluoro-phenyl)-1H-pyrazolo[3,4-d]pyrimidin-4-ylamino]-propan-2-ol | 416 | 1 |

TABLE 1-continued

| # | Structure | Name (Autonom ™) | MP ° C. or M + H | Example |
|---|-----------|------------------|------------------|---------|
| 24 | 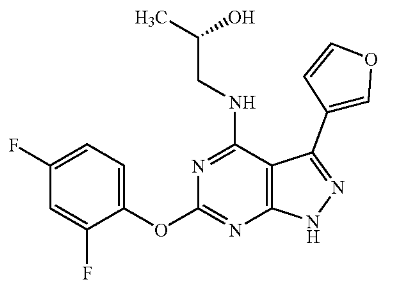 | 1-[6-(2,4-Difluoro-phenoxy)-3-furan-3-yl-1H-pyrazolo[3,4-d]pyrimidin-4-ylamino]-propan-2-ol | 388 | 4 |
| 25 | 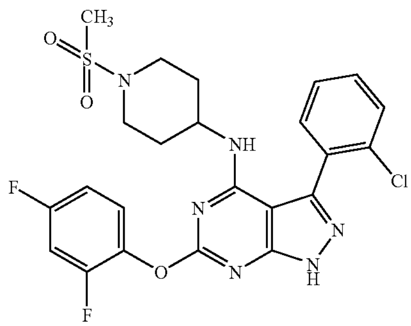 | [3-(2-Chloro-phenyl)-6-(2,4-difluoro-phenoxy)-1H-pyrazolo[3,4-d]pyrimidin-4-yl]-(1-methanesulfonyl-piperidin-4-yl)-amine | 536 | 1 |
| 26 | 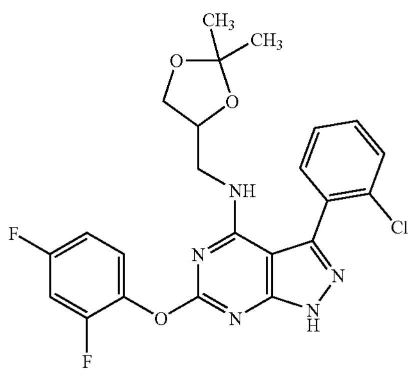 | [3-(2-Chloro-phenyl)-6-(2,4-difluoro-phenoxy)-1H-pyrazolo[3,4-d]pyrimidin-4-yl]-(2,2-dimethyl-[1,3]dioxolan-4-ylmethyl)-amine | 489 | 1 |
| 27 | 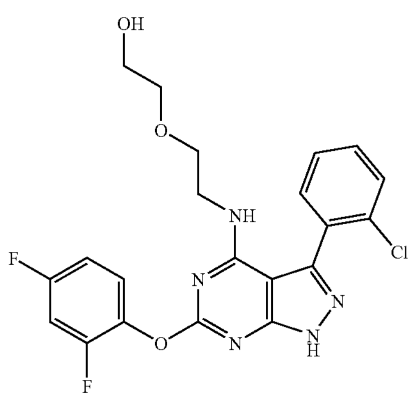 | 2-{2-[3-(2-Chloro-phenyl)-6-(2,4-difluoro-phenoxy)-1H-pyrazolo[3,4-d]pyrimidin-4-ylamino]-ethoxy}-ethanol | 463 | 1 |

TABLE 1-continued

| # | Structure | Name (Autonom ™) | MP ° C. or M + H | Example |
|---|---|---|---|---|
| 28 | 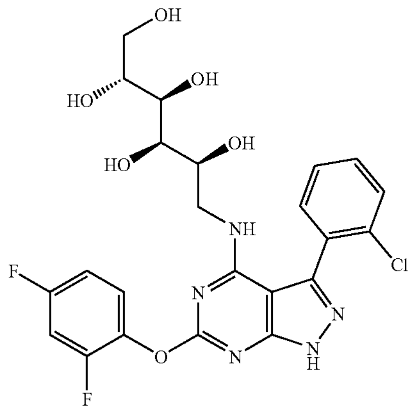 | 6-[3-(2-Chloro-phenyl)-6-(2,4-difluoro-phenoxy)-1H-pyrazolo[3,4-d]pyrimidin-4-ylamino]-hexane-1,2,3,4,5-pentaol | 539 | 1 |
| 29 | 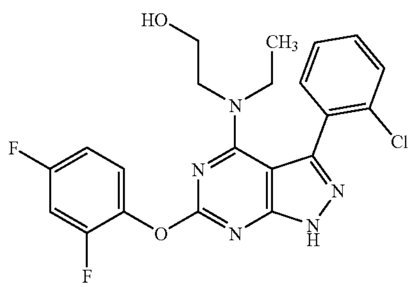 | 2-{[3-(2-Chloro-phenyl)-6-(2,4-difluoro-phenoxy)-1H-pyrazolo[3,4-d]pyrimidin-4-yl]-ethyl-amino}-ethanol | 447 | 1 |
| 30 | 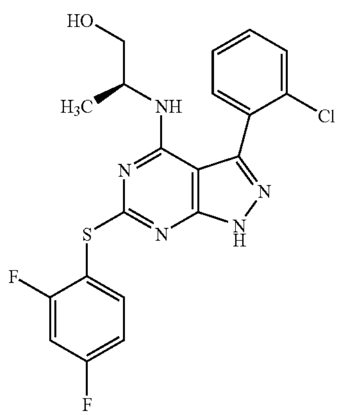 | 1-[6-(2,4-Difluoro-phenoxy)-3-(2-methoxy-phenyl)-1H-pyrazolo[3,4-d]pyrimidin-4-ylamino]-propan-2-ol | 428 | 4 |
| 31 | 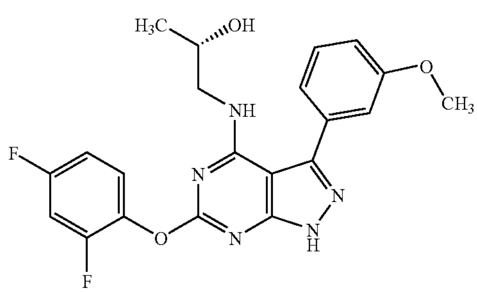 | 1-[6-(2,4-Difluoro-phenoxy)-3-(3-methoxy-phenyl)-1H-pyrazolo[3,4-d]pyrimidin-4-ylamino]-propan-2-ol | 428 | 4 |

TABLE 1-continued

| # | Structure | Name (Autonom ™) | MP ° C. or M + H | Example |
|---|---|---|---|---|
| 32 | 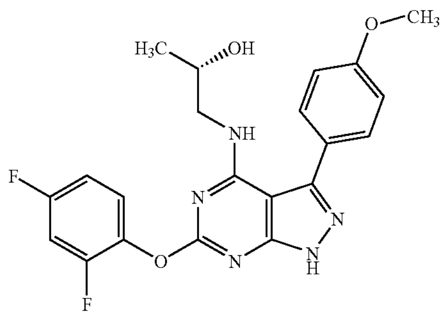 | 1-[6-(2,4-Difluoro-phenoxy)-3-(4-methoxy-phenyl)-1H-pyrazolo[3,4-d]pyrimidin-4-ylamino]-propan-2-ol | 428 | 4 |
| 33 | 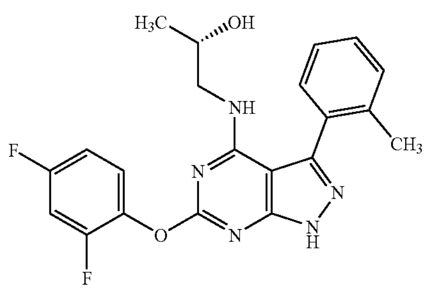 | 1-[6-(2,4-Difluoro-phenoxy)-3-o-tolyl-1H-pyrazolo[3,4-d]pyrimidin-4-ylamino]-propan-2-ol | 412 | 4 |
| 34 | 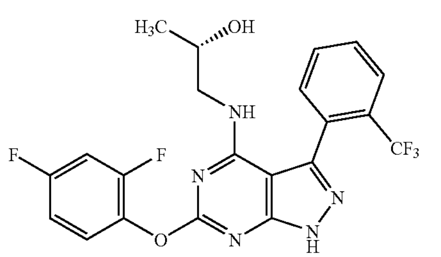 | 1-[6-(2,4-Difluoro-phenoxy)-3-o-tolyl-1H-pyrazolo[3,4-d]pyrimidin-4-ylamino]-propan-2-ol | 466 | 4 |
| 35 | 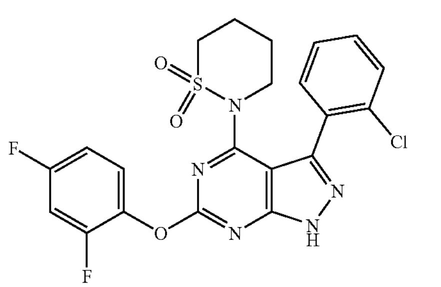 | 3-(2-Chloro-phenyl)-6-(2,4-difluoro-phenoxy)-4-(1,1-dioxo-1lambda*6*-[1,2]thiazinan-2-yl)-1H-pyrazolo[3,4-d]pyrimidine | 493 | 1 |
| 36 | 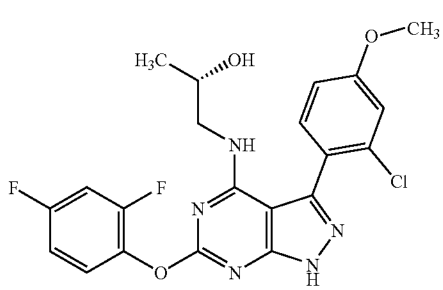 | 1-[3-(2-Chloro-4-methoxy-phenyl)-6-(2,4-difluoro-phenoxy)-1H-pyrazolo[3,4-d]pyrimidin-4-ylamino]-propan-2-ol | 463 | 4 |

TABLE 1-continued

| # | Structure | Name (Autonom ™) | MP ° C. or M + H | Example |
|---|---|---|---|---|
| 37 | 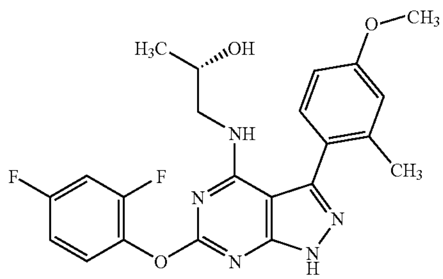 | 1-[6-(2,4-Difluoro-phenoxy)-3-(4-methoxy-2-methyl-phenyl)-1H-pyrazolo[3,4-d]pyrimidin-4-ylamino]-propan-2-ol | 442 | 4 |
| 38 | 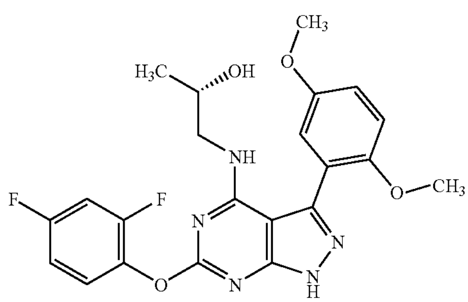 | 1-[6-(2,4-Difluoro-phenoxy)-3-(2,5-dimethoxy-phenyl)-1H-pyrazolo[3,4-d]pyrimidin-4-ylamino]-propan-2-ol | 458 | 4 |
| 39 | 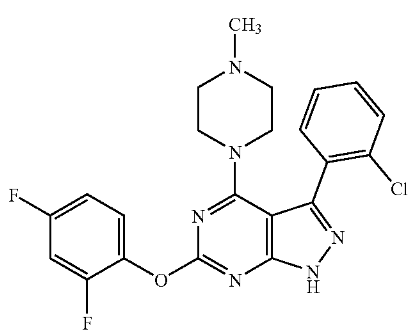 | 3-(2-Chloro-phenyl)-6-(2,4-difluoro-phenoxy)-4-(4-methyl-piperazin-1-yl)-1H-pyrazolo[3,4-d]pyrimidine | 458 | 1 |
| 40 | 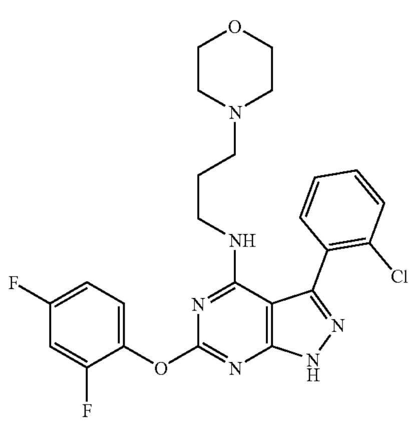 | [3-(2-Chloro-phenyl)-6-(2,4-difluoro-phenoxy)-1H-pyrazolo[3,4-d]pyrimidin-4-yl]-(3-morpholin-4-yl-propyl)-amine | 502 | 1 |

TABLE 1-continued

| # | Structure | Name (Autonom ™) | MP ° C. or M + H | Example |
|---|---|---|---|---|
| 41 | 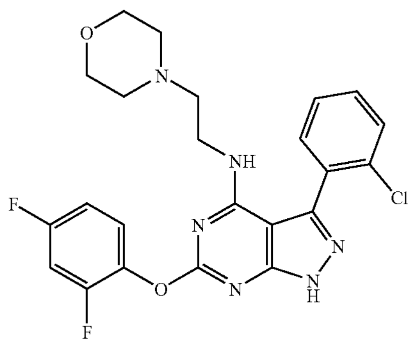 | [3-(2-Chloro-phenyl)-6-(2,4-difluoro-phenoxy)-1H-pyrazolo[3,4-d]pyrimidin-4-yl]-(2-morpholin-4-yl-ethyl)-amine | 488 | 1 |
| 42 | 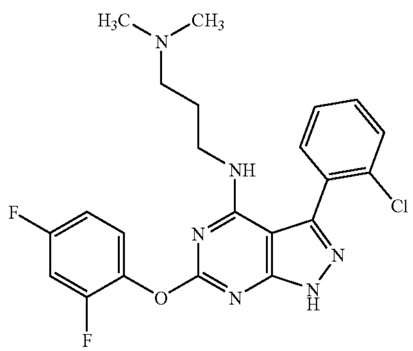 | N'-[3-(2-Chloro-phenyl)-6-(2,4-difluoro-phenoxy)-1H-pyrazolo[3,4-d]pyrimidin-4-yl]-N,N-dimethyl-propane-1,3-diamine | 460 | 1 |
| 43 | 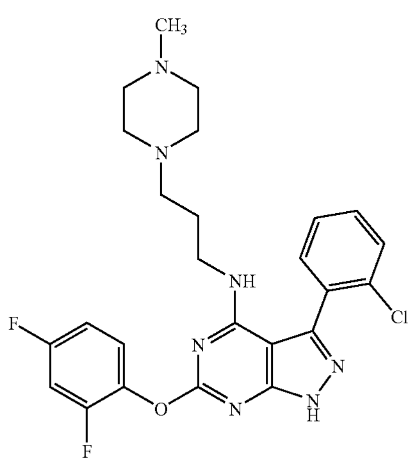 | [3-(2-Chloro-phenyl)-6-(2,4-difluoro-phenoxy)-1H-pyrazolo[3,4-d]pyrimidin-4-yl]-[3-(4-methyl-piperazin-1-yl)-propyl]-amine | 515 | 1 |
| 44 | 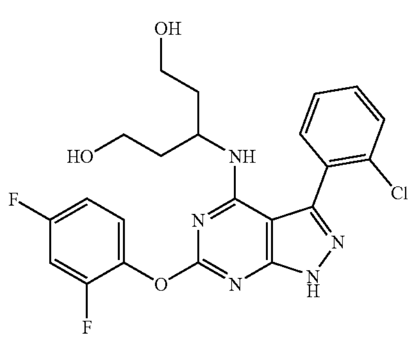 | 3-[3-(2-Chloro-phenyl)-6-(2,4-difluoro-phenoxy)-1H-pyrazolo[3,4-d]pyrimidin-4-ylamino]-pentane-1,5-diol | 477 | 1 |

TABLE 1-continued

| # | Structure | Name (Autonom ™) | MP ° C. or M + H | Example |
|---|---|---|---|---|
| 45 | 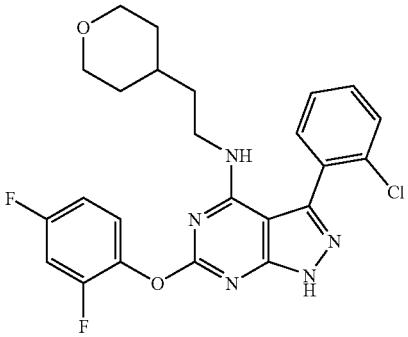 | [3-(2-Chloro-phenyl)-6-(2,4-difluoro-phenoxy)-1H-pyrazolo[3,4-d]pyrimidin-4-yl]-[2-(tetrahydro-pyran-4-yl)-ethyl]-amine | 487 | 1 |
| 46 | 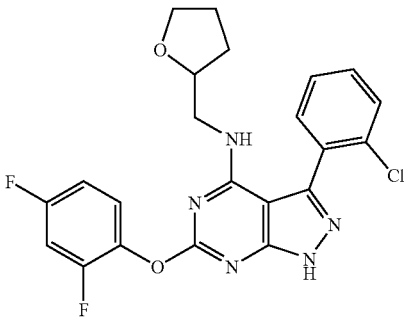 | [3-(2-Chloro-phenyl)-6-(2,4-difluoro-phenoxy)-1H-pyrazolo[3,4-d]pyrimidin-4-yl]-(tetrahydro-furan-2-ylmethyl)-amine | 459 | 1 |
| 47 | 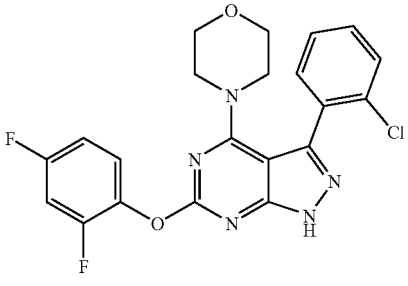 | 3-(2-Chloro-phenyl)-6-(2,4-difluoro-phenoxy)-4-morpholin-4-yl-1H-pyrazolo[3,4-d]pyrimidine | 445 | 1 |
| 48 | 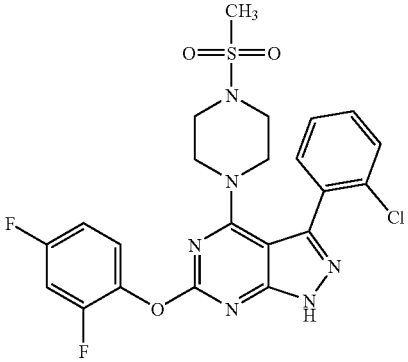 | 3-(2-Chloro-phenyl)-6-(2,4-difluoro-phenoxy)-4-(4-methanesulfonyl-piperazin-1-yl)-1H-pyrazolo[3,4-d]pyrimidine | 522 | 1 |

TABLE 1-continued

| # | Structure | Name (Autonom ™) | MP ° C. or M + H | Example |
|---|---|---|---|---|
| 49 | 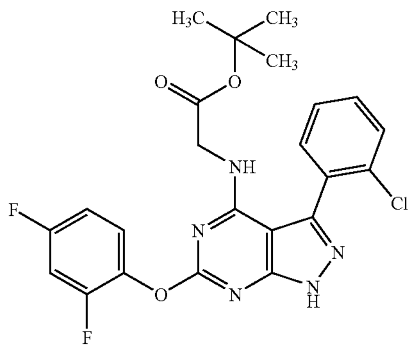 | [3-(2-Chloro-phenyl)-6-(2,4-difluoro-phenoxy)-1H-pyrazolo[3,4-d]pyrimidin-4-ylamino]-acetic acid tert-butyl ester | 489 | 1 |
| 50 | 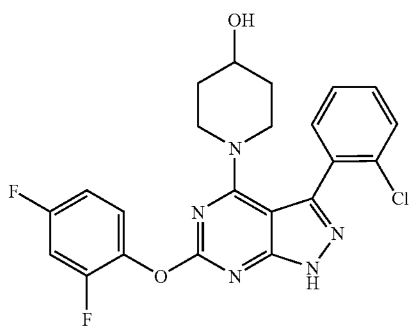 | 1-[3-(2-Chloro-phenyl)-6-(2,4-difluoro-phenoxy)-1H-pyrazolo[3,4-d]pyrimidin-4-yl]-piperidin-4-ol | 459 | 1 |
| 51 | 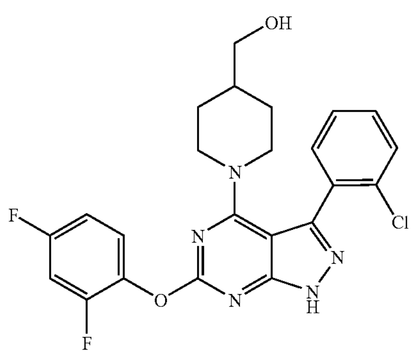 | {1-[3-(2-Chloro-phenyl)-6-(2,4-difluoro-phenoxy)-1H-pyrazolo[3,4-d]pyrimidin-4-yl]-piperidin-4-yl}-methanol | 473 | 1 |
| 52 | 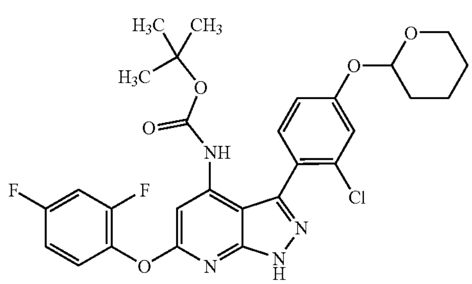 | [3-[2-Chloro-4-(tetrahydro-pyran-2-yloxy)-phenyl]-6-(2,4-difluoro-phenoxy)-1H-pyrazolo[3,4-b]pyridin-4-yl]-carbamic acid tert-butyl ester | 574 | 1 |

TABLE 1-continued

| # | Structure | Name (Autonom ™) | MP ° C. or M + H | Example |
|---|---|---|---|---|
| 53 | 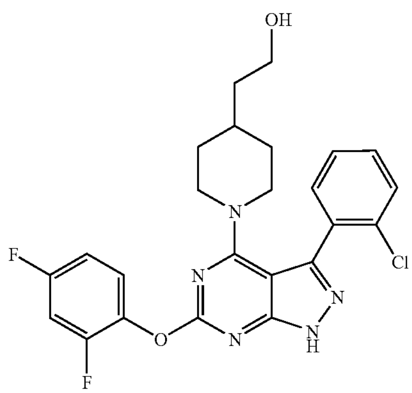 | 2-{1-[3-(2-Chloro-phenyl)-6-(2,4-difluoro-phenoxy)-1H-pyrazolo[3,4-d]pyrimidin-4-yl]-piperidin-4-yl}-ethanol | 487 | 1 |
| 54 | 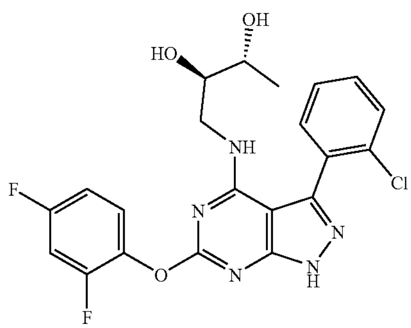 | 1-[3-(2-Chloro-phenyl)-6-(2,4-difluoro-phenoxy)-1H-pyrazolo[3,4-d]pyrimidin-4-ylamino]-butane-2,3-diol | 463 | 1 |
| 55 | 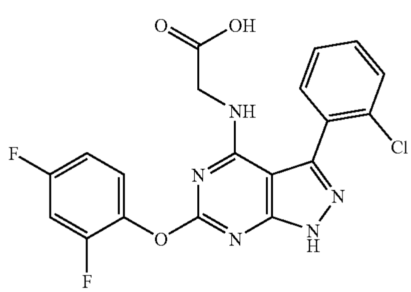 | [3-(2-Chloro-phenyl)-6-(2,4-difluoro-phenoxy)-1H-pyrazolo[3,4-d]pyrimidin-4-ylamino]-acetic acid | 433 | 1 |
| 56 | 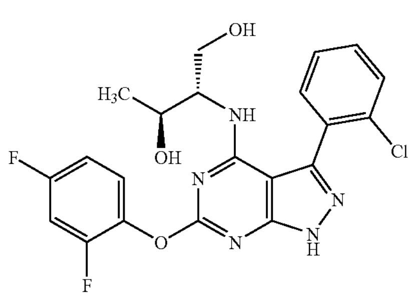 | 2-[3-(2-Chloro-phenyl)-6-(2,4-difluoro-phenoxy)-1H-pyrazolo[3,4-d]pyrimidin-4-ylamino]-butane-1,3-diol | 463 | 1 |

TABLE 1-continued

| # | Structure | Name (Autonom ™) | MP ° C. or M + H | Example |
|---|---|---|---|---|
| 57 | 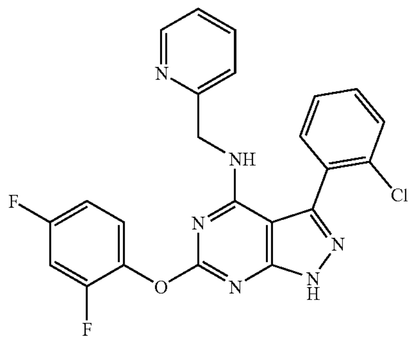 | [3-(2-Chloro-phenyl)-6-(2,4-difluoro-phenoxy)-1H-pyrazolo[3,4-d]pyrimidin-4-yl]-pyridin-2-ylmethyl-amine | 466 | 1 |
| 58 | 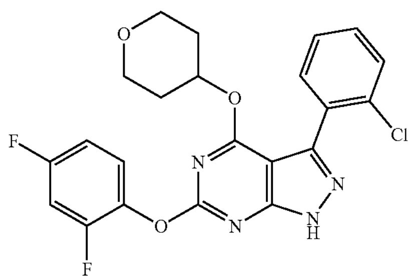 | 3-(2-Chloro-phenyl)-6-(2,4-difluoro-phenoxy)-4-(tetrahydro-pyran-4-yloxy)-1H-pyrazolo[3,4-d]pyrimidine | 460 | 5 |
| 59 | 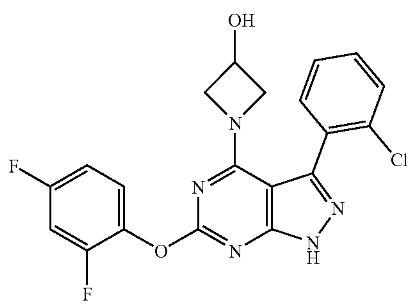 | 1-[3-(2-Chloro-phenyl)-6-(2,4-difluoro-phenoxy)-1H-pyrazolo[3,4-d]pyrimidin-4-yl]-azetidin-3-ol | 431 | 1 |
| 60 | 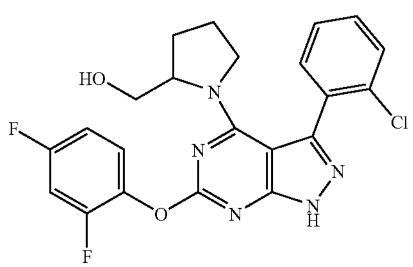 | {1-[3-(2-Chloro-phenyl)-6-(2,4-difluoro-phenoxy)-1H-pyrazolo[3,4-d]pyrimidin-4-yl]-pyrrolidin-2-yl}-methanol | 459 | 1 |
| 61 | 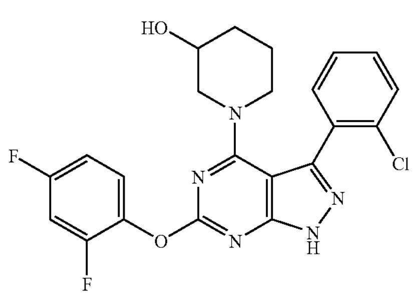 | 1-[3-(2-Chloro-phenyl)-6-(2,4-difluoro-phenoxy)-1H-pyrazolo[3,4-d]pyrimidin-4-yl]-piperidin-3-ol | 459 | 1 |

TABLE 1-continued

| # | Structure | Name (Autonom ™) | MP ° C. or M + H | Example |
|---|---|---|---|---|
| 62 | 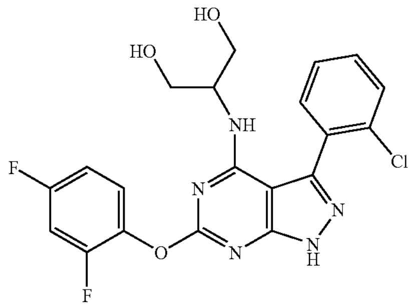 | 2-[3-(2-Chloro-phenyl)-6-(2,4-difluoro-phenoxy)-1H-pyrazolo[3,4-d]pyrimidin-4-ylamino]-propane-1,3-diol | 449 | 1 |
| 63 | 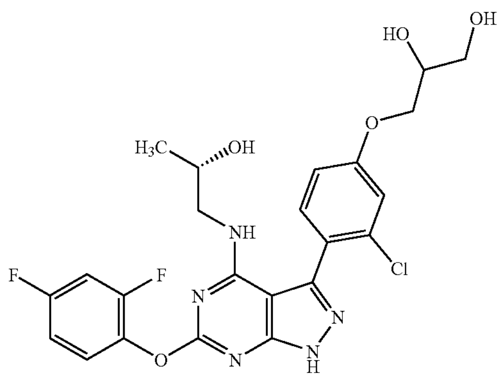 | 3-{3-Chloro-4-[6-(2,4-difluoro-phenoxy)-4-(2-hydroxy-propylamino)-1H-pyrazolo[3,4-d]pyrimidin-3-yl]-phenoxy}-propane-1,2-diol | 523 | 4 |
| 64 | 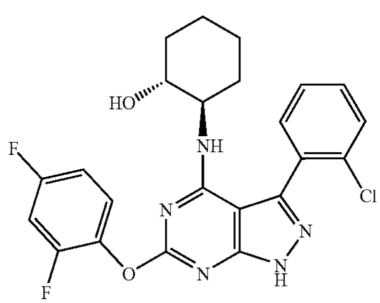 | 2-[3-(2-Chloro-phenyl)-6-(2,4-difluoro-phenoxy)-1H-pyrazolo[3,4-d]pyrimidin-4-ylamino]-cyclohexanol | 473 | 1 |
| 65 | 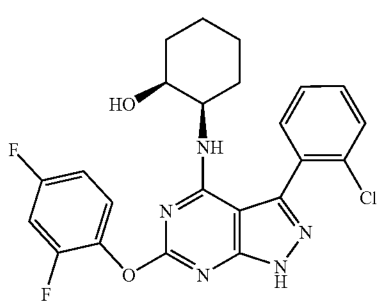 | 2-[3-(2-Chloro-phenyl)-6-(2,4-difluoro-phenoxy)-1H-pyrazolo[3,4-d]pyrimidin-4-ylamino]-cyclohexanol | 473 | 1 |
| 66 | 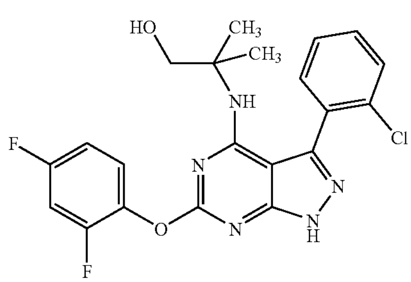 | 2-[3-(2-Chloro-phenyl)-6-(2,4-difluoro-phenoxy)-1H-pyrazolo[3,4-d]pyrimidin-4-ylamino]-2-methyl-propan-1-ol | 447 | 1 |

TABLE 1-continued

| # | Structure | Name (Autonom ™) | MP ° C. or M + H | Example |
|---|---|---|---|---|
| 67 | 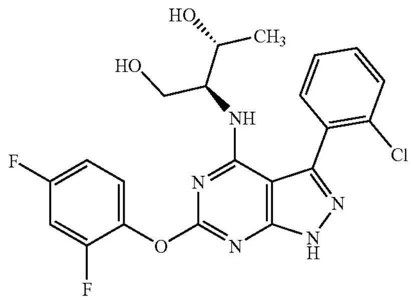 | 2-[3-(2-Chloro-phenyl)-6-(2,4-difluoro-phenoxy)-1H-pyrazolo[3,4-d]pyrimidin-4-ylamino]-butane-1,3-diol | 463 | 1 |
| 68 | 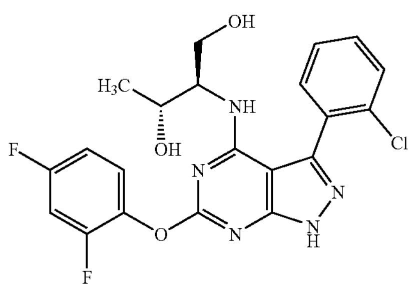 | 2-[3-(2-Chloro-phenyl)-6-(2,4-difluaro-phenoxy)-1H-pyrazolo[3,4-d]pyrimidin-4-ylamino]-butane-1,3-diol | 463 | 1 |
| 69 | 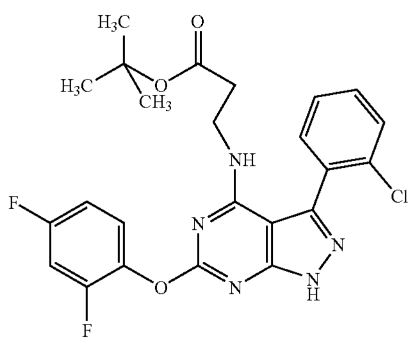 | 3-[3-(2-Chloro-phenyl)-6-(2,4-difluoro-phenoxy)-1H-pyrazolo[3,4-d]pyrimidin-4-ylamino]-propionic acid tert-butyl ester | 503 | 1 |
| 70 | 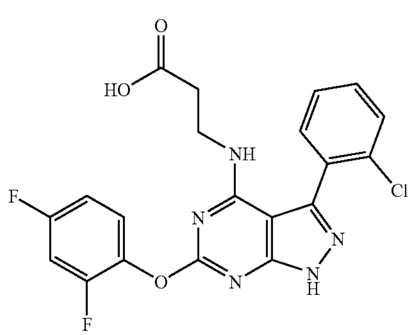 | 3-[3-(2-Chloro-phenyl)-6-(2,4-difluoro-phenoxy)-1H-pyrazolo[3,4-d]pyrimidin-4-ylamino]-propionic acid | 447 | 1 |

TABLE 1-continued

| # | Structure | Name (Autonom ™) | MP ° C. or M + H | Example |
|---|-----------|------------------|------------------|---------|
| 71 | 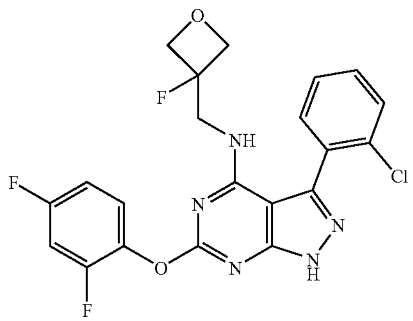 | [3-(2-Chloro-phenyl)-6-(2,4-difluoro-phenoxy)-1H-pyrazolo[3,4-d]pyrimidin-4-yl]-(3-fluoro-oxetan-3-ylmethyl)-amine | 463 | 1 |
| 72 | 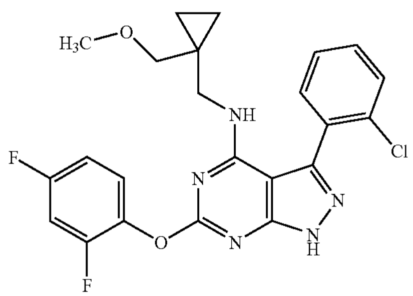 | [3-(2-Chloro-phenyl)-6-(2,4-difluoro-phenoxy)-1H-pyrazolo[3,4-d]pyrimidin-4-yl]-(1-methoxymethyl-cyclopropylmethyl)-amine | 473 | 1 |
| 73 | 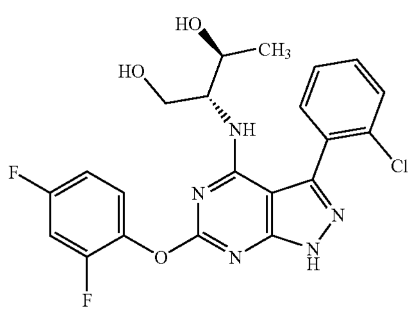 | 2-[3-(2-Chloro-phenyl)-6-(2,4-difluoro-phenoxy)-1H-pyrazolo[3,4-d]pyrimidin-4-ylamino]-butane-1,3-diol | 463 | 1 |
| 74 | 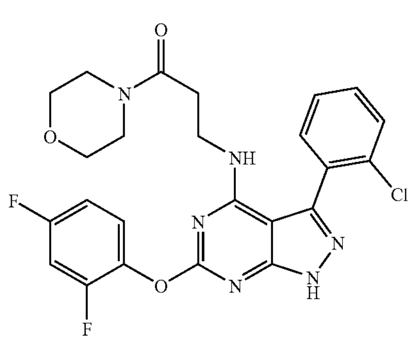 | 3-[3-(2-Chloro-phenyl)-6-(2,4-difluoro-phenoxy)-1H-pyrazolo[3,4-d]pyrimidin-4-ylamino]-1-morpholin-4-yl-propan-1-one | 516 | 1 |

TABLE 1-continued

| # | Structure | Name (Autonom ™) | MP ° C. or M + H | Example |
|---|---|---|---|---|
| 75 | 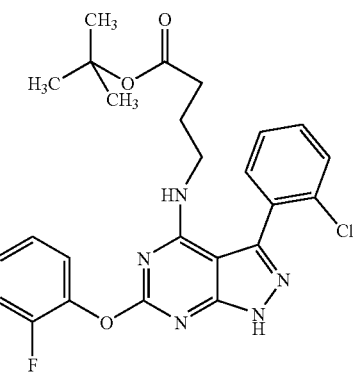 | 4-[3-(2-Chloro-phenyl)-6-(2,4-difluoro-phenoxy)-1H-pyrazolo[3,4-d]pyrimidin-4-ylamino]-butyric acid tert-butyl ester | 517 | 1 |
| 76 | 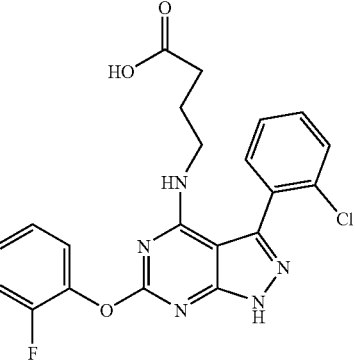 | 4-[3-(2-Chloro-phenyl)-6-(2,4-difluoro-phenoxy)-1H-pyrazolo[3,4-d]pyrimidin-4-ylamino]-butyric acid | 461 | 1 |
| 77 | 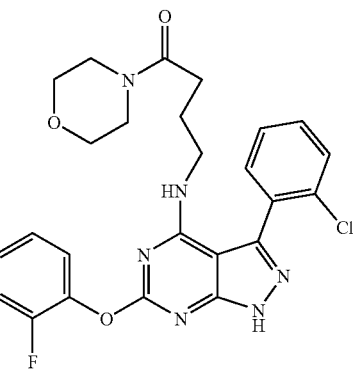 | 4-[3-(2-Chloro-phenyl)-6-(2,4-difluoro-phenoxy)-1H-pyrazolo[3,4-d]pyrimidin-4-ylamino]-1-morpholin-4-yl-butan-1-one | 530 | 1 |
| 78 | 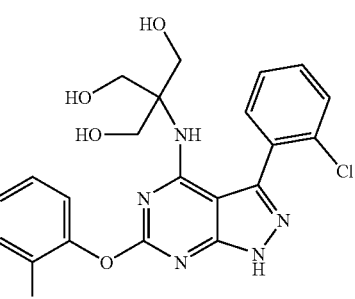 | 2-[3-(2-Chloro-phenyl)-6-(2,4-difluoro-phenoxy)-1H-pyrazolo[3,4-d]pyrimidin-4-ylamino]-2-hydroxymethyl-propane-1,3-diol | 479 | 1 |

TABLE 1-continued

| # | Structure | Name (Autonom ™) | MP ° C. or M + H | Example |
|---|---|---|---|---|
| 79 | 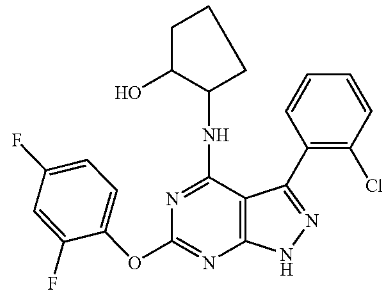 | 2-[3-(2-Chloro-phenyl)-6-(2,4-difluoro-phenoxy)-1H-pyrazolo[3,4-d]pyrimidin-4-ylamino]-cyclopentanol | 459 | 1 |
| 80 | 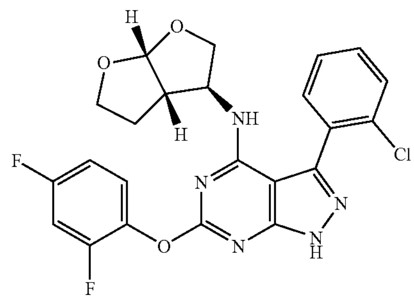 | [3-(2-Chloro-phenyl)-6-(2,4-difluoro-phenoxy)-1H-pyrazolo[3,4-d]pyrimidin-4-yl]-(hexahydro-furo[2,3-b]furan-3-yl)-amine | 487 | 1 |
| 81 | 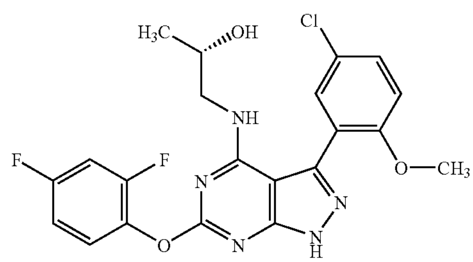 | 1-[3-(5-Chloro-2-methoxy-phenyl)-6-(2,4-difluoro-phenoxy)-1H-pyrazolo[3,4-d]pyrimidin-4-ylamino]-propan-2-ol | 463 | 4 |
| 82 | 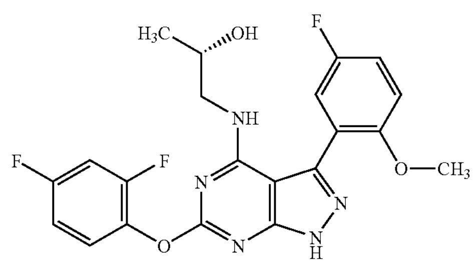 | 1-[6-(2,4-Difluoro-phenoxy)-3-(5-fluoro-2-methoxy-phenyl)-1H-pyrazolo[3,4-d]pyrimidin-4-ylamino]-propan-2-ol | 446 | 4 |
| 83 | 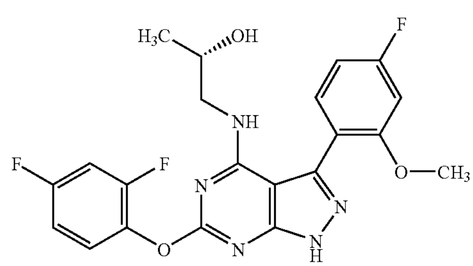 | 1-[6-(2,4-Difluoro-phenoxy)-3-(4-fluoro-2-methoxy-phenyl)-1H-pyrazolo[3,4-d]pyrimidin-4-ylamino]-propan-2-ol | 446 | 4 |

TABLE 1-continued

| # | Structure | Name (Autonom ™) | MP ° C. or M + H | Example |
|---|---|---|---|---|
| 84 | 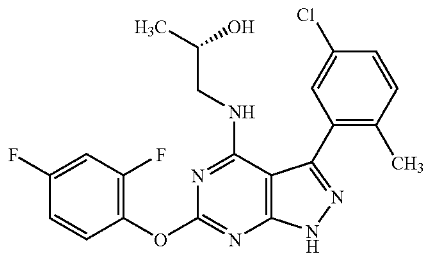 | 1-[3-(5-Chloro-2-methyl-phenyl)-6-(2,4-difluoro-phenoxy)-1H-pyrazolo[3,4-d]pyrimidin-4-ylamino]-propan-2-ol | 447 | 4 |
| 85 | 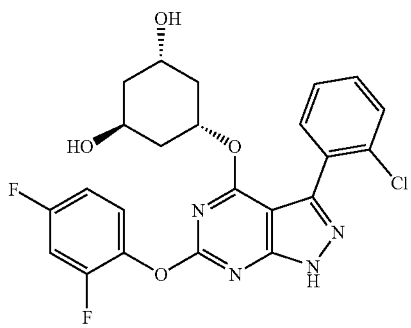 | 5-[3-(2-Chloro-phenyl)-6-(2,4-difluoro-phenoxy)-1H-pyrazolo[3,4-d]pyrimidin-4-yloxy]-cyclohexane-1,3-diol | 490 | 5 |
| 86 | 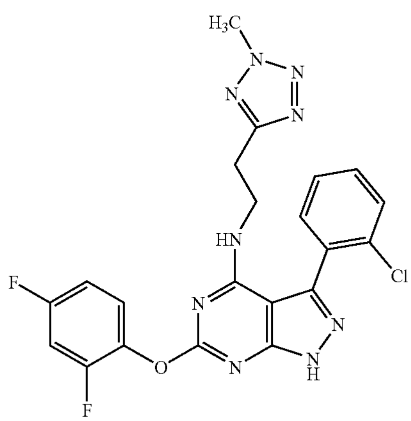 | [3-(2-Chloro-phenyl)-6-(2,4-difluoro-phenoxy)-1H-pyrazolo[3,4-d]pyrimidin-4-yl]-[2-(2-methyl-2H-tetrazol-5-yl)-ethyl]-amine | 485 | 1 |
| 87 | 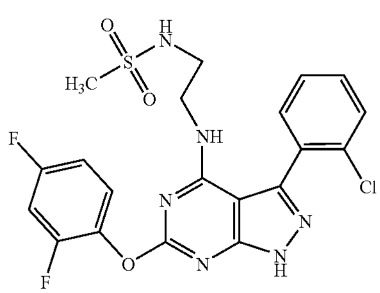 | N-{2-[3-(2-Chloro-phenyl)-6-(2,4-difluoro-phenoxy)-1H-pyrazolo[3,4-d]pyrimidin-4-ylamino]-ethyl}-methanesulfonamide | 496 | 1 |

TABLE 1-continued

| # | Structure | Name (Autonom ™) | MP ° C. or M + H | Example |
|---|---|---|---|---|
| 88 | 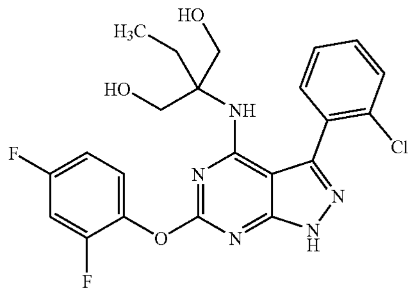 | 2-[3-(2-Chloro-phenyl)-6-(2,4-difluoro-phenoxy)-1H-pyrazolo[3,4-d]pyrimidin-4-ylamino]-2-ethyl-propane-1,3-diol | 477 | 1 |
| 89 | 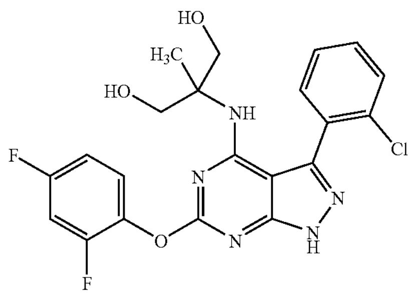 | 2-[3-(2-Chloro-phenyl)-6-(2,4-difluoro-phenoxy)-1H-pyrazolo[3,4-d]pyrimidin-4-ylamino]-2-methyl-propane-1,3-diol | 463 | 1 |
| 90 | 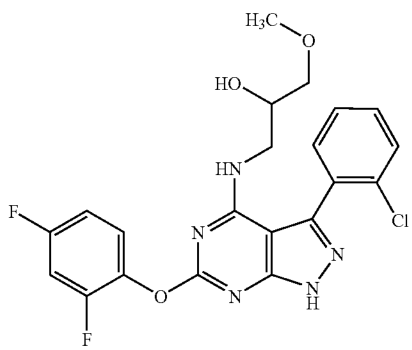 | 1-[3-(2-Chloro-phenyl)-6-(2,4-difluoro-phenoxy)-1H-pyrazolo[3,4-d]pyrimidin-4-ylamino]-3-methoxy-propan-2-ol | 463 | 1 |
| 91 | 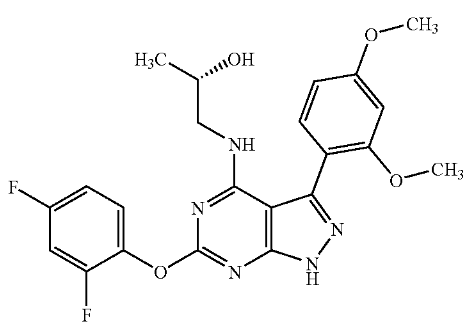 | 1-[6-(2,4-Difluoro-phenoxy)-3-(2,4-dimethoxy-phenyl)-1H-pyrazolo[3,4-d]pyrimidin-4-ylamino]-propan-2-ol | 458 | 4 |
| 92 | 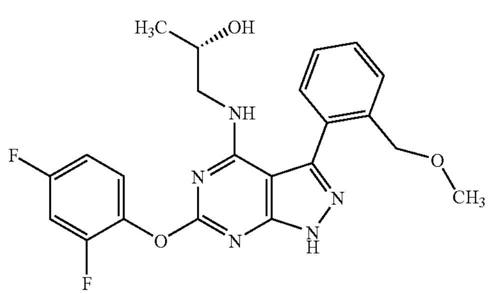 | 1-[6-(2,4-Difluoro-phenoxy)-3-(2-methoxymethyl-phenyl)-1H-pyrazolo[3,4-d]pyrimidin-4-ylamino]-propan-2-ol | 442 | 4 |

TABLE 1-continued

| # | Structure | Name (Autonom ™) | MP ° C. or M + H | Example |
|---|---|---|---|---|
| 93 | 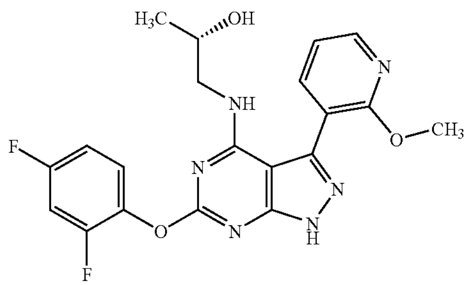 | 1-[6-(2,4-Difluoro-phenoxy)-3-(2-methoxy-pyridin-3-yl)-1H-pyrazolo[3,4-d]pyrimidin-4-ylamino]-propan-2-ol | 429 | 4 |
| 94 | 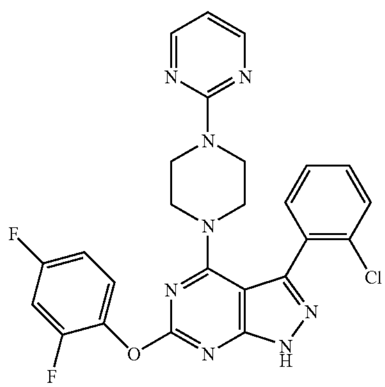 | 3-(2-Chloro-phenyl)-6-(2,4-difluoro-phenoxy)-4-(4-pyrimidin-2-yl-piperazin-1-yl)-1H-pyrazolo[3,4-d]pyrimidine | 522 | 1 |
| 95 | 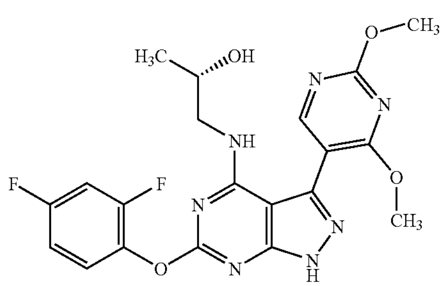 | 1-[6-(2,4-Difluoro-phenoxy)-3-(2,4-dimethoxy-pyrimidin-5-yl)-1H-pyrazolo[3,4-d]pyrimidin-4-ylamino]-propan-2-ol | 460 | 4 |
| 96 | 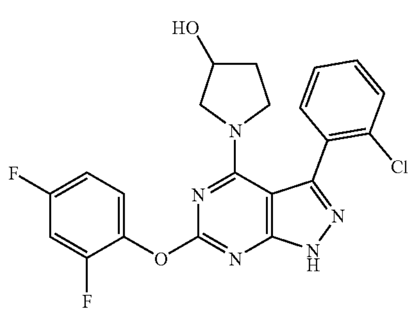 | 1-[3-(2-Chloro-phenyl)-6-(2,4-difluoro-phenoxy)-1H-pyrazolo[3,4-d]pyrimidin-4-yl]-pyrrolidin-3-ol | 445 | 1 |

TABLE 1-continued

| # | Structure | Name (Autonom ™) | MP ° C. or M + H | Example |
|---|---|---|---|---|
| 97 | 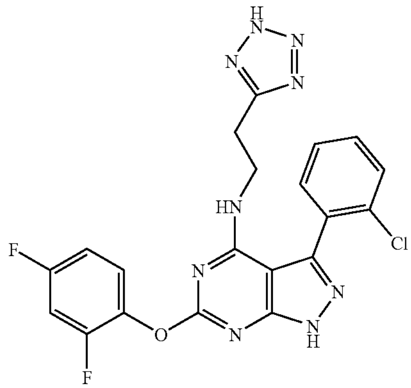 | [3-(2-Chloro-phenyl)-6-(2,4-difluoro-phenoxy)-1H-pyrazolo[3,4-d]pyrimidin-4-yl]-[2-(2H-tetrazol-5-yl)-ethyl]-amine | 471 | 1 |
| 98 | 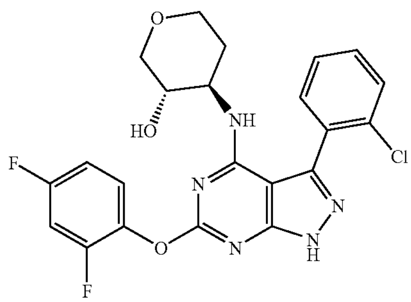 | 4-[3-(2-Chloro-phenyl)-6-(2,4-difluoro-phenoxy)-1H-pyrazolo[3,4-d]pyrimidin-4-ylamino]-tetrahydro-pyran-3-ol | 475 | 1 |
| 99 | 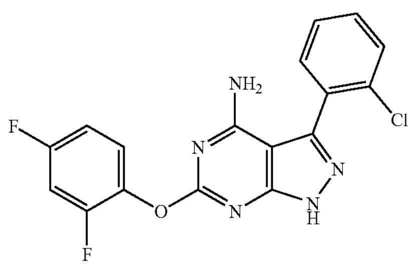 | 3-(2-Chloro-phenyl)-6-(2,4-difluoro-phenoxy)-1H-pyrazolo[3,4-d]pyrimidin-4-ylamine | 375 | 3 |
| 100 | 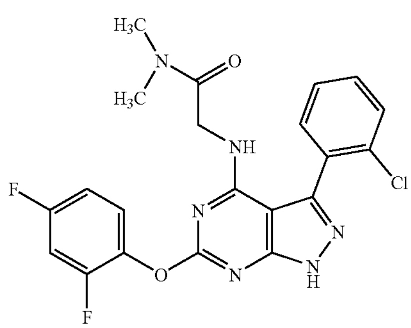 | 2-[3-(2-Chloro-phenyl)-6-(2,4-difluoro-phenoxy)-1H-pyrazolo[3,4-d]pyrimidin-4-ylamino]-N,N-dimethyl-acetamide | 460 | 1 |
| 101 | 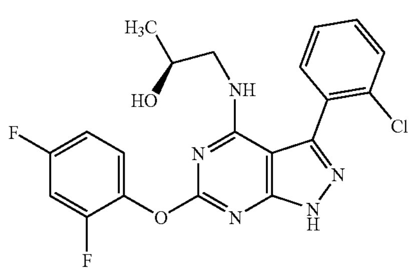 | 1-[3-(2-Chloro-phenyl)-6-(2,4-difluoro-phenoxy)-1H-pyrazolo[3,4-b]pyridin-4-ylamino]-propan-2-ol | 432 | 1 |

TABLE 1-continued

| # | Structure | Name (Autonom ™) | MP ° C. or M + H | Example |
|---|---|---|---|---|
| 102 | 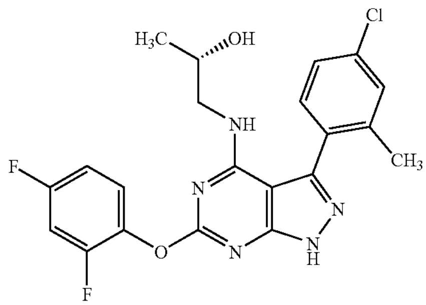 | 1-[3-(4-Chloro-2-methyl-phenyl)-6-(2,4-difluoro-phenoxy)-1H-pyrazolo[3,4-d]pyrimidin-4-ylamino]-propan-2-ol | 447 | 1 |
| 103 | 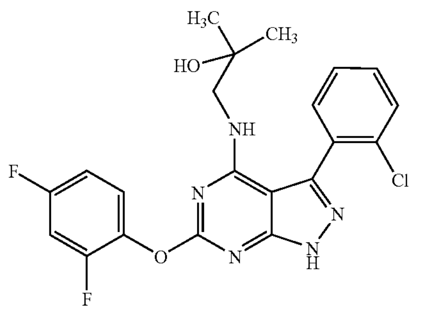 | 1-[3-(2-Chloro-phenyl)-6-(2,4-difluoro-phenoxy)-1H-pyrazolo[3,4-d]pyrimidin-4-ylamino]-2-methyl-propan-2-ol | 447 | 1 |
| 104 | 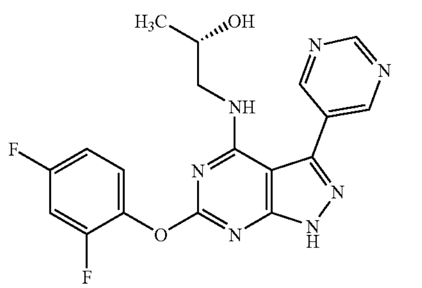 | 1-[6-(2,4-Difluoro-phenoxy)-3-pyrimidin-5-yl-1H-pyrazolo[3,4-d]pyrimidin-4-ylamino]-propan-2-ol | 400 | 4 |
| 105 | 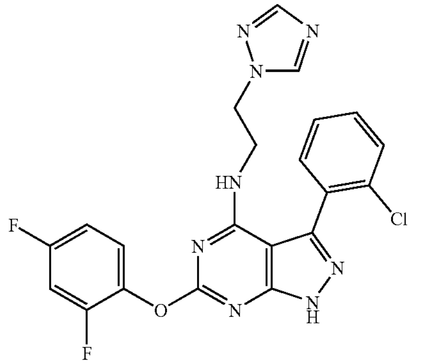 | [3-(2-Chloro-phenyl)-6-(2,4-difluoro-phenoxy)-1H-pyrazolo[3,4-d]pyrimidin-4-yl]-(2-[1,2,4]triazol-1-yl-ethyl)-amine | 470 | 1 |

TABLE 1-continued

| # | Structure | Name (Autonom ™) | MP ° C. or M + H | Example |
|---|---|---|---|---|
| 106 | 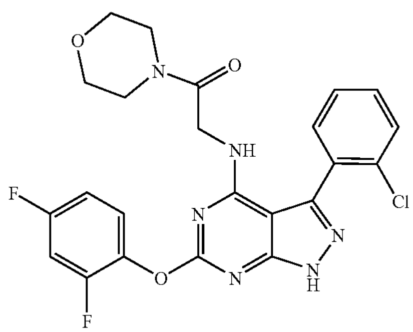 | 2-[3-(2-Chloro-phenyl)-6-(2,4-difluoro-phenoxy)-1H-pyrazolo[3,4-d]pyrimidin-4-ylamino]-1-morpholin-4-yl-ethanone | 502 | 1 |
| 107 | 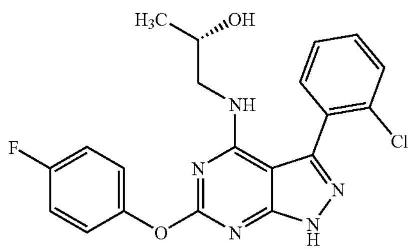 | 1-[3-(2-Chloro-phenyl)-6-(4-fluoro-phenoxy)-1H-pyrazolo[3,4-d]pyrimidin-4-ylamino]-propan-2-ol | 415 | 1 |
| 108 | 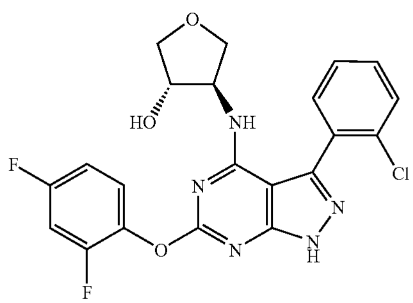 | 4-[3-(2-Chloro-phenyl)-6-(2,4-difluoro-phenoxy)-1H-pyrazolo[3,4-d]pyrimidin-4-ylamino]-tetrahydro-furan-3-ol | 461 | 1 |
| 109 | 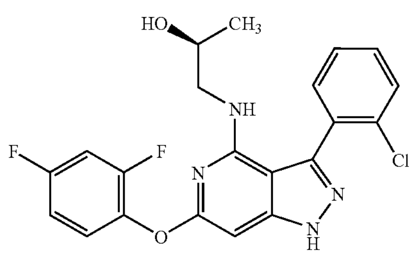 | 1-[3-(2-Chloro-phenyl)-6-(2,4-difluoro-phenoxy)-1H-pyrazolo[4,3-c]pyridin-4-ylamino]-propan-2-ol | 432 | 9 |
| 110 | 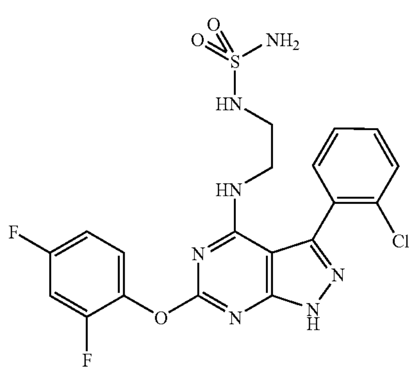 | 1-[3-(2-Chloro-phenyl)-6-(4-fluoro-phenoxy)-1H-pyrazolo[3,4-d]pyrimidin-4-ylamino]-aminosulfonyl ethylamine | 497 | 1 |

TABLE 1-continued

| # | Structure | Name (Autonom ™) | MP ° C. or M + H | Example |
|---|---|---|---|---|
| 111 | 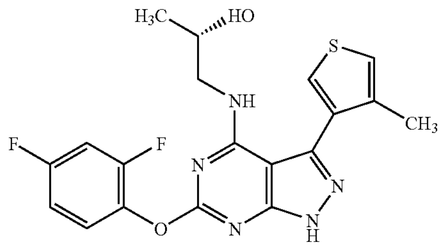 | 1-[6-(2,4-Difluoro-phenoxy)-3-(4-methyl-thiophen-3-yl)-1H-pyrazolo[3,4-d]pyrimidin-4-ylamino]-propan-2-ol | 418 | 4 |
| 112 | 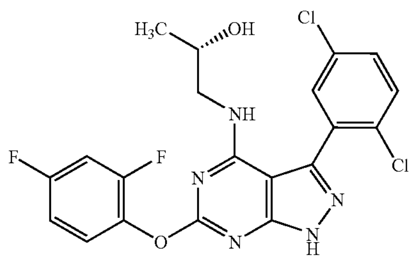 | 1-[3-(2,5-Dichloro-phenyl)-6-(2,4-difluoro-phenoxy)-1H-pyrazolo[3,4-d]pyrimidin-4-ylamino]-propan-2-ol | 467 | 4 |
| 113 | 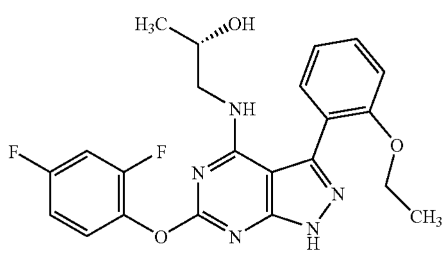 | 1-[6-(2,4-Difluoro-phenoxy)-3-(2-ethoxy-phenyl)-1H-pyrazolo[3,4-d]pyrimidin-4-ylamino]-propan-2-ol | 442 | 4 |
| 114 | 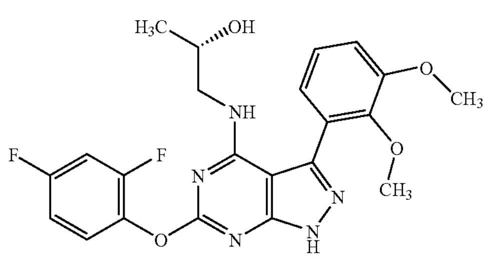 | 1-[6-(2,4-Difluoro-phenoxy)-3-(2,3-dimethoxy-phenyl)-1H-pyrazolo[3,4-d]pyrimidin-4-ylamino]-propan-2-ol | 458 | 4 |
| 115 | 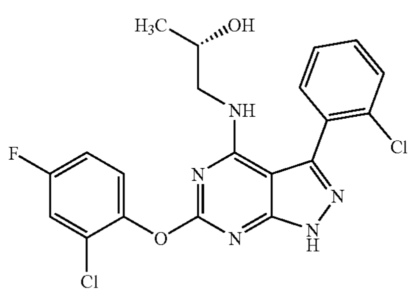 | 1-[6-(2-Chloro-4-fluoro-phenoxy)-3-(2-chloro-phenyl)-1H-pyrazolo[3,4-d]pyrimidin-4-ylamino]-propan-2-ol | 449 | 1 |

TABLE 1-continued

| # | Structure | Name (Autonom ™) | MP ° C. or M + H | Example |
|---|---|---|---|---|
| 116 | 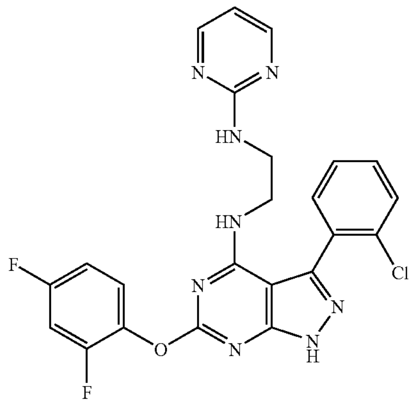 | N-[3-(2-Chloro-phenyl)-6-(2,4-difluoro-phenoxy)-1H-pyrazolo[3,4-d]pyrimidin-4-yl]-N'-pyrimidin-2-yl-ethane-1,2-diamine | 496 | 1 |
| 117 | 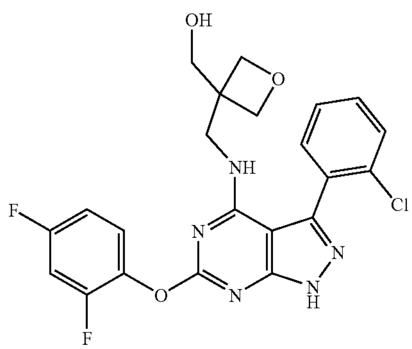 | (3-{[3-(2-Chloro-phenyl)-6-(2,4-difluoro-phenoxy)-1H-pyrazolo[3,4-d]pyrimidin-4-ylamino]-methyl}-oxetan-3-yl)-methanol | 475 | 1 |
| 118 | 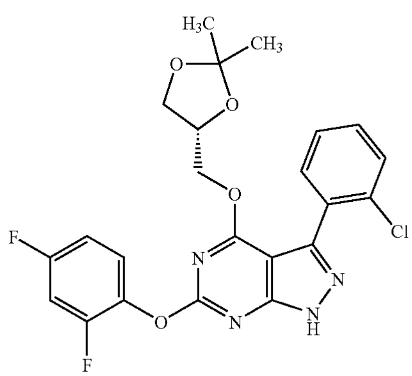 | 3-(2-Chloro-phenyl)-6-(2,4-difluoro-phenoxy)-4-(2,2-dimethyl-[1,3]dioxolan-4-ylmethoxy)-1H-pyrazolo[3,4-d]pyrimidine | 490 | 5 |
| 119 | 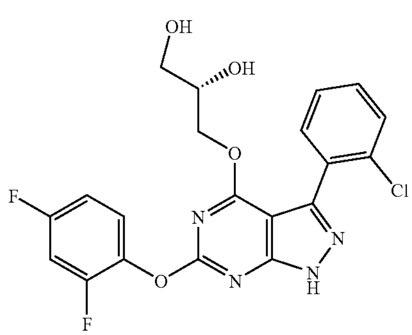 | 3-[3-(2-Chloro-phenyl)-6-(2,4-difluoro-phenoxy)-1H-pyrazolo[3,4-d]pyrimidin-4-yloxy]-propane-1,2-diol | 450 | 5 |

TABLE 1-continued

| # | Structure | Name (Autonom ™) | MP ° C. or M + H | Example |
|---|---|---|---|---|
| 120 | 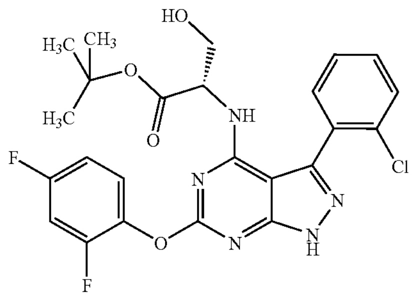 | 2-[3-(2-Chloro-phenyl)-6-(2,4-difluoro-phenoxy)-1H-pyrazolo[3,4-d]pyrimidin-4-ylamino]-3-hydroxy-propionic acid tert-butyl ester | 519 | 1 |
| 121 | 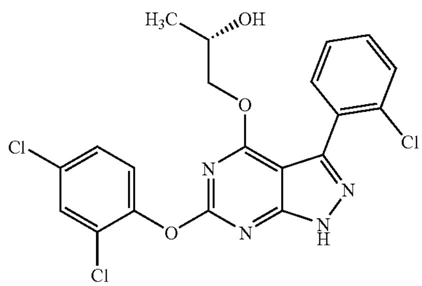 | 1-[3-(2-Chloro-phenyl)-6-(2,4-dichloro-phenoxy)-pyrazolo[3,4-d]pyrimidin-4-ylamino]-propan-2-ol | 466 | 1 |
| 122 | 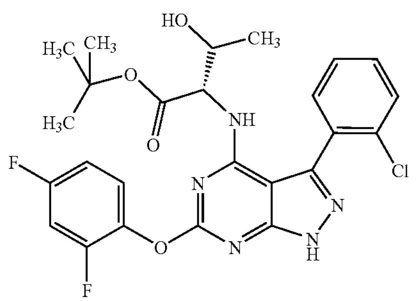 | 2-[3-(2-Chloro-phenyl)-6-(2,4-difluoro-phenoxy)-1H-pyrazolo[3,4-d]pyrimidin-4-ylamino]-3-hydroxy-butyric acid tert-butyl ester | 533 | 1 |
| 123 | 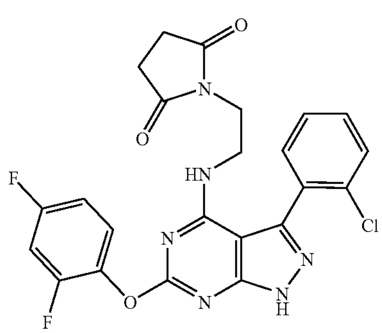 | 1-{2-[3-(2-Chloro-phenyl)-6-(2,4-difluoro-phenoxy)-1H-pyrazolo[3,4-d]pyrimidin-4-ylamino]-ethyl}-pyrrolidine-2,5-dione | 500 | 1 |
| 124 | 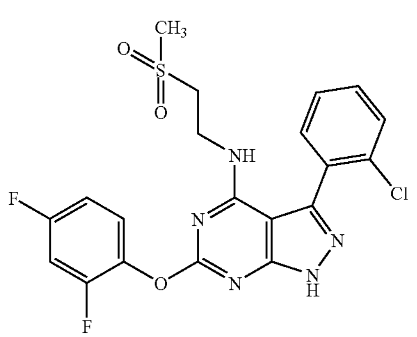 | [3-(2-Chloro-phenyl)-6-(2,4-difluoro-phenoxy)-1H-pyrazolo[3,4-d]pyrimidin-4-yl]-(2-methanesulfonyl-ethyl)-amine | 481 | 1 |

TABLE 1-continued

| # | Structure | Name (Autonom ™) | MP ° C. or M + H | Example |
|---|---|---|---|---|
| 125 | 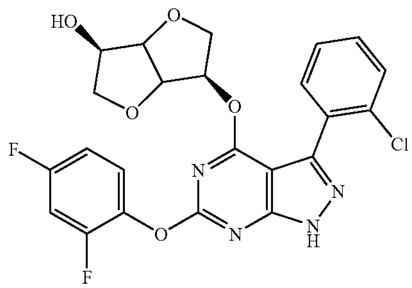 | 6-[3-(2-Chloro-phenyl)-6-(2,4-difluoro-phenoxy)-1H-pyrazolo[3,4-d]pyrimidin-4-yloxy]-hexahydro-furo[3,2-b]-firan-3-ol | 504 | 5 |
| 126 | 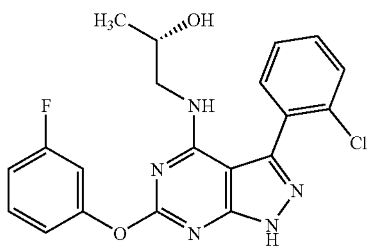 | 1-[3-(2-Chloro-phenyl)-6-(3-fluoro-phenoxy)-1H-pyrazolo[3,4-d]pyrimidin-4-ylamino]-propan-2-ol | 415 | 1 |
| 127 | 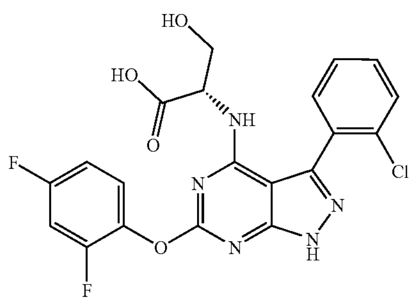 | 2-[3-(2-Chloro-phenyl)-6-(2,4-difluoro-phenoxy)-1H-pyrazolo[3,4-d]pyrimidin-4-ylamino]-3-hydroxy-propionic acid | 463 | 1 |
| 128 | 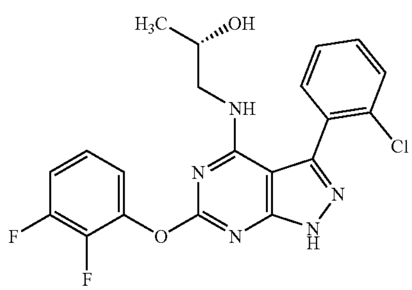 | 1-[3-(2-Chloro-phenyl)-6-(2,3-difluoro-phenoxy)-1H-pyrazolo[3,4-d]pyrimidin-4-ylamino]-propan-2-ol | 433 | 1 |
| 129 | 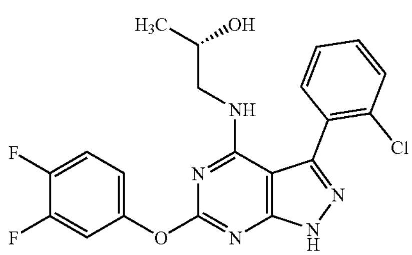 | 1-[3-(2-Chloro-phenyl)-6-(3,4-difluoro-phenoxy)-1H-pyrazolo[3,4-d]pyrimidin-4-ylamino]-propan-2-ol | 433 | 1 |

TABLE 1-continued

| # | Structure | Name (Autonom ™) | MP ° C. or M + H | Example |
|---|---|---|---|---|
| 130 | 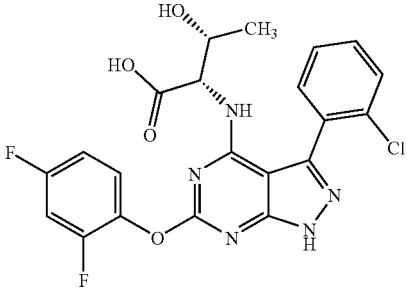 | 2-[3-(2-Chloro-phenyl)-6-(2,4-difluoro-phenoxy)-1H-pyrazolo[3,4-d]pyrimidin-4-ylamino]-3-hydroxy-butyric acid | 477 | 1 |
| 131 | 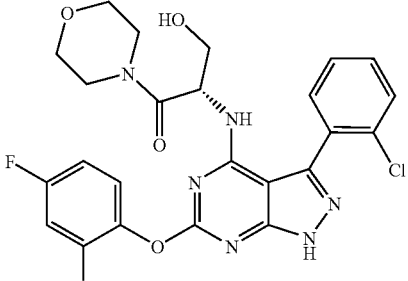 | 2-[3-(2-Chloro-phenyl)-6-(2,4-difluoro-phenoxy)-1H-pyrazolo[3,4-d]pyrimidin-4-ylamino]-3-hydroxy-1-morpholin-4-yl-propan-1-one | 532 | 1 |
| 132 | 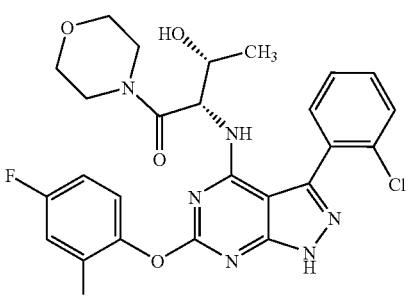 | 2-[3-(2-Chloro-phenyl)-6-(2,4-difluoro-phenoxy)-1H-pyrazolo[3,4-d]pyrimidin-4-ylamino]-3-hydroxy-1-morpholin-4-yl-butan-1-one | 556 | 1 |
| 133 | 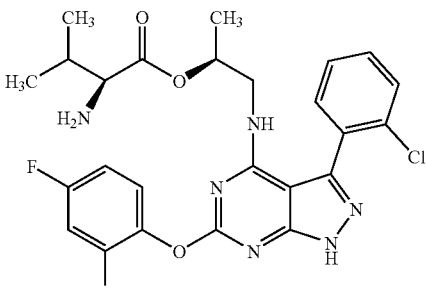 | 2-Amino-3-methyl-butyric acid 2-[3-(2-chloro-phenyl)-6-(2,4-difluoro-phenoxy)-1H-pyrazolo[3,4-d]pyrimidin-4-ylamino]-1-methyl-ethyl ester | 532 | 1 |
| 134 | 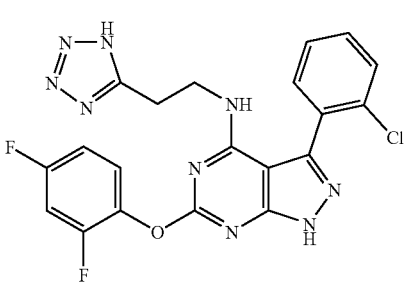 | [3-(2-Chloro-phenyl)-6-(2,4-difluoro-phenoxy)-1H-pyrazolo[3,4-d]pyrimidin-4-yl]-[2-(1H-tetrazol-5-yl)-ethyl]-amine | 471 | 1 |

TABLE 1-continued

| # | Structure | Name (Autonom ™) | MP ° C. or M + H | Example |
|---|---|---|---|---|
| 135 | 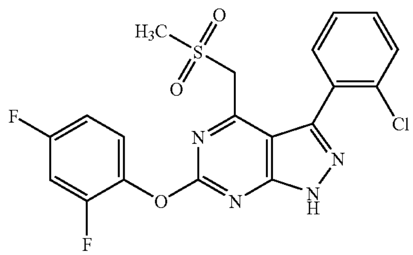 | 3-(2-Chloro-phenyl)-6-(2,4-difluoro-phenoxy)-4-methanesulfonylmethyl-1H-pyrazolo[3,4-d]pyrimidine | 452 | 6 |
| 136 | 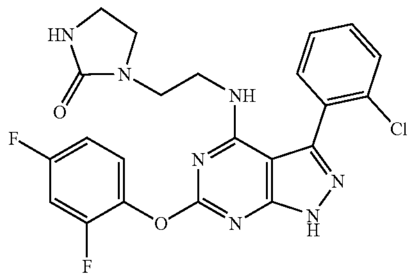 | 1-{2-[3-(2-Chloro-phenyl)-6-(2,4-difluoro-phenoxy)-1H-pyrazolo[3,4-d]pyrimidin-4-ylamino]-ethyl}-imidazolidin-2-one | 487 | 1 |
| 137 | 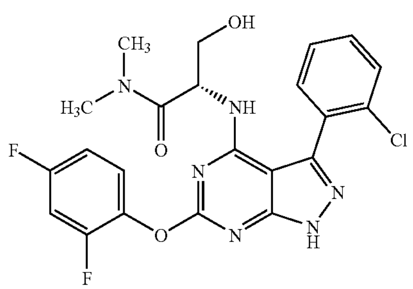 | 2-[3-(2-Chloro-phenyl)-6-(2,4-difluoro-phenoxy)-1H-pyrazolo[3,4-d]pyrimidin-4-ylamino]-3-hydroxy-N,N-dimethyl-propionamide | 490 | 1 |
| 138 | 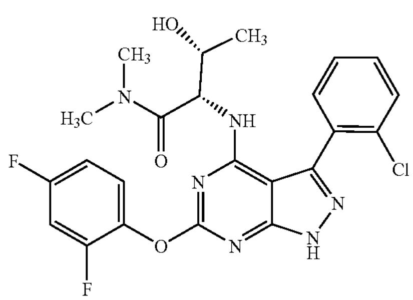 | 2-[3-(2-Chloro-phenyl)-6-(2,4-difluoro-phenoxy)-1H-pyrazolo[3,4-d]pyrimidin-4-ylamino]-3-hydroxy-N,N-dimethyl-butyramide | 504 | 1 |
| 139 | 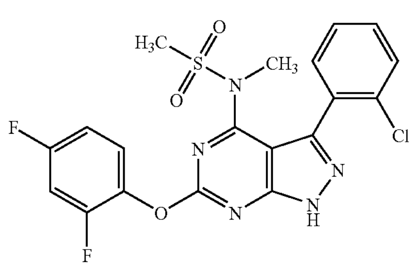 | N-[3-(2-Chloro-phenyl)-6-(2,4-difluoro-phenoxy)-1H-pyrazolo[3,4-d]pyrimidin-4-yl]-N-methyl-methanesulfonamide | 467 | 1 |

TABLE 1-continued

| # | Structure | Name (Autonom ™) | MP ° C. or M + H | Example |
|---|---|---|---|---|
| 140 | 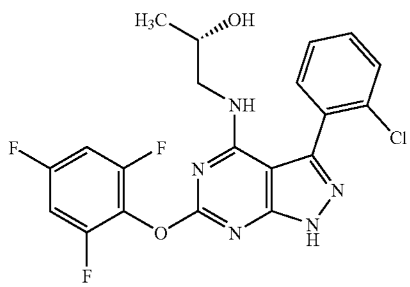 | 1-[3-(2-Chloro-phenyl)-6-(2,4,6-trifluoro-phenoxy)-1H-pyrazolo[3,4-d]pyrimidin-4-ylamino]-propan-2-ol | 451 | 1 |
| 141 | 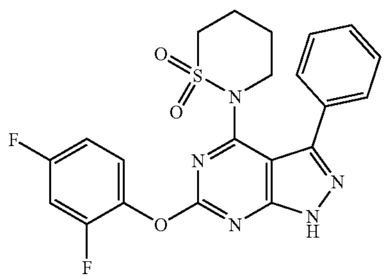 | 6-(2,4-Difluoro-phenoxy)-4-(1,1-dioxo-1lambda*6*-[1,2]thiazinan-2-yl)-3-phenyl-1H-pyrazolo[3,4-d]pyrimidine | 458 | 4 |
| 142 | 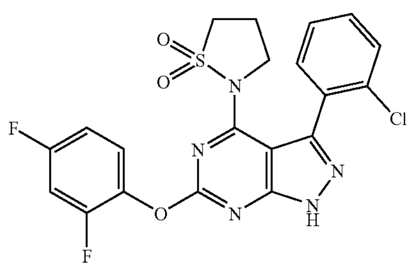 | 3-(2-Chloro-phenyl)-6-(2,4-difluoro-phenoxy)-4-(1,1-dioxo-1lambda*6*-isothiazolidin-2-yl)-1H-pyrazolo[3,4-d]pyrimidine | 479 | 1 |
| 143 | 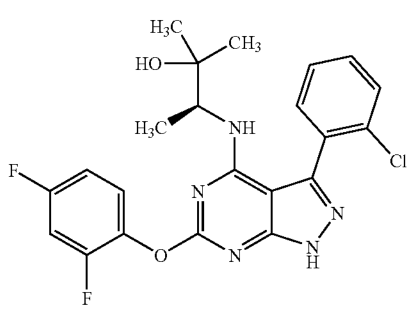 | 3-[3-(2-Chloro-phenyl)-6-(2,4-difluoro-phenoxy)-1H-pyrazolo[3,4-d]pyrimidin-4-ylamino]-2-methyl-butan-2-ol | 461 | 1 |
| 144 | 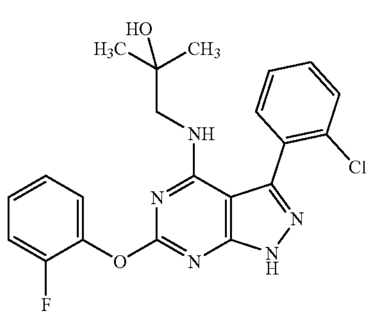 | 1-[3-(2-Chloro-phenyl)-6-(2-fluoro-phenoxy)-1H-pyrazolo[3,4-d]pyrimidin-4-ylamino]-2-methyl-propan-2-ol | 429 | 1 |

TABLE 1-continued

| # | Structure | Name (Autonom ™) | MP ° C. or M + H | Example |
|---|---|---|---|---|
| 145 | 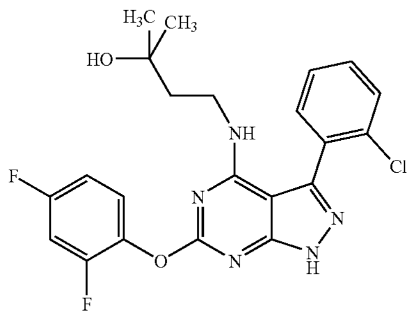 | 4-[3-(2-Chloro-phenyl)-6-(2,4-difluoro-phenoxy)-1H-pyrazolo[3,4-d]pyrimidin-4-ylamino]-2-methyl-butan-2-ol | 461 | 1 |
| 146 | 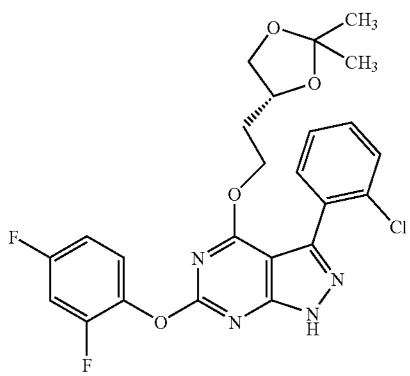 | 3-(2-Chloro-phenyl)-6-(2,4-difluoro-phenoxy)-4-[2-(2,2-dimethyl-[1,3]dioxolan-4-yl)-ethoxy]-1H-pyrazolo[3,4-d]pyrimidine | 504 | 5 |
| 147 | 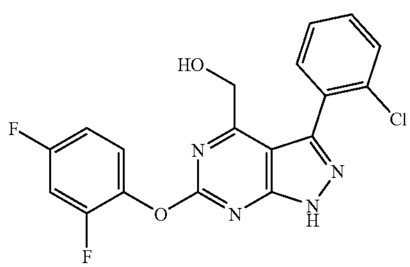 | [3-(2-Chloro-phenyl)-6-(2,4-difluoro-phenoxy)-1H-pyrazolo[3,4-d]pyrimidin-4-yl]-methanol | 390 | 6 |
| 148 | 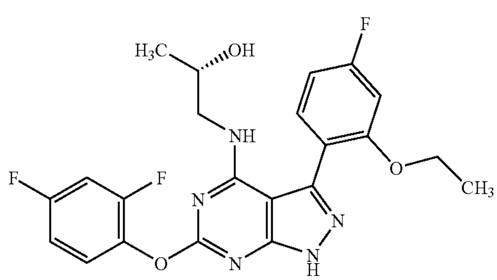 | 1-[6-(2,4-Difluoro-phenoxy)-3-(2-ethoxy-4-fluoro-phenyl)-1H-pyrazolo[3,4-d]pyrimidin-4-ylamino]-propan-2-ol | 460 | 4 |
| 149 | 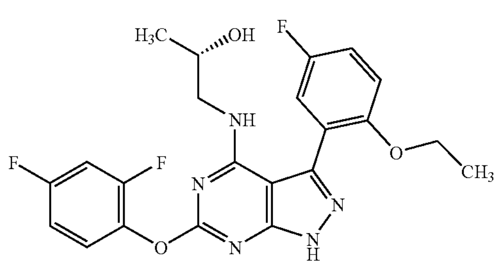 | 1-[6-(2,4-Difluoro-phenoxy)-3-(2-ethoxy-5-fluoro-phenyl)-1H-pyrazolo[3,4-d]pyrimidin-4-ylamino]-propan-2-ol | 460 | 4 |

TABLE 1-continued

| # | Structure | Name (Autonom ™) | MP ° C. or M + H | Example |
|---|---|---|---|---|
| 150 | 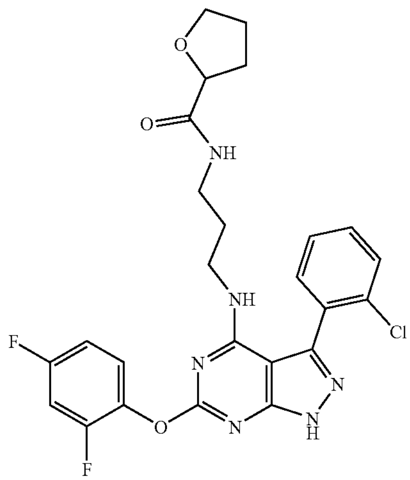 | Tetrahydro-furan-2-carboxylic acid {3-[3-(2-chloro-phenyl)-6-(2,4-difluoro-phenoxy)-1H-pyrazolo[3,4-d]pyrimidin-4-ylamino]-propyl}-amide | 530 | 1 |
| 151 | 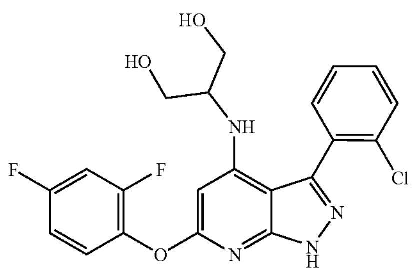 | 2-[3-(2-Chloro-phenyl)-6-(2,4-difluoro-phenoxy)-1H-pyrazolo[3,4-b]pyridin-4-ylamino]-propane-1,3-diol | 448 | 1 |
| 152 | 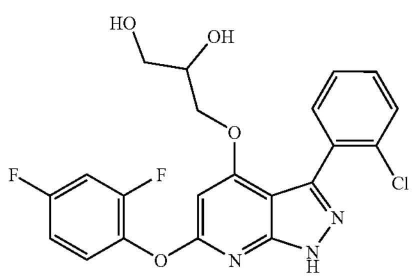 | 3-[3-(2-Chloro-phenyl)-6-(2,4-difluoro-phenoxy)-1H-pyrazolo[3,4-b]pyridin-4-yloxy]-propane-1,2-diol | 449 | 5 |
| 153 | 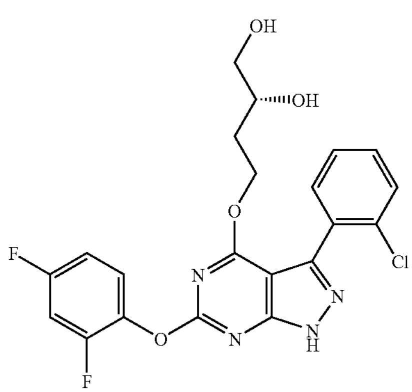 | 4-[3-(2-Chloro-phenyl)-6-(2,4-difluoro-phenoxy)-1H-pyrazolo[3,4-d]pyrimidin-4-yloxy]-butane-1,2-diol | 464 | 5 |

TABLE 1-continued

| # | Structure | Name (Autonom ™) | MP ° C. or M + H | Example |
|---|---|---|---|---|
| 154 | 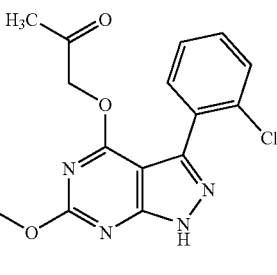 | 1-[3-(2-Chloro-phenyl)-6-(2,4-difluoro-phenoxy)-1H-pyrazolo[3,4-d]pyrimidin-4-yloxy]-propan-2-one | 432 | 5 |
| 155 | 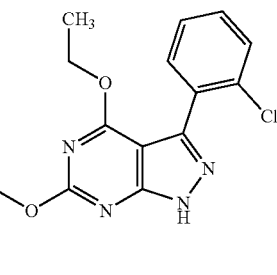 | 3-(2-Chloro-phenyl)-6-(2,4-difluoro-phenoxy)-4-ethoxy-1H-pyrazolo[3,4-d]pyrimidine | 404 | 5 |
| 156 | 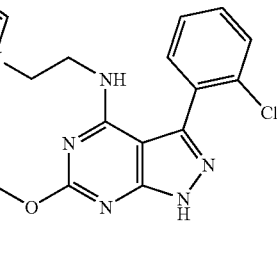 | [3-(2-Chloro-phenyl)-6-(2,4-difluoro-phenoxy)-1H-pyrazolo[3,4-d]pyrimidin-4-yl]-[2-(2-methyl-imidazol-1-yl)-ethyl]-amine | 483 | 1 |
| 157 | 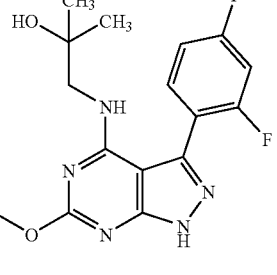 | 1-[6-(2,4-Difluoro-phenoxy)-3-(2,4-difluoro-phenyl)-1H-pyrazolo[3,4-d]pyrimidin-4-ylamino]-2-methyl-propan-2-ol | 448 | 4 |
| 158 | 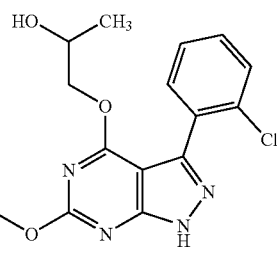 | 1-[3-(2-Chloro-phenyl)-6-(2,4-difluoro-phenoxy)-1H-pyrazolo[3,4-d]pyrimidin-4-yloxy]-propan-2-ol | 434 | 5 |

TABLE 1-continued

| # | Structure | Name (Autonom ™) | MP ° C. or M + H | Example |
|---|---|---|---|---|
| 159 | 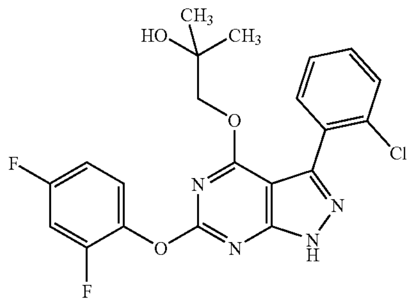 | 1-[3-(2-Chloro-phenyl)-6-(2,4-difluoro-phenoxy)-1H-pyrazolo[3,4-d]pyrimidin-4-yloxy]-2-methyl-propan-2-ol | 448 | 5 |
| 160 | 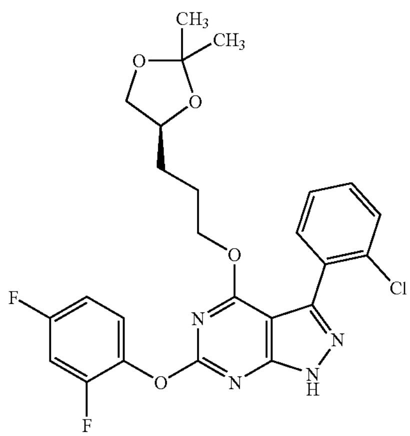 | 3-(2-Chloro-phenyl)-6-(2,4-difluoro-phenoxy)-4-[3-(2,2-dimethyl-[1,3]dioxolan-4-yl)-propoxy]-1H-pyrazolo[3,4-d]pyrimidine | 518 | 5 |
| 161 | 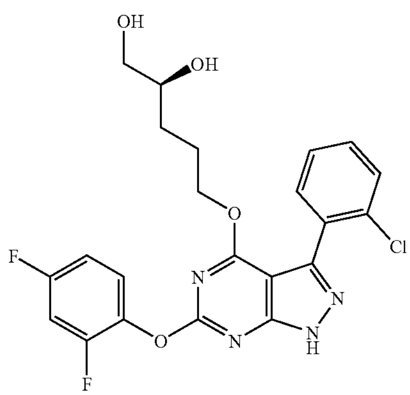 | 5-[3-(2-Chloro-phenyl)-6-(2,4-difluoro-phenoxy)-1H-pyrazolo[3,4-d]pyrimidin-4-yloxy]-pentane-1,2-diol | 478 | 5 |
| 162 | 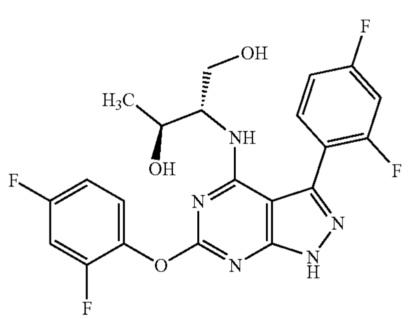 | 2-[6-(2,4-Difluoro-phenoxy)-3-(2,4-difluoro-phenyl)-1H-pyrazolo[3,4-d]pyrimidin-4-ylamino]-butane-1,3-diol | 464 | 4 |

TABLE 1-continued

| # | Structure | Name (Autonom™) | MP °C. or M + H | Example |
|---|---|---|---|---|
| 163 | 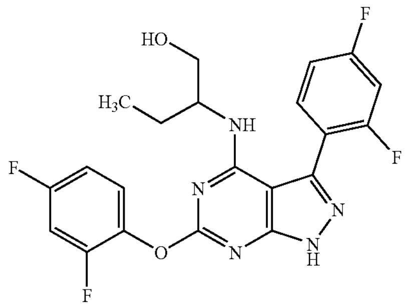 | 2-[6-(2,4-Difluoro-phenoxy)-3-(2,4-difluoro-phenyl)-1H-pyrazolo[3,4-d]pyrimidin-4-ylamino]-propane-1,3-diol | 450 | 4 |
| 164 | 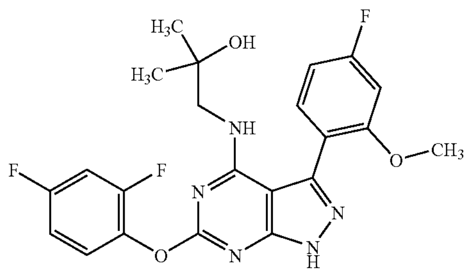 | 1-[6-(2,4-Difluoro-phenoxy)-3-(4-fluoro-2-methoxy-phenyl)-1H-pyrazolo[3,4-d]pyrimidin-4-ylamino]-2-methyl-propan-2-ol | 460 | 4 |
| 165 | 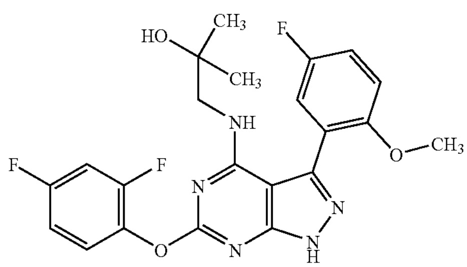 | 1-[6-(2,4-Difluoro-phenoxy)-3-(5-fluoro-2-methoxy-phenyl)-1H-pyrazolo[3,4-d]pyrimidin-4-ylamino]-2-methyl-propan-2-ol | 460 | 4 |
| 166 | 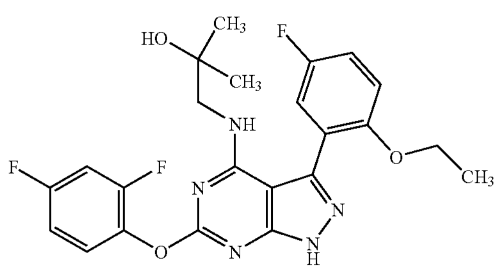 | 1-[6-(2,4-Difluoro-phenoxy)-3-(2-ethoxy-5-fluoro-phenyl)-1H-pyrazolo[3,4-d]pyrimidin-4-ylamino]-2-methyl-propan-2-ol | 474 | 4 |
| 167 | 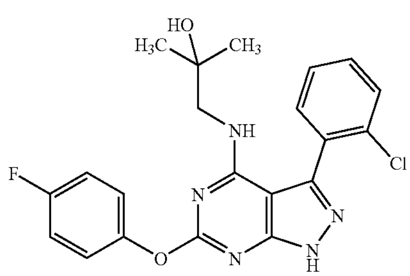 | 1-[3-(2-Chloro-phenyl)-6-(4-fluoro-phenoxy)-1H-pyrazolo[3,4-d]pyrimidin-4-ylamino]-2-methyl-propan-2-ol | 429 | 1 |

TABLE 1-continued

| # | Structure | Name (Autonom™) | MP °C. or M + H | Example |
|---|---|---|---|---|
| 168 | 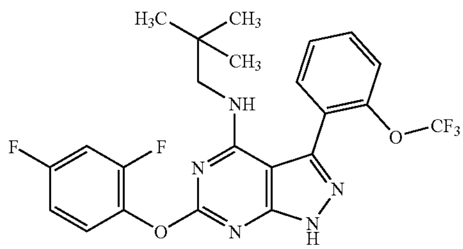 | 1-[6-(2,4-Difluoro-phenoxy)-3-(2-trifluoromethoxy-phenyl)-1H-pyrazolo[3,4-d]pyrimidin-4-ylamino]-2-methyl-propan-2-ol | 496 | 4 |
| 169 | 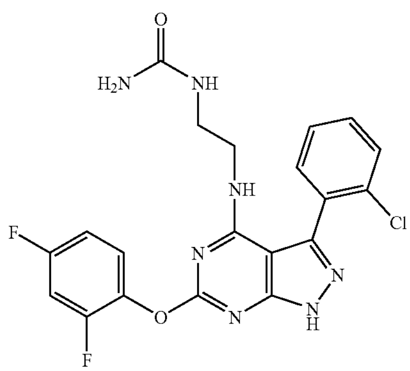 | {2-[3-(2-Chloro-phenyl)-6-(2,4-difluoro-phenoxy)-1H-pyrazolo[3,4-d]pyrimidin-4-ylamino]-ethyl}-urea | 461 | 1 |
| 170 | 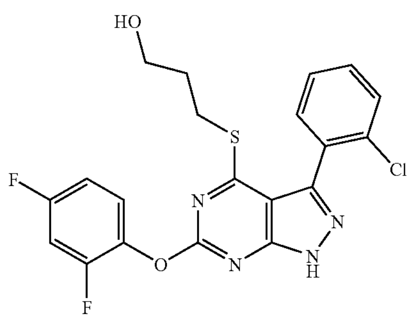 | 3-[3-(2-Chloro-phenyl)-6-(2,4-difluoro-phenoxy)-1H-pyrazolo[3,4-d]pyrimidin-4-ylsulfanyl]-propan-1-ol | 450 | 5 |
| 171 | 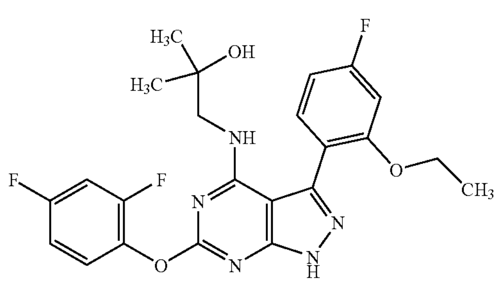 | 1-[6-(2,4-Difluoro-phenoxy)-3-(2-ethoxy-4-fluoro-phenyl)-1H-pyrazolo[3,4-d]pyrimidin-4-ylamino]-2-methyl-propan-2-ol | 474 | 4 |
| 172 | 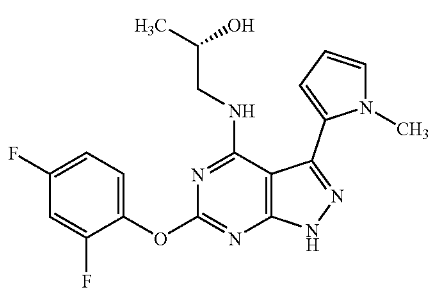 | 1-[6-(2,4-Difluoro-phenoxy)-3-(1-methyl-1H-pyrrol-2-yl)-1H-pyrazolo[3,4-d]pyrimidin-4-ylamino]-propan-2-ol | 401 | 4 |

TABLE 1-continued

| # | Structure | Name (Autonom ™) | MP ° C. or M + H | Example |
|---|---|---|---|---|
| 173 | 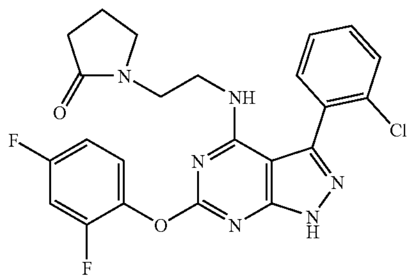 | 1-{2-[3-(2-Chloro-phenyl)-6-(2,4-difluoro-phenoxy)-1H-pyrazolo[3,4-d]pyrimidin-4-ylamino]-ethyl}-pyrrolidin-2-one | 486 | 1 |
| 174 | 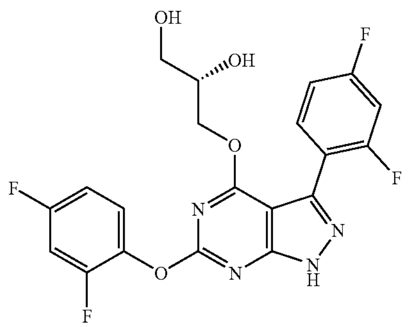 | 3-[6-(2,4-Difluoro-phenoxy)-3-(2,4-difluoro-phenyl)-1H-pyrazolo[3,4-d]pyrimidin-4-yloxy]-propane-1,2-diol | 451 | 4 |
| 175 | 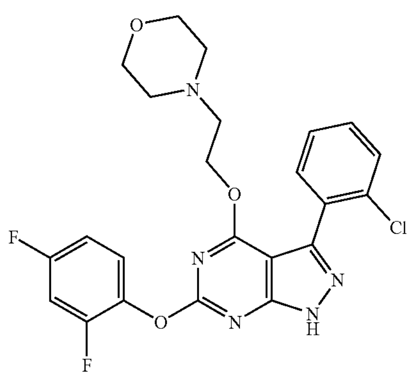 | 3-(2-Chloro-phenyl)-6-(2,4-difluoro-phenoxy)-4-(2-morpholin-4-yl-ethoxy)-1H-pyrazolo[3,4-d]pyrimidine | 489 | 5 |
| 176 | 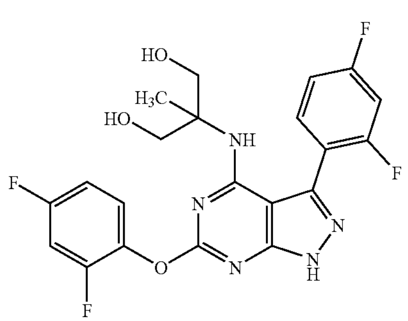 | 2-[6-(2,4-Difluoro-phenoxy)-3-(2,4-difluoro-phenyl)-1H-pyrazolo[3,4-d]pyrimidin-4-ylamino]-2-methyl-propane-1,3-diol | 464 | 5 |

TABLE 1-continued

| # | Structure | Name (Autonom ™) | MP ° C. or M + H | Example |
|---|---|---|---|---|
| 177 | 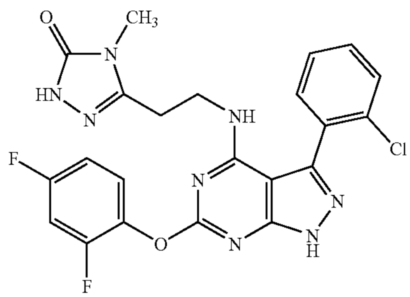 | 5-{2-[3-(2-Chloro-phenyl)-6-(2,4-difluoro-phenoxy)-1H-pyrazolo[3,4-d]pyrimidin-4-ylamino]-ethyl}-4-methyl-2,4-dihydro-[1,2,4]triazol-3-one | 500 | 1 |
| 178 | 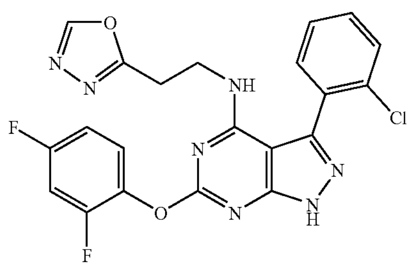 | [3-(2-Chloro-phenyl)-6-(2,4-difluoro-phenoxy)-1H-pyrazolo[3,4-d]pyrimidin-4-yl]-(2-[1,3,4]oxadiazol-2-yl-ethyl)-amine | 471 | 1 |
| 179 | 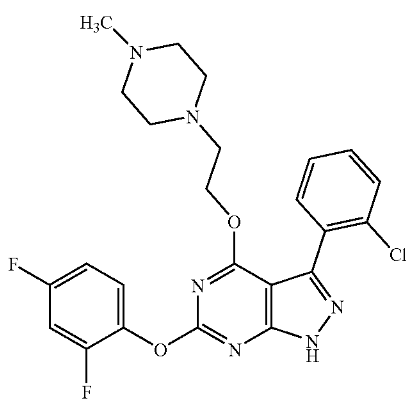 | 3-(2-Chloro-phenyl)-6-(2,4-difluoro-phenoxy)-4-[2-(4-methyl-piperazin-1-yl)-ethoxy]-1H-pyrazolo[3,4-d]pyrimidine | 502 | 5 |
| 180 | 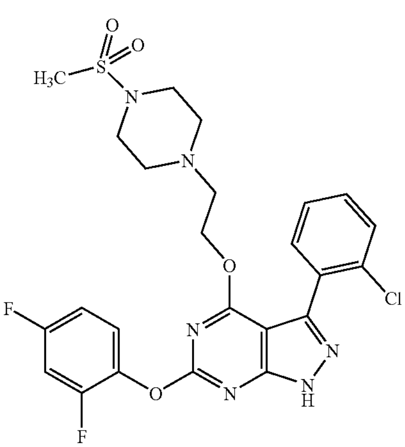 | 3-(2-Chloro-phenyl)-6-(2,4-difluoro-phenoxy)-4-[2-(4-methanesulfonyl-piperazin-1-yl)-ethoxy]-1H-pyrazolo[3,4-d]pyrimidine | 566 | 5 |

TABLE 1-continued

| # | Structure | Name (Autonom ™) | MP ° C. or M + H | Example |
|---|---|---|---|---|
| 181 | 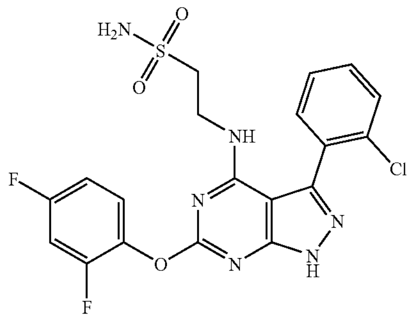 | 2-[3-(2-Chloro-phenyl)-6-(2,4-difluoro-phenoxy)-1H-pyrazolo[3,4-d]pyrimidin-4-ylamino]-ethanesulfonic acid amide | 482 | 1 |
| 182 | 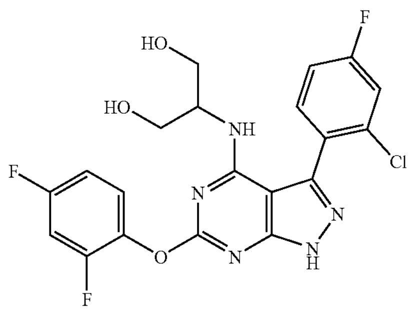 | 2-[3-(2-Chloro-4-fluoro-phenyl)-6-(2,4-difluoro-phenoxy)-1H-pyrazolo[3,4-d]pyrimidin-4-ylamino]-propane-1,3-diol | 467 | 4 |
| 183 | 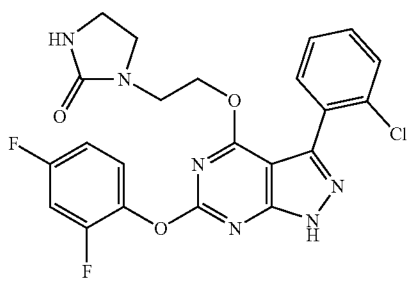 | 1-{2-[3-(2-Chloro-phenyl)-6-(2,4-difluoro-phenoxy)-1H-pyrazolo[3,4-d]pyrimidin-4-yloxy]-ethyl}-imidazolidin-2-one | 488 | 5 |
| 184 | 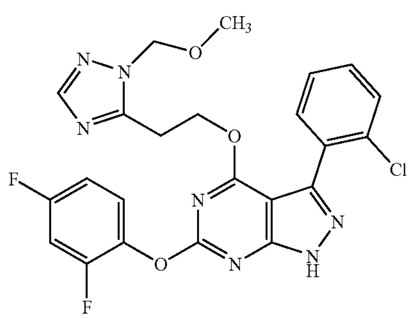 | [3-(2-Chloro-phenyl)-6-(2,4-difluoro-phenoxy)-1H-pyrazolo[3,4-d]pyrimidin-4-yl]-[2-(2-methoxymethyl-2H-[1,2,4]triazol-3-yl)-ethyl]-amine | 514 | 1 |
| 185 | 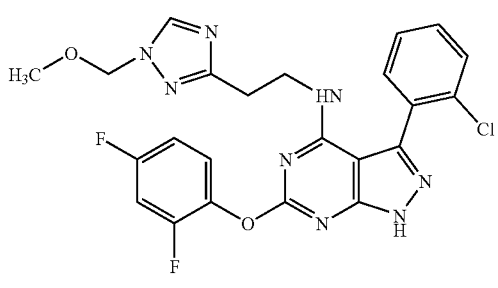 | [3-(2-Chloro-phenyl)-6-(2,4-difluoro-phenoxy)-1H-pyrazolo[3,4-d]pyrimidin-4-yl]-[2-(1-methoxymethyl-1H-[1,2,4]triazol-3-yl)-ethyl]-amine | 514 | 1 |

TABLE 1-continued

| # | Structure | Name (Autonom ™) | MP ° C. or M + H | Example |
|---|---|---|---|---|
| 186 | 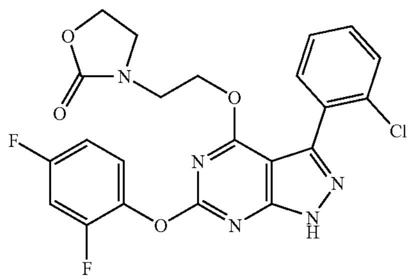 | 3-{2-[3-(2-Chloro-phenyl)-6-(2,4-difluoro-phenoxy)-1H-pyrazolo[3,4-d]pyrimidin-4-ylamino]-ethyl}-oxazolidin-2-one | 488 | 1 |
| 187 | 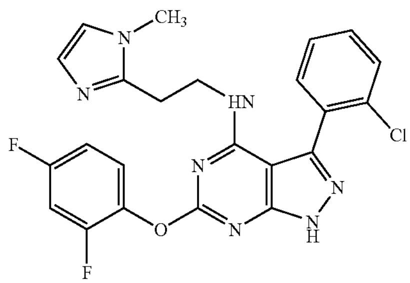 | [3-(2-Chloro-phenyl)-6-(2,4-difluoro-phenoxy)-1H-pyrazolo[3,4-d]pyrimidin-4-yl]-[2-(1-methyl-1H-imidazol-2-yl)-ethyl]-amine | 483 | 1 |
| 188 | 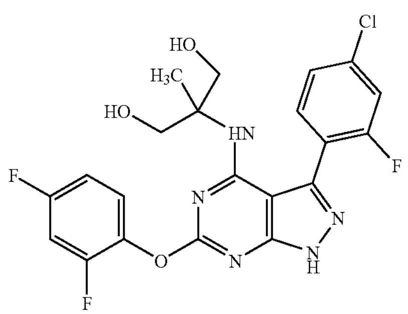 | 2-[3-(4-Chloro-2-fluoro-phenyl)-6-(2,4-difluoro-phenoxy)-1H-pyrazolo[3,4-d]pyrimidin-4-ylamino]-2-methyl-propane-1,3-diol | 481 | 4 |
| 189 | 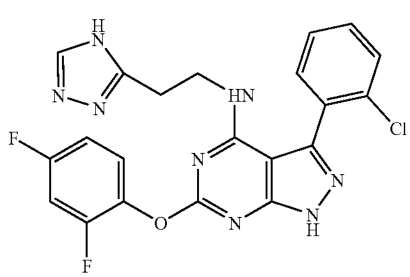 | [3-(2-Chloro-phenyl)-6-(2,4-difluoro-phenoxy)-1H-pyrazolo[3,4-d]pyrimidin-4-yl]-[2-(4H-[1,2,4]triazol-3-yl)-ethyl]-amine | 470 | 1 |
| 190 | 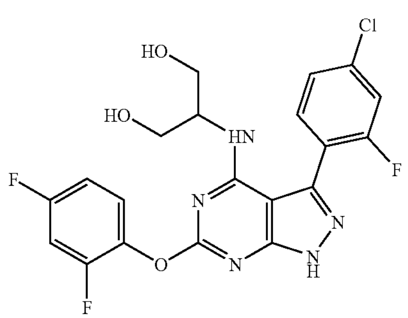 | 2-[3-(4-Chloro-2-fluoro-phenyl)-6-(2,4-difluoro-phenoxy)-1H-pyrazolo[3,4-d]pyrimidin-4-ylamino]-propane-1,3-diol | 467 | 4 |

TABLE 1-continued

| # | Structure | Name (Autonom ™) | MP ° C. or M + H | Example |
|---|---|---|---|---|
| 191 | 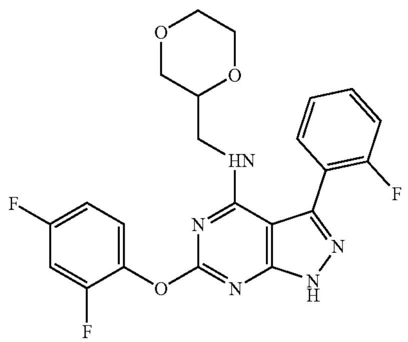 | [3-(2-Chloro-phenyl)-6-(2,4-difluoro-phenoxy)-1H-pyrazolo[3,4-d]pyrimidin-4-yl]-[1,4]dioxan-2-ylmethyl-amine | 475 | 1 |
| 192 | 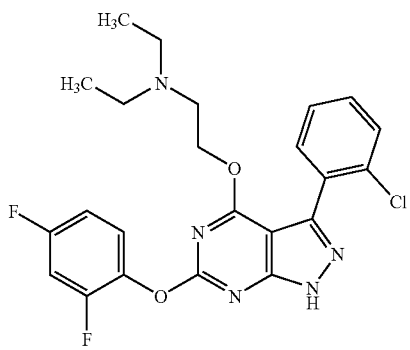 | {2-[3-(2-Chloro-phenyl)-6-(2,4-difluoro-phenoxy)-1H-pyrazolo[3,4-d]pyrimidin-4-yloxy]-ethyl}-diethyl-amine | 475 | 5 |
| 193 | 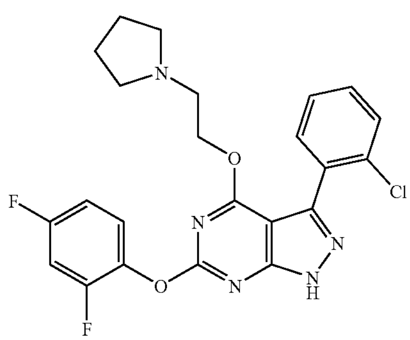 | 3-(2-Chloro-phenyl)-6-(2,4-difluoro-phenoxy)-4-(2-pyrrolidin-1-yl-ethoxy)-1H-pyrazolo[3,4-d]pyrimidine | 473 | 1 |
| 194 | 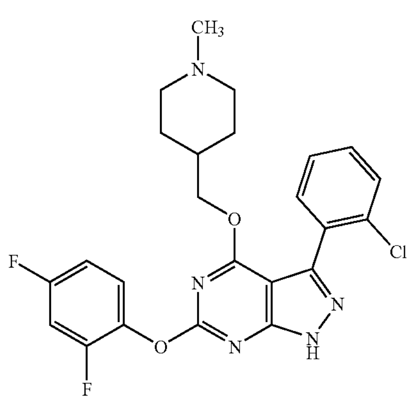 | 3-(2-Chloro-phenyl)-6-(2,4-difluoro-phenoxy)-4-(1-methyl-piperidin-4-ylmethoxy)-1H-pyrazolo[3,4-d]pyrimidine | 487 | 5 |

TABLE 1-continued

| # | Structure | Name (Autonom ™) | MP ° C. or M + H | Example |
|---|---|---|---|---|
| 195 | 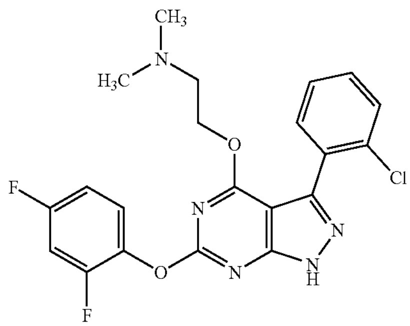 | {2-[3-(2-Chloro-phenyl)-6-(2,4-difluoro-phenoxy)-1H-pyrazolo[3,4-d]pyrimidin-4-yloxy]-ethyl}-dimethyl-amine | 447 | 5 |
| 196 | 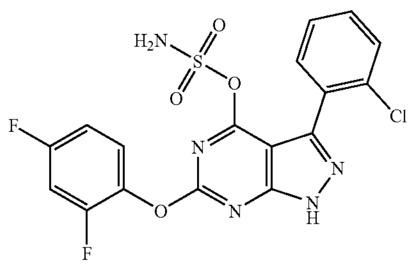 | [3-(2-Chloro-phenyl)-6-(2,4-difluoro-phenoxy)-1H-pyrazolo[3,4-d]pyrimidin-4-yl]-methanesulfonamide | 453 | 6 |
| 197 | 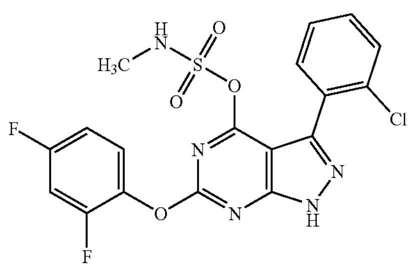 | C-[3-(2-Chloro-phenyl)-6-(2,4-difluoro-phenoxy)-1H-pyrazolo[3,4-d]pyrimidin-4-yl]-N-methyl-methanesulfonamide | 467 | 6 |
| 198 | 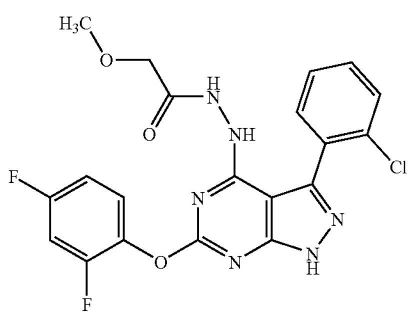 | Methoxy-acetic acid N'-[3-(2-chloro-phenyl)-6-(2,4-difluoro-phenoxy)-1H-pyrazolo[3,4-d]pyrimidin-4-yl]-hydrazide | 462 | 1 |
| 199 | 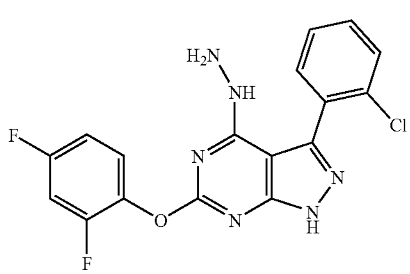 | [3-(2-Chloro-phenyl)-6-(2,4-difluoro-phenoxy)-1H-pyrazolo[3,4-d]pyrimidin-4-yl]-hydrazine | 390 | 1 |

TABLE 1-continued

| # | Structure | Name (Autonom ™) | MP ° C. or M + H | Example |
|---|---|---|---|---|
| 200 | 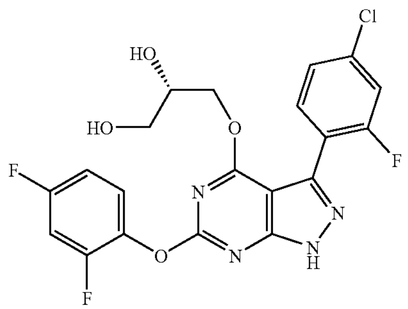 | 3-[3-(4-Chloro-2-fluoro-phenyl)-6-(2,4-difluoro-phenoxy)-1H-pyrazolo[3,4-d]pyrimidin-4-yloxy]-propane-1,2-diol | 468 | 4 |
| 201 | 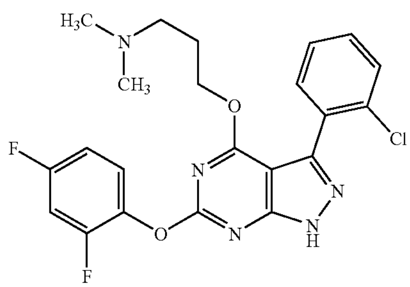 | {3-[3-(2-Chloro-phenyl)-6-(2,4-difluoro-phenoxy)-1H-pyrazolo[3,4-d]pyrimidin-4-yloxy]-propyl}-dimethyl-amine | 461 | 5 |
| 202 | 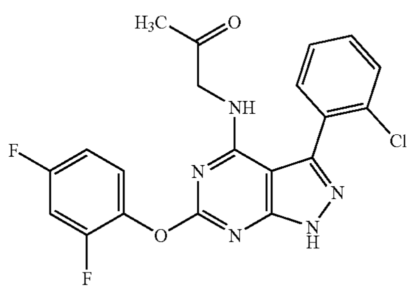 | 1-[3-(2-Chloro-phenyl)-6-(2,4-difluoro-phenoxy)-1H-pyrazolo[3,4-d]pyrimidin-4-ylamino]-propan-2-one | 431 | 1 |
| 203 | 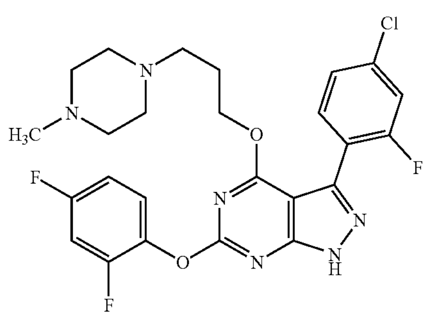 | 3-(2-Chloro-phenyl)-6-(2,4-difluoro-phenoxy)-4-[3-(4-methyl-piperazin-1-yl)-propoxy]-1H-pyrazolo[3,4-d]pyrimidine | 516 | 5 |
| 204 | 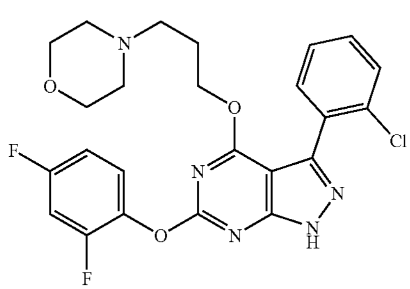 | 3-(2-Chloro-phenyl)-6-(2,4-difluoro-phenoxy)-4-(3-morpholin-4-yl-propoxy)-1H-pyrazolo[3,4-d]pyrimidine | 503 | 5 |

TABLE 1-continued

| # | Structure | Name (Autonom ™) | MP ° C. or M + H | Example |
|---|---|---|---|---|
| 205 | 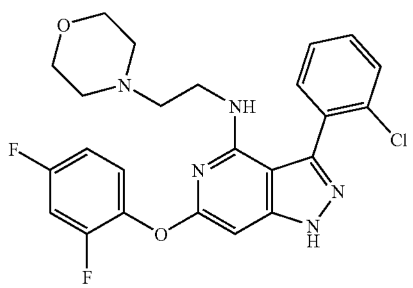 | [3-(2-Chloro-phenyl)-6-(2,4-difluoro-phenoxy)-1H-pyrazolo[4,3-c]pyridin-4-yl]-(2-morpholin-4-yl-ethyl)-amine | 487 | 9 |
| 206 | 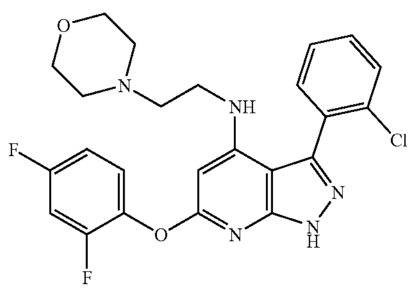 | [3-(2-Chloro-phenyl)-6-(2,4-difluoro-phenoxy)-1H-pyrazolo[3,4-b]pyridin-4-yl]-(2-morpholin-4-yl-ethyl)-amine | 487 | 10 |
| 207 | 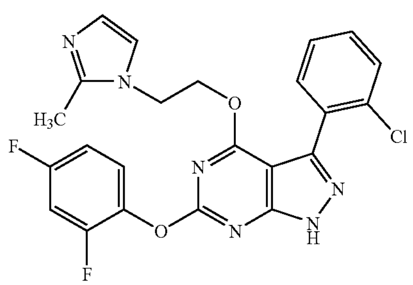 | 3-(2-Chloro-phenyl)-6-(2,4-difluoro-phenoxy)-4-[2-(2-methyl-imidazol-1-yl)-ethoxy]-1H-pyrazolo[3,4-d]pyrimidine | 484 | 5 |
| 208 | 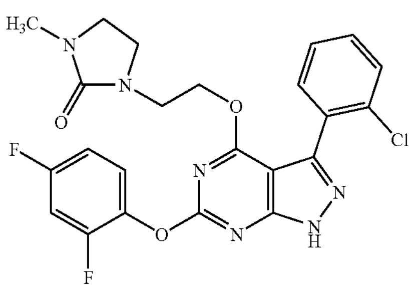 | 1-{2-[3-(2-Chloro-phenyl)-6-(2,4-difluoro-phenoxy)-1H-pyrazolo[3,4-d]pyrimidin-4-ylamino]-ethyl}-3-methyl-imidazolidin-2-one | 501 | 1 |
| 209 | 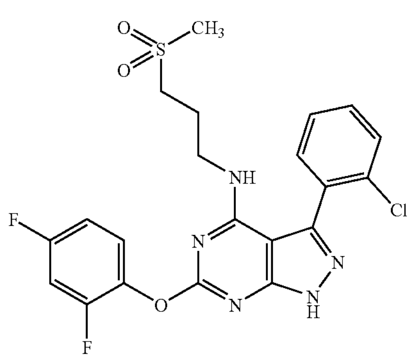 | [3-(2-Chloro-phenyl)-6-(2,4-difluoro-phenoxy)-1H-pyrazolo[3,4-d]pyrimidin-4-yl]-(3-methanesulfonyl-propyl)-amine | 495 | 1 |

TABLE 1-continued

| # | Structure | Name (Autonom ™) | MP ° C. or M + H | Example |
|---|---|---|---|---|
| 210 | 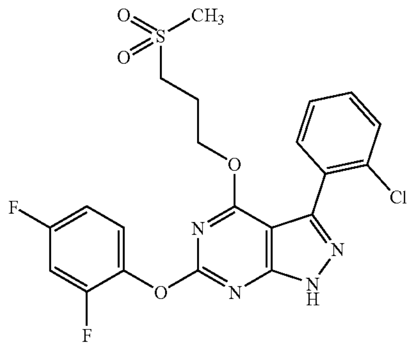 | 3-(2-Chloro-phenyl)-6-(2,4-difluoro-phenoxy)-4-(3-methanesulfonyl-propoxy)-1H-pyrazolo[3,4-d]pyrimidine | 496 | 5 |
| 211 | 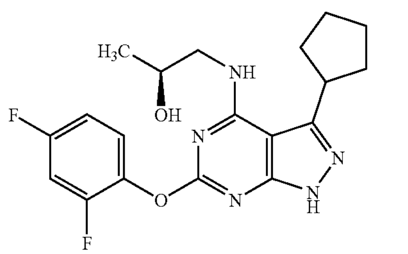 | 1-[3-Cyclopentyl-6-(2,4-difluoro-phenoxy)-1H-pyrazolo[3,4-d]pyrimidin-4-ylamino]-propan-2-ol | 390 | 7 |
| 212 | 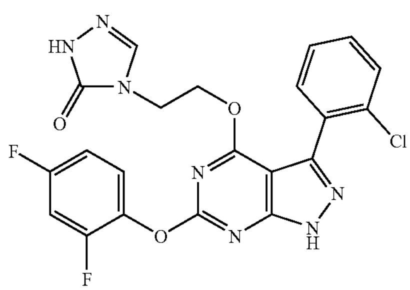 | 4-{2-[3-(2-Chloro-phenyl)-6-(2,4-difluoro-phenoxy)-1H-pyrazolo[3,4-d]pyrimidin-4-ylamino]-ethyl}-2,4-dihydro-[1,2,4]triazol-3-one | 486 | 1 |
| 213 | 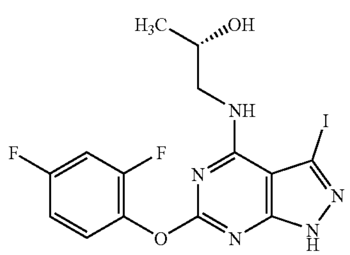 | 1-[6-(2,4-Difluoro-phenoxy)-3-iodo-1H-pyrazolo[3,4-d]pyrimidin-4-ylamino]-propan-2-ol | 448 | 4 |

TABLE 1-continued

| # | Structure | Name (Autonom ™) | MP ° C. or M + H | Example |
|---|---|---|---|---|
| 214 | 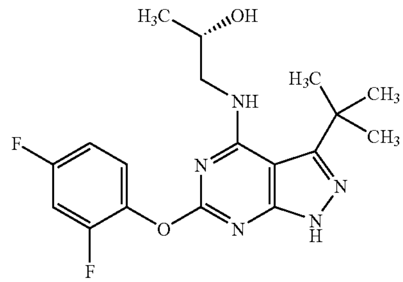 | 1-[3-tert-Butyl-6-(2,4-difluoro-phenoxy)-1H-pyrazolo[3,4-d]pyrimidin-4-ylamino]-propan-2-ol | 378 | 7 |
| 215 | 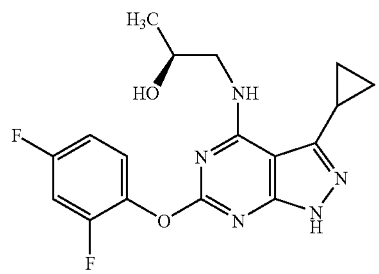 | 1-[3-Cyclopropyl-6-(2,4-difluoro-phenoxy)-1H-pyrazolo[3,4-d]pyrimidin-4-ylamino]-propan-2-ol | 362 | 7 |
| 216 | 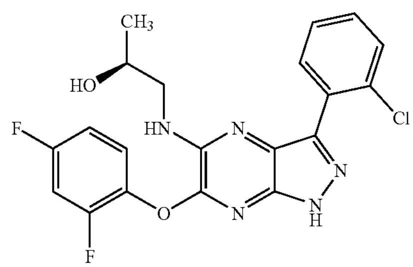 | 1-[3-(2-Chloro-phenyl)-6-(2,4-difluoro-phenoxy)-1H-pyrazolo[3,4-b]pyrazin-5-ylamino]-propan-2-ol | 433 | 8 |
| 217 | 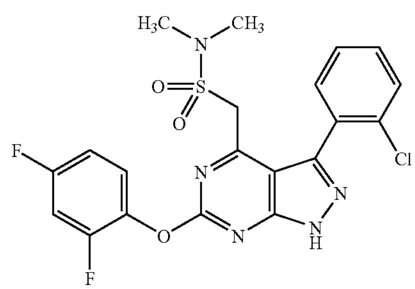 | C-[3-(2-Chloro-phenyl)-6-(2,4-difluoro-phenoxy)-1H-pyrazolo[3,4-d]pyrimidin-4-yl]-N,N-dimethyl-methanesulfonamide | 481 | 6 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1-15; *Rodd's Chemistry of Carbon Compounds,* Elsevier Science Publishers, 1989, Volumes 1-5 and Supplementals; and *Organic Reactions,* Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

One of the specific methods for preparing pyrazolopyrimidine compounds of the invention is shown in Scheme I below.

Scheme I

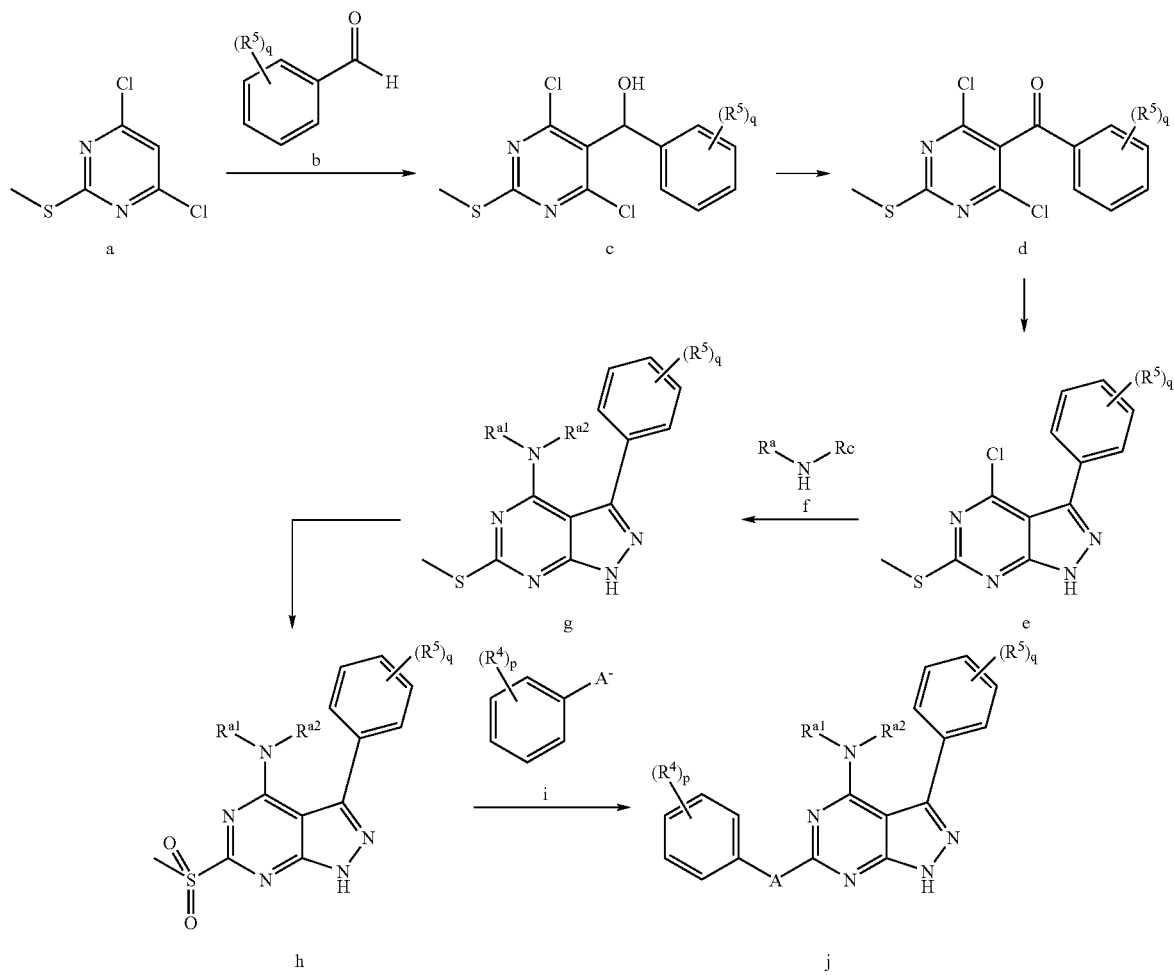

In Scheme I, a dichlorothiopyrimidine a is deprotonated using a base, such as lithium diisopropylamide (LDA) or other suitable bases that are well known to one skilled in the art. The deprotonated pyrimidine a is reacted with a benzaldehyde b or its derivative to produce an alcohol c. This alcohol c is oxidized, e.g., by manganese oxide, to produce a pyrimidine phenyl ketone d. Reacting the ketone d with hydrazine affords a ring closure product in the form of a pyrazolopyrimidine e. Reaction of pyrazolopyrimidine e with a nucleophile such as amine f displaces the chloro group on pyrazolopyrimidine e to afford an amino pyrazolopyrimidine f. Alternatively, an alkoxide $R^aO^-$ or thioalkoxide $R^aS^-$ may be used in place of amine f. The thio group on amino pyrazolopyrimidine f may then be oxidized, e.g., with Oxone, meta-chloroperbenzoic acid, or other oxidizing agents known to one skilled in the art, to produce a sulfonyl pyrazolopyrimidine derivative g. The sulfonyl group on pyrazolopyrimidine derivative g is then displaced with a nucleophilic aryl group h, such as an optionally substituted phenoxide, optionally substituted aniline, or an optionally substituted thiophenoxide, to produce a pyrazolopyrimidine i in accordance with the invention.

Pyrazolopyridinone compounds of the invention may be prepared from a pyrazole compound as shown in Scheme II below, wherein PG is a protecting group and may be the same or different in each occurrence.

Scheme II

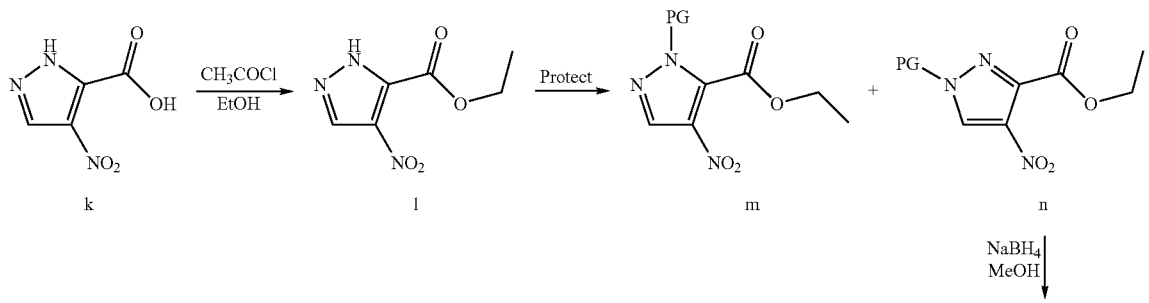

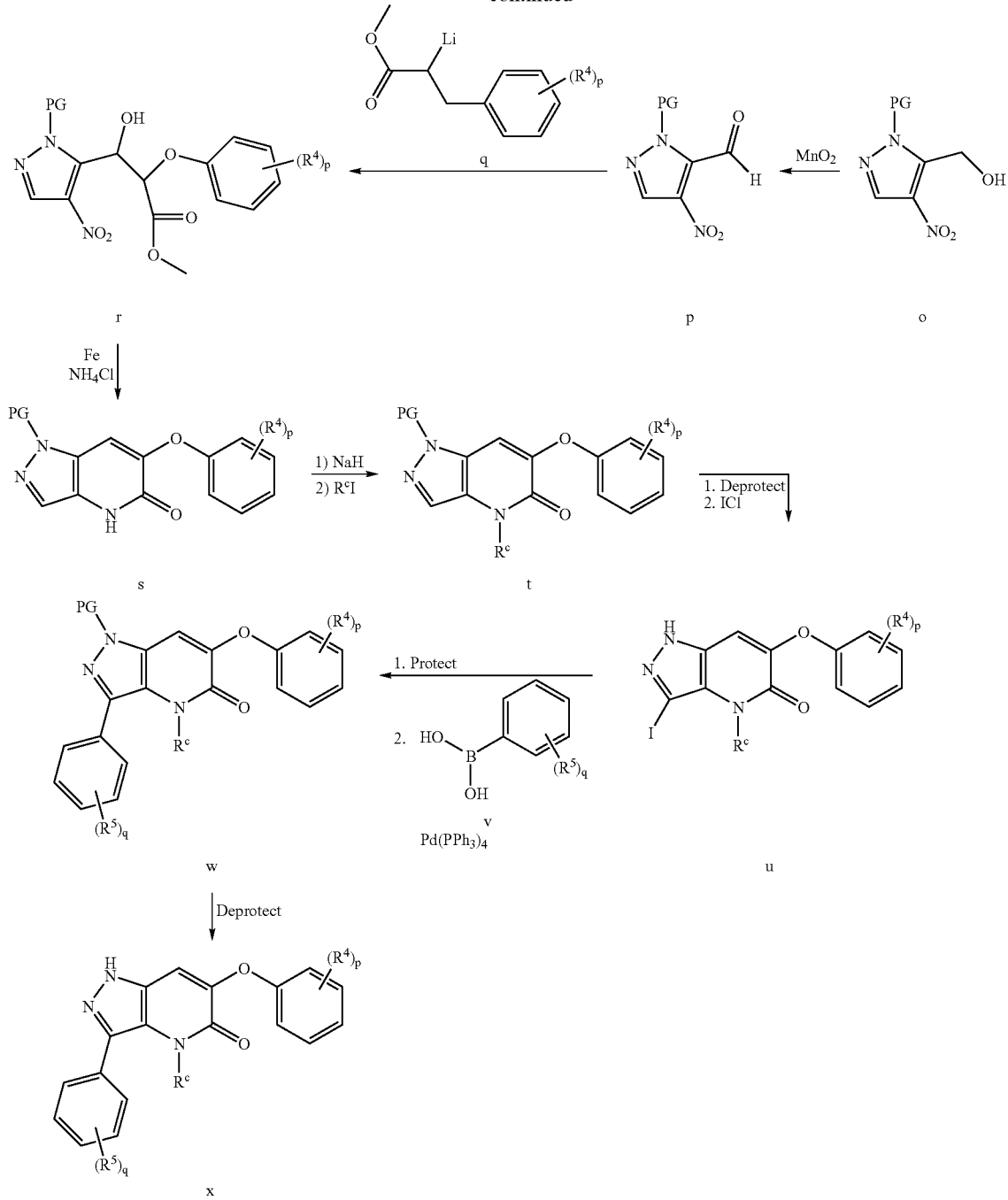

In Scheme II, esterification of a nitropyrazole carboxylic acid compound k yields a nitro pyrazol ester, which is followed by protection of one of the ring nitrogen atom to affords a mixture of protected regioisomers m, n, which are separated. The protectiong group may comprise, for example, a 2-(trimethylsilyl)ethoxy-methyl group. The 2-protected pyrazole compound m is then treated with a reducing agent, such as sodium borohydride or other suitable reducing agents known to one skilled in the art, to provide an alcohol o. The alcohol o is oxidized with manganese (IV) oxide or other suitable oxidizing agents, which are discussed above, to provide a pyrazole carbaldehyde compound p. Condensation reaction of the aldehyde p with an anion of α-aryloxy ester q provides an α-aryloxy-β-hydroxyester r. Reduction of the nitro group of α-aryloxy-β-hydroxyester r with a reducing agent, such as iron in the presence of ammonium chloride or other suitable reducing conditions known to one skilled in the art, results in concomitant ring formation and elimination of the β-hydroxy group to afford a pyrazolopyridinone derivative s. The amide nitrogen is then alkylated under conventional conditions with alkylating agent such as an alkyl or heteroalkyl iodide R$^c$I to afford an N-alkyl pyrazolopyridinone t. Functionalities present on $R^cI$, such as hydroxy groups, may be protected and subsequently deprotected at the end of Scheme II.

Deprotection of the pyrazoline ring portion of the N-alkylated pyrazolopyridinone t, followed by treatment with by iodine monochloride in the presence of potassium carbonate, or other suitable iodination conditions known to one skilled in the art, provides an iodopyrazolopyridinone u. The pyrazole 1-position of iodopyrazolopyridinone u is then protected with Boc or like protecting group, and a cross-coupling reaction with an appropriate aryl or heteroaryl compound v (e.g., a Suzuki coupling with an aryl boronic acid in the presence of a palladium catalyst), provides a protected aryloxy iodopyrazolopyridinone w. Removal of the protecting group on the pyrazoline ring nitrogen atom then affords a pyrazolopyridinone compound x in accordance with the invention.

One of skill in the art will understand that certain modifications to the above schemes are contemplated and within the scope of the present invention. For example, certain steps will involve the use of protecting groups for functional groups that are not compatible with particular reaction conditions.

More specific details for producing compounds of formula (I) are described in the Examples section below.

Pharmaceutical Compositions And Administration

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

Utility

Compounds of the invention are useful for, but not limited to, the treatment of any disorder or disease state in a human, or other mammal, which is exacerbated or caused by excessive or unregulated TNF or p38 kinase production by such mammal. Accordingly, the present invention provides a method of treating a p38-mediated disease which comprises administering an effective amount of a compound of the invention, or a pharmaceutically acceptable salt, solvate or prodrug thereof, to a subject or patient in need thereof.

Compounds of the invention are useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatorydisease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of Alzheimer's disease, influenza, multiple sclerosis, cancer, diabetes, systemic lupus erthrematosis (SLE), skin-related conditions such as psoriasis, eczema, burns, dermatitis, keloid formation, and scar tissue formation. In addition, compounds of the invention are useful in treating gastrointestinal conditions such as inflammatory bowel disease, Crohn's disease, gastritis, irritable bowel syndrome and ulcerative colitis. The compounds are also useful in the treatment of ophthalmic diseases, such as retinitis, retinopathies, uveitis, ocular photophobia, and of acute injury to the eye tissue. The compounds can also be used in treating angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds can further be used for preventing the production of cyclooxygenase-2 and have analgesic properties. Therefore, Compounds of Formula I are useful for treatment of pain.

Other uses for Compounds of Formula I include treatment of HCV, severe asthma, psoriasis, chronic obstructive pulmonary disease (COPD), and other diseases that can be treated with an anti-TNF compound.

Besides being useful for human treatment, these compounds are also useful for veterinary treatment of companion animals, exotic animals and farm animals, including mammals, rodents, and the like. More preferred animals include horses, dogs, and cats.

The present compounds can also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, LTB$_4$ antagonists and LTA$_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Examples.

Abbreviations

DCM dichloromethane
DMF N,N-dimethylformamide
DMAP 4-dimethylaminopyridine
gc gas chromatography
HMPA hexamethylphosphoramide
hplc high performance liquid chromatography
mCPBA m-chloroperbenzoic acid
MeCN acetonitrile
TEA triethylamine
THF tetrahydrofuran
LDA lithium diisopropylamine
TLC thin layer chromatography Example 1

This example illustrates a synthesis of (S)-1-[3-(2-chlorophenyl)-6-2,4-difluorophenoxy)-1H-pyrazolo[3,4-d]pyrimidin-4-ylamino]propan-2-ol following the procedure of Scheme I above.

Step 1. Preparation of (2-chlorophenyl)-(4,6-dichloro-2-methylsulfanylpyrimidin-5-yl)-methanol

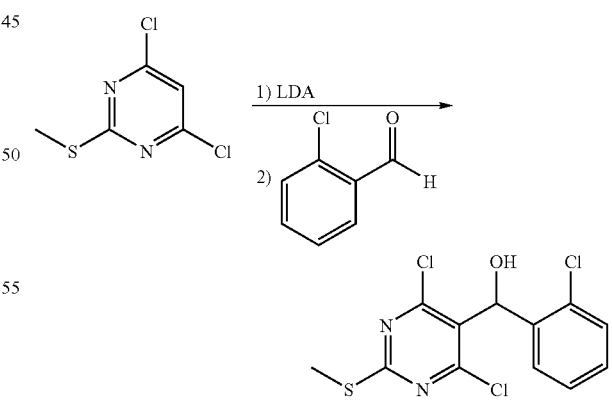

To a solution of 4,6-dichloro-2-(methylthio)pyrimidine (Aldrich) (5.0 g, 25.64 mmol) in dry THF (130 mL) at −78° C. under nitrogen was slowly added a solution of 2.0 M LDA (23.0 mL, 1.8 eq) in THF via a syringe. The resulting mixture was stirred at −78° C. for an additional 20 minutes, after which 2-chlorobenzaldehyde (Aldrich) (7.2 mL, 2 eq) was added dropwise via a syringe. The reaction mixture was stirred for an additional 30 minutes at −78° C. and then quenched with saturated ammonium chloride solution. Ethyl acetate was added, and the mixture was allowed to warm to room temperature. The aqueous layer was separated and extracted with ethyl acetate. The combined organic layers were washed with brine, dried over magnesium sulfate, filtered and concentrated to give the crude product (14.2 g) as an oil. Purification using Flash Column Chromatography on Silica Gel, eluting with 5% ethyl acetate in hexanes gave the title compound (8.60 g, (M+H)⁺=336, M.P.=109.5-112.5° C.) which crystallized upon standing to give a white solid.

Step 2. Preparation of (2-chlorophenyl)-(4,6-dichloro-2-methylsulfanylpyrimidin-5-yl)-methanone

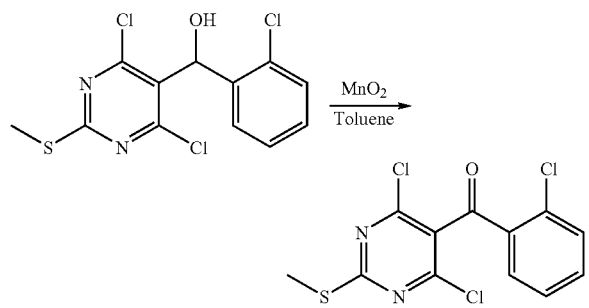

To a solution of (2-chlorophenyl)-(4,6-dichloro-2-methylsulfanylpyrimidin-5-yl)-methanol (8.6 g, 25.6 mmol) in toluene (300 mL) was added manganese (IV) oxide (Aldrich) (22.3 g, 10 eq), and the resulting mixture was heated to reflux with stirring for a total of 5 hours. The reaction was cooled to room temperature and then filtered through a 3.5 cm pad of Celite and the filtrate was concentrated to give 8.84 g of a crude product. Purification by Flash Column Chromatography on Silica Gel eluting with a gradient starting with pure hexanes and progressing to 2% ethyl acetate in hexanes and finally 5% ethyl acetate in hexanes gave the title compound as an off-white powder (1.388 g, (M+H)⁺=333).

Step 3. Preparation of 4-chloro-3-(2-chlorophenyl)-6-methylsulfanyl-1H-pyrazolo[3,4-d]pyrimidine

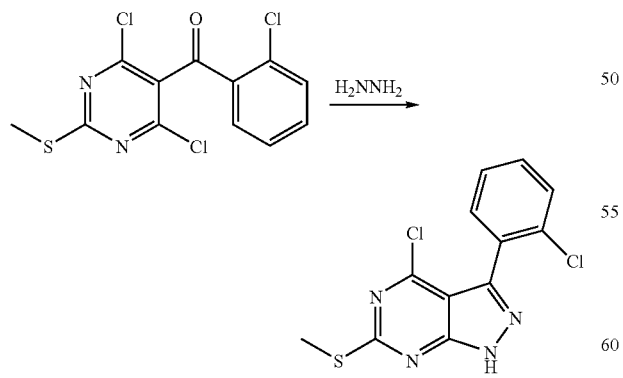

To a mixture of (2-chlorophenyl)-(4,6-dichloro-2-methylsulfanylpyrimidin-5-yl)-methanone (875 mg, 2.62 mmol) and N,N-diisopropyl ethyl amine (0.69 mL, 1.5 eq) in THF (20 mL) at 0° C. was added a solution of hydrazine (83 μL, 1 eq) in THF (20 mL) dropwise with stirring. After addition was complete, the reaction was gradually warmed to room temperature over 2 hours. Analysis by TLC indicated that there was still starting material remaining. Additional 3 mL of a solution of hydrazine (17 μL) in THF (10 mL) was added dropwise to the reaction mixture, and the reaction mixture was stirred at room temperature overnight. The reaction mixture was diluted with ethyl acetate (150 mL) and water (50 mL). The organic layer was separated, washed with water (4×50 mL) and brine (1×50 mL), dried over magnesium sulfate, filtered and concentrated to give the title compound as a yellowish powder (867 mg, (M+H)⁺=311).

Step 4. Preparation of (S)-1-[3-(2-chlorophenyl)-6-methylsulfanyl-1H-pyrazolo[3,4-d]pyrimidin-4-ylamino]-propan-2-ol

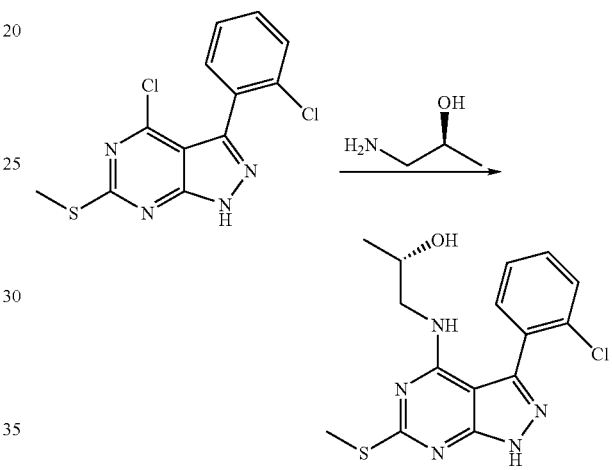

To a mixture of 4-chloro-3-(2-chloro-phenyl)-6-methylsulfanyl-1H-pyrazolo[3,4-d]pyrimidine (300 mg, 0.964 mmol) and N,N-diisopropylethyl amine (0.34 mL, 2 eq) in THF (5 mL) was added dropwise a solution of (S)-(+)-1-amino-2-propanaol (Aldrich) (0.217 g, 3 eq) in THF. The resulting mixture was stirred at room temperature overnight. The reaction was monitored by TLC analysis. The reaction mixture was diluted with ethyl acetate (150 mL) and water (70 mL). The organic layer was separated, washed with water (2×70 mL) and brine (1×70 mL), dried over magnesium sulfate, filtered and concentrated to give the title compound as an off-white solid (328 mg, (M+H)⁺=350).

Step 5. Preparation of (S)-1-[3-(2-chlorophenyl)-6-methanesulfonyl-1H-pyrazolo[3,4d]pyrimidin4-ylamino]propan-2-ol

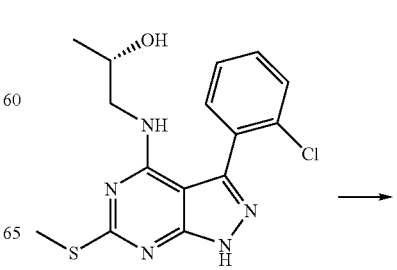

-continued

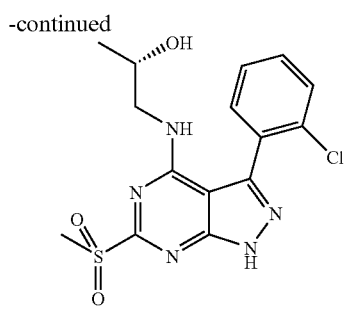

To a solution of (S)-1-[3-(2-chlorophenyl)-6-methylsulfanyl-1H-pyrazolo[3,4-d]pyrimidin-4-ylamino]propan-2-ol (320 mg, 0.915 mmol) in THF (15 mL) and methanol (5 mL) was added m-chloroperoxybenzoic acid (Aldrich) (431 mg, 2.1 eq) and the resulting mixture was stirred for 30 hours at room temperature. The reaction was monitored by TLC analysis. The reaction mixture was diluted with ethyl acetate (170 mL) and saturated sodium bicarbonate (50 mL). The organic layer was separated, washed with saturated sodium bicarbonate (3×50 mL) and brine (1×50 mL), dried over magnesium sulfate, filtered and concentrated to give the title compound as an off-white powder (325 mg, (M+H)$^+$=382).

Step 6. Preparation of (S)-1-[3-(2-chlorophenyl)-6-(2,4-difluorophenoxy)-1H-pyrazolo[3,4-d]pyrimidin-4-ylamino]propan-2-ol

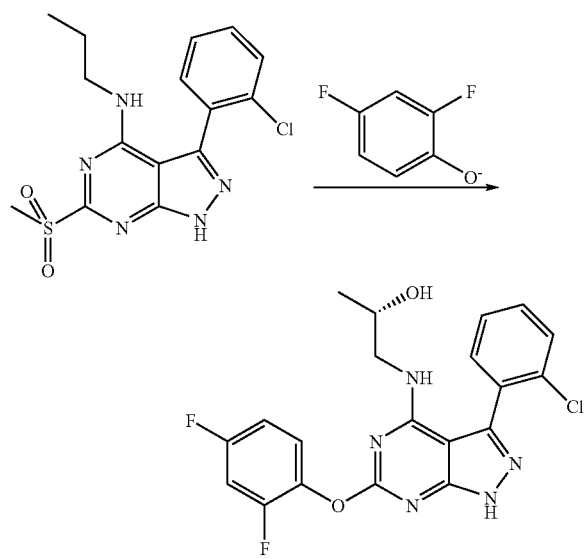

To a 0° C. solution of 2,4-difluorophenol (Aldrich) (0.15 mL, 4 eq) in DMSO (2 mL) in a Microwave Reactor Vessel was added a 1.0 M solution of potassium tert-butoxide in THF (1.61 mL, 4.1 eq). The resulting solution was warmed to room temperature and stirred for 10 minutes and then the reaction mixture was placed in the Microwave Reactor and heated at 150° C. for 1 hour. The reaction mixture was cooled and diluted with ethyl acetate (150 mL) and water (50 mL). The organic layer was separated, washed with water (2×50 mL) and brine (1×50 mL), dried over magnesium sulfate, filtered and concentrated to provide the crude compound (370 mg). Purification by Preparative Thin Layer Chromatography eluting with 5% methanol in dichloromethane gave the title compound as a white powder (109 mg, (M+H)$^+$=432, M.P.=254.6-258.2° C.).

Additional compounds prepared according to the above example are shown in Table 1.

Example 2

This example illustrates the synthesis of 3-(2-chloro-phenyl)-6-(2,4-difluoro-phenoxy)-4-methyl-1,4-dihydro-pyrazolo[4,3-b]pyridin-5-one following the procedure of Scheme II above.

Step 1. Preparation of 4-Nitro-1H-pyrazole-3-carboxylic acid, ethyl ester

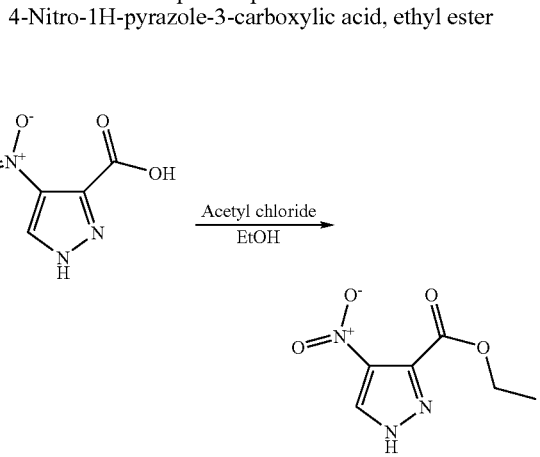

Acetyl chloride (50 mL) was added dropwise to ethanol (450 mL) at 0° C. with stirring. After addition was complete, the ice-bath was removed, and the mixture was stirred at room temperature for 30 minutes. To this mixture was added 4-nitro-1H-pyrazole-3-carboxylic acid (Aldrich) (10 g, 63.65 mmol), and the resulting homogeneous mixture was stirred at room temperature for a total of 48 hours. The reaction was monitored by TLC. The solvent was removed under reduced pressure and then co-evaporated with ethyl acetate four times. The residue was concentrated under high vacuum to give the title compound as a white powder (11.426 g, (M–H)$^+$=184, M.P.=128.0-130.1° C.).

Step 2. Preparation of 4-nitro-1-(2-trimethylsilanyl-ethoxymethyl)-1H-pyrazole-3-carboxylic acid, ethyl ester and 4-nitro-2-(2-trimethylsilanyl-ethoxymethyl)-2H-pyrazole-3-carboxylic acid, ethyl ester

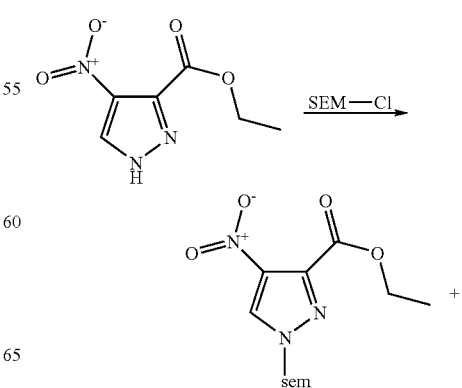

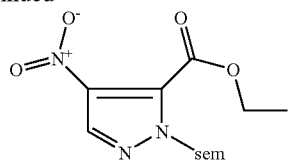

To a 0° C. solution of 4-nitro-1H-pyrazole-3-carboxylic acid ethyl ester (6.4 g, 34.58 mmol) in dimethylformamide (80 mL) was added sodium hydride (2.07 g, 1.5 eq), and the resulting mixture was stirred from 0° C. to room temperature for one hour. To this mixture was added 2-(trimethylsilyl) ethoxy-methyl chloride (Aldrich) (9.17 mL, 1.5 eq), and the resulting mixture was stirred at room temperature for 2 days. The reaction was monitored by TLC. The reaction mixture was diluted with ethyl acetate (300 mL) and water (100 mL). the organic layer was separated, washed with water (6×100 mL) and brine (1×100 mL), dried over magnesium sulfate, filtered and concentrated to give 10 g of the crude product. Purification by column chromatography using 5% ethyl acetate in hexanes afforded 4-nitro-2-(2-trimethylsilanyl-ethoxymethyl)-2H-pyrazole-3-carboxylic acid, ethyl ester (3.82 g) as a colorless oil and 4-nitro-1-(2-trimethylsilanyl-ethoxymethyl)-1H-pyrazole-3-carboxylic acid, ethyl ester (4.055 g) as a light tan oil. (M−H)+=314.

Step 3. Preparation of [4-nitro-2-(2-trimethylsilanyl-ethoxymethyl)-2H-pyrazol-3-yl]-methanol

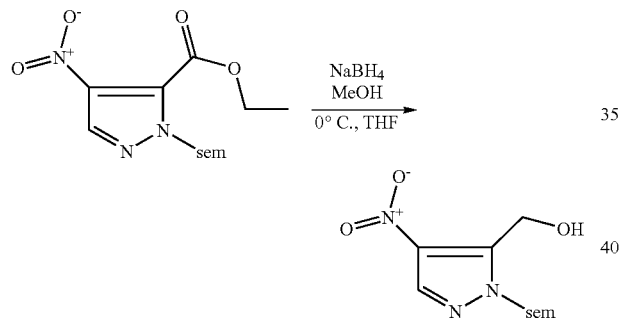

To a 0° C. solution of 4-nitro-2-(2-trimethylsilanyl-ethoxymethyl)-2H-pyrazole-3-carboxylic acid, ethyl ester (10 g, 31.7 mmol) in tetrahydrofuran (200 mL) was added methanol (24 mL) followed by sodium borohydride (9.59 g, 8 eq) in one portion. The resulting mixture was stirred at 0° C. for 20 minutes. The reaction mixture was then added to a mixture of saturated aqueous ammonium chloride solution (600 mL) and ethyl acetate (800 mL) in an ice-bath. A solution of 4 N HCl was added with stirring at 0° C. to adjust the pH of the aqueous layer to about 4. The organic layer was separated and washed with brine (1×500 mL), dried over magnesium sulfate, filtered and concentrated to give the title compound (7.76 g) as a reddish oil. M+=273.

Step 4. Preparation of 4-nitro-2-(2-trimethylsilanyl-ethoxymethyl)-2H-pyrazole-3-carbaldehyde

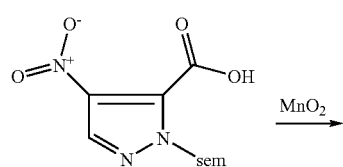

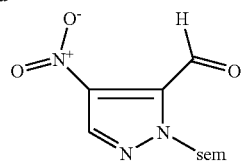

To a solution of [4-nitro-2-(2-trimethylsilanyl-ethoxymethyl)-2H-pyrazol-3-yl]methanol (7.776 g, 28.38 mmol) in chloroform (500 mL) was added manganese dioxide (29.18 g, 9 eq). The resulting mixture was heated at reflux for 4 hours, cooled to room temperature and stirred overnight. The reaction mixture was again heated to reflux for 3 hours, filtered through a 3 cm plug of celite using additional chloroform. The filtrate was concentrated to give 4.55 g of crude material and purified via silica gel chromatography with a 2-4% ethyl acetate in hexanes gradient to give the title compound as a colorless oil (1.55 g). M+=271

Step 5: Preparation of 2-(2,4-difluorophenoxy)-3-hydroxy-3-[4-nitro-2-(2-trimethylsilanyl-ethoxymethyl)-2H-pyrazol-3-yl]propionic acid methyl ester To a −78° C. solution of diisopropylamine (0.3 mL, 2.1 eq) in diethyl ether (3 mL) was added a 2.5 M solution of n-butyllithium in hexanes (Aldrich) (0.84 mL, 2.1 eq). The resulting mixture was stirred for 15 minutes. To this mixture was added a solution of (2,4-difluorophenoxy)acetic acid methyl ester (425 mg, 2.1 eq) in diethyl ether (2 mL) via a syringe, and the resulting mixture was stirred at −78° C. for 30 minutes, after which a solution of 4-nitro-2-(2-trimethylsilanyl-ethoxymethyl)-2H-pyrazole-3-carbaldehyde (271 mg, 1 mmol) in diethyl ether (2 mL) was added. The resulting mixture was stirred for 2 hours. The −78° C. reaction mixture was diluted with a saturated aqueous ammonium chloride solution, then diluted with ethyl acetate (150 mL) and water (25 mL). The organic layer was separated, washed with brine (1×50 mL), dried over magnesium sulfate, filtered and concentrated to give the crude product as an oil (709 mg). Purification of the crude product by Preparative Thin Layer Chromatography eluting with 25% ethyl acetate in hexanes gave the title compound as a diastereomeric mixture (257 mg, thick colorless oil). M+=473.

Step 6: Preparation of 6-(2,4-difluorophenoxy)-1-(2-trimethylsilanyl-ethoxymethyl)-1,4-dihydro-pyrazolo[4,3-b]pyridin-5-one

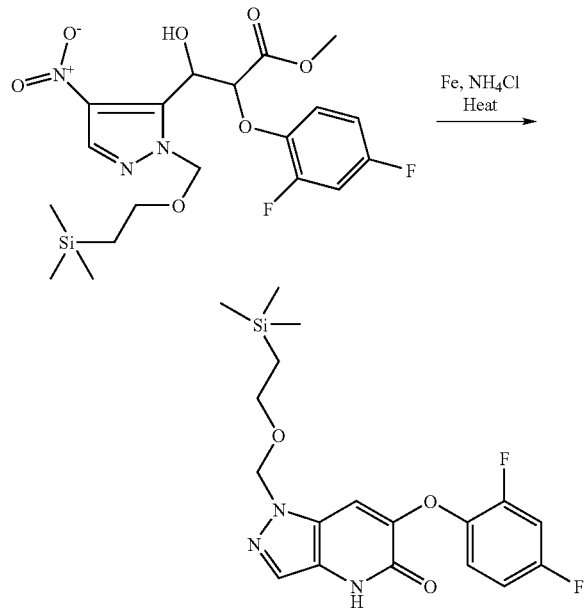

To a solution of 2-(2,4-difluorophenoxy)-3-hydroxy-3-[4-nitro-2-(2-trimethylsilanyl-ethoxymethyl)-2H-pyrazol-3-yl] propionic acid methyl ester (125 mg, 0.264 mmol) in ethanol (2 mL) and water (1 mL) was added ammonium chloride (74 mg, 5.2 eq) followed by iron powder (Fisher Brand, Electrolytic). The resulting mixture was stirred at room temperature for 45 minutes, refluxed overnight, cooled to room temperature, diluted with ethanol, and filtered through a 3 cm bed of celite with additional ethanol. The filtrate was concentrated, and the residue was diluted with ethyl acetate (80 mL) and water (40 mL). The organic layer was separated, washed with water (2×40 mL) and brine (1×40 mL), dried over magnesium sulfate, filtered and concentrated to give the title compound as a thick tan oil (98 mg, (M+H)$^+$=394).

Step 7: Preparation of 6-(2,4-difluorophenoxy)-4-methyl-1-(2-trimethylsilanyl-ethoxymethyl)-1,4-dihydro-pyrazolo[4,3-b]pyridin-5-one

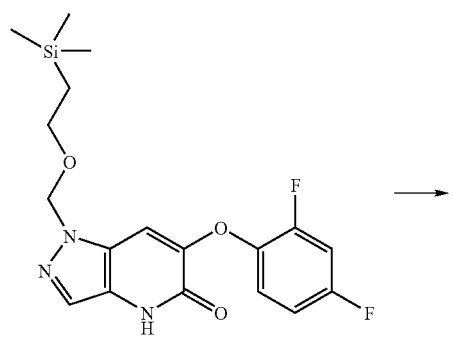

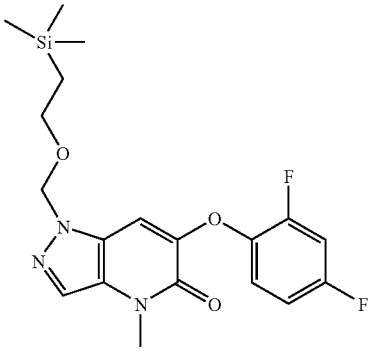

To a 0° C. solution of 6-(2,4-difluorophenoxy)-1-(2-trimethylsilanyl-ethoxymethyl)-1,4-dihydro-pyrazolo[4,3-b]pyridin-5-one (98 mg, 0.249 mmol) in dimethylformamide (1 mL) was added sodium hydride (60% dispersion in oil, Aldrich) (15 mg, 1.5 eq) and the resulting mixture was stirred at for 30 minutes, after which methyl iodide (25 µL, 1.5 eq) was added and the mixture was stirred additional 1 hour with warming from 0° C. to room temperature. The reaction mixture was diluted with ethyl acetate (35 mL) and water (25 mL). The organic layer was separated, washed with water (2×25 mL) and brine (1×25 mL), dried over magnesium sulfate, filtered and concentrated to give the title compound as a tan powder (118 mg, (M+H)$^+$=408).

Step 8: Preparation of 6-(2,4-difluorophenoxy)-3-iodo-4-methyl-1,4-dihydro-pyrazolo[4,3-b]pyridin-5-one

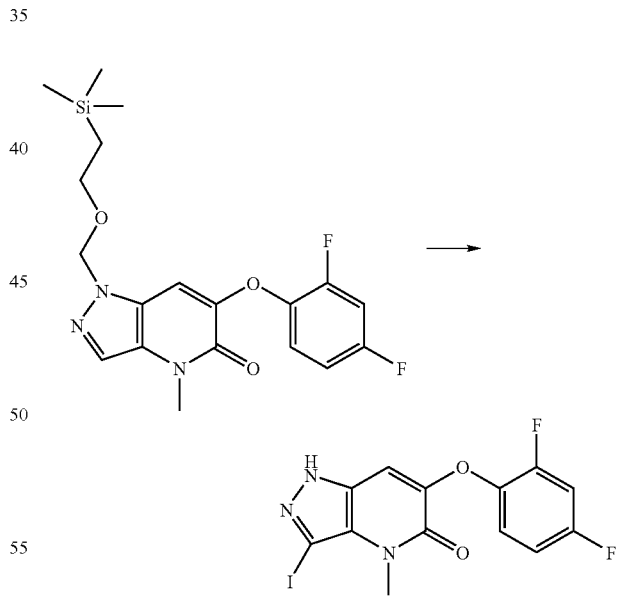

To a solution of 6-(2,4-difluorophenoxy)-4-methyl-1-(2-trimethylsilanyl-ethoxymethyl)-1,4-dihydro-pyrazolo[4,3-b]pyridin-5-one (118 mg, 0.289 mmol) in chloroform (25 mL) was added iodine monochloride (141 mg, 3 eq) followed by potassium carbonate (200 mg, 5 eq) and the resulting mixture was heated under reflux with stirring (in the dark) for 24 hours. Additional iodine monochloride (large excess) was added and the resulting solution was stirred under reflux for another 16 hours. The reaction mixture was cooled to room temperature and diluted with dichloromethane, and washed 2× with an aqueous solution of $Na_2S_2O_{3(aq)}$ followed by brine. The organic layer was dried over magnesium sulfate, filtered and concentrated to give the crude product as an oil (97 mg). Purification by Preparative Thin Layer Chromatography eluting with 60% ethyl acetate in hexanes gave the title compound as an off-white powder (12 mg, $(M+H)^+=462$).

Step 9: Preparation of 6-(2,4-difluorophenoxy)-3-iodo-4-methyl-5-oxo-4,5-dihydro-pyrazolo[4,3-b]pyridine-1-carboxylic acid tert-butyl ester

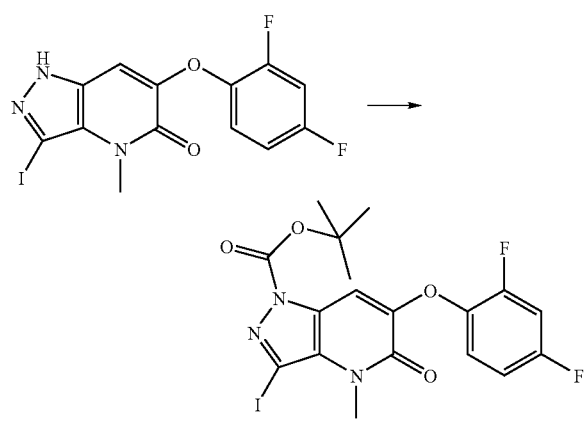

To a solution of 6-(2,4-difluorophenoxy)-3-iodo-4-methyl-1,4-dihydro-pyrazolo[4,3-b]pyridin-5-one (12 mg, 0.0298 mmol) in tetrahydrofuran (5 mL) was added $BOC_2O$ (16 mg, 2.5 eq) and DMAP (catalytic). The resulting mixture was heated under reflux for 30 minutes, cooled to room temperature, and diluted with ethyl acetate (35 mL) and water (25 mL). The organic layer was separated, washed successively with water (2×25 mL), 0.5 N HCl (2×20 mL) and brine (1×25 mL), dried over magnesium sulfate, filtered and concentrated to give the title compound as a white powder (18 mg, $(M+H)^+=504$).

Step 10: Preparation of 3-(2-chlorophenyl)-6-(2,4-difluorophenoxy)-4-methyl-5-oxo-4,5-dihydro-pyrazolo[4,3-b]pyridine-1-carboxylic acid tert-butyl ester

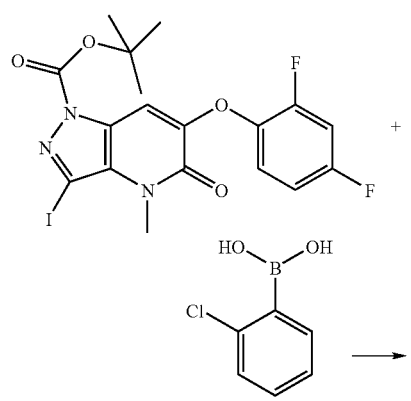

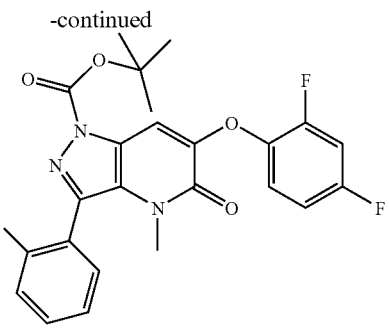

To a solution of 6-(2,4-difluorophenoxy)-3-iodo-4-methyl-5-oxo-4,5-dihydro-pyrazolo[4,3-b]pyridine-1-carboxylic acid tert-butyl ester (18 mg) in benzene (1.3 mL) and methanol (0.26 mL) was added 1 M aqueous solution of sodium carbonate (76 μL, 2 eq), 2-chlorophenylboronic acid (12 mg, 2 eq), and $Pd(PPh_3)_4$ (13 mg, 0.3 eq). The mixture was purged with argon, heated at reflux for 2 hours, cooled to room temperature, and diluted with ethyl acetate (35 mL) and water (25 mL). The organic layer was separated, washed with brine (1×25 mL), dried over magnesium sulfate, filtered and concentrated to give the crude product ($(M+H)^+=488$) which was used without purification for the following step.

Step 11: Preparation of 3-(2-chlorophenyl)-6-(2,4-difluorophenoxy)-4-methyl-1,4-dihydro-pyrazolo[4,3-b]pyridin-5-one

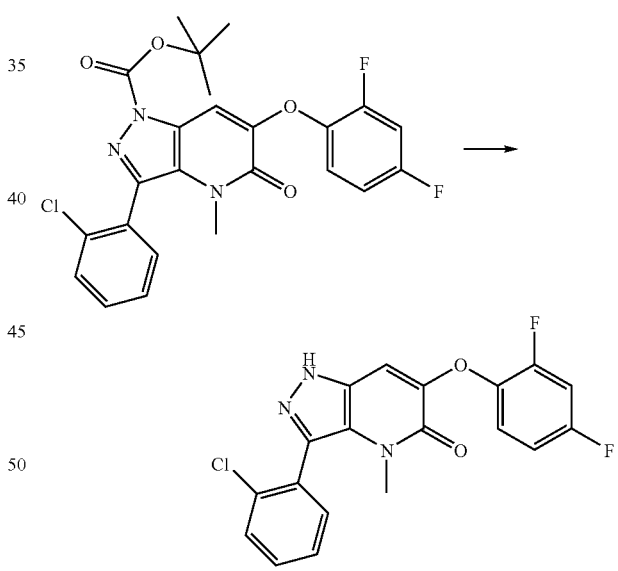

A mixture of the crude 3-(2-chlorophenyl)-6-(2,4-difluorophenoxy)-4-methyl-5-oxo-4,5-dihydro-pyrazolo[4,3-b]pyridine-1-carboxylic acid tert-butyl ester (0.0298 mmol) in a solution of 0.5 M sodium methoxide in methanol (Aldrich) (7 mL) was stirred at room temperature for 1 hour. The solvent was removed under reduced pressure at 55° C., and the resulting residue was diluted with ethyl acetate (35 mL) and water (25 mL). The organic layer was separated, washed with brine (1×25 mL), dried over magnesium sulfate, filtered, concentrated, and purified by Preparative Thin Layer Chromatography eluting with 60% ethyl acetate in hexanes to give the title compound (5.2 mg, $(M+H)^+=388$) as a white powder.

Example 3

This example illustrates a synthesis of pyridine-2-carboxylic acid [3-(2-chloro-phenyl)-6-(2,4-difluoro-phenoxy)-1H-pyrazolo[3,4-d]pyrimidin-4-yl]-amide.

Step 1 Preparation of 3-(2-chloro-phenyl)-6-methylsulfanyl-1H-pyrazolo[3,4-d]pyrimidin-4ylamine

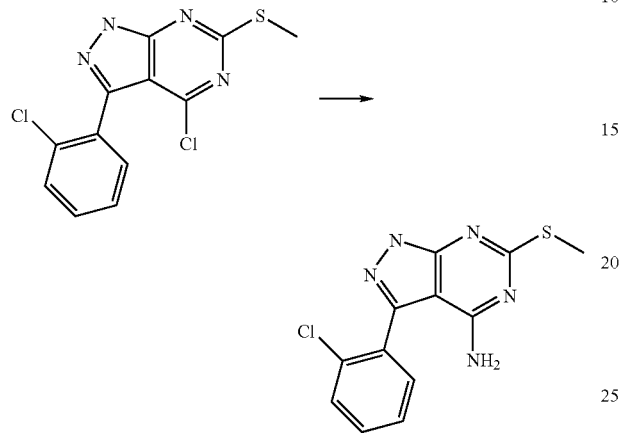

200 mg of 4-chloro-3-(2-chloro-phenyl)-6-methyl-1H-pyrazolo[3,4-d]pyrimidine (from step 4 of Example 1) was dissolved in 5 ml of 7N ammonia in methanol, and the solution was stirred at 80° C. over night in a sealed tube. The resulting reaction mixture was concentrated under vacuum and then extracted in 60 ml ethylacetate. The solution was washed first with water and next with brine, dried and after removing the solvent in vacuo afforded 190 mg (90%)) of 3-(2-chloro-phenyl)-6-methylsulfanyl-1H-pyrazolo[3,4-d]pyrimidin-4ylamine as a light tan solid, MS: 292 (M+H). The crude 3-(2-chloro-phenyl)-6-methylsulfanyl-1H-pyrazolo[3,4-d]pyrimidin-4ylamine was used in the next step without further purification.

Step 2 Preparation of pyridine-2-carboxylic acid [3-(2-chloro-phenyl)-6-methylsulfanyl-1H-pyrazolo[3,4-d]pyrimidin-4-yl]-amide

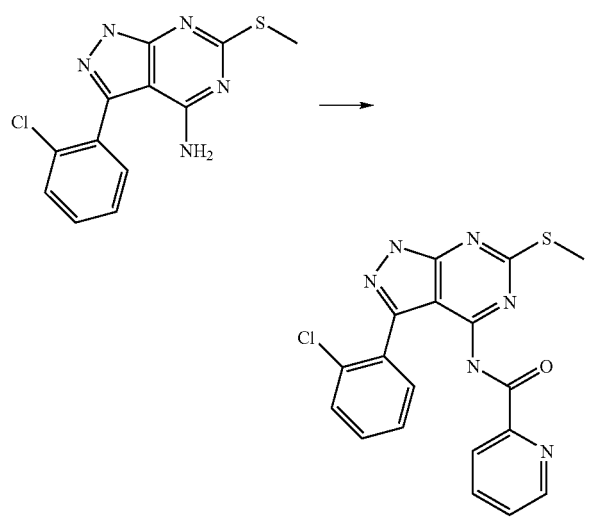

Pyridine-2-carboxylic acid (78 mg, 0.64 mmol) was placed in 5 ml thionyl chloride and refluxed for 3 hours. Excess thionyl chloride was then removed in vacuo and the crude acid chloride was suspended in 2 ml anhydrous tetrahydrofuran. The solution of acid chloride was added to a mixture of 3-(2-chloro-phenyl)-6-methylsulfanyl-1H-pyrazolo[3,4-d]pyrimidin-4-ylamine (190 mg, 0.64 mmol) and diisopropylamine (247 mg, 1.92 mmol) in 6 ml anhydrous tetrahydrofuran. The reaction mixture was refluxed for 15 h. After cooling to room temperature the resulting mixture was partition between 60 ml ethylacetate and 15 ml brine. The organic layer was washed 3 times with 3N HCl, next with saturated sodium bicarbonate solution and brine. After drying with sodium sulfate and solvent evaporation in vacuo, 140 mg of pyridine-2-carboxylic acid [3-(2-chloro-phenyl)-6-methylsulfanyl-1H-pyrazolo[3,4-d]pyrimidin-4-yl]-amide, MS: 397.1 (M+H), was obtained.

Step 3 Preparation of pyridine-2-carboxylic acid [3-(2-chloro-phenyl)-6-methanesulfonyl-1H-pyrazolo[3,4-d]pyrimidin-4-yl-amide

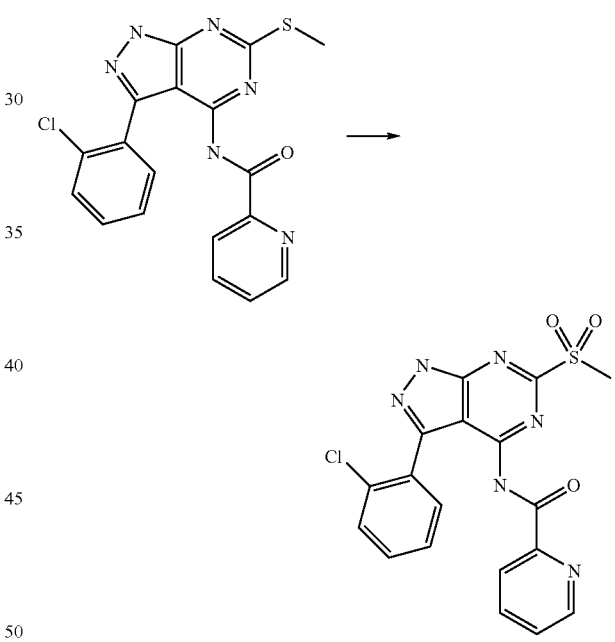

Pyridine-2-carboxylic acid [3-(2-chloro-phenyl)-6-methylsulfanyl-1H-pyrazolo{3,4pyrimidin-4-yl}-amide (140 mg, 0.35 mmol) was dissolved in 9 ml tetrahydrofuran and 3 ml methanol. To this solution was added m-chloroperbenzoic acid [190 mg (77%), 0.84 mmol]. The mixture was stirred at temperature 4 h. The reaction mixture was taken into 60 ml ethylacetate, washed 3 times with saturated sodium bicarbonate solution and 1 time with brine. After drying of the organic layer with sodium sulfate and removing of solvents in vacuo 105 mg of crude pyridine-2-carboxylic acid [3-(2-chlorophenyl)-6-methanesulfonyl-1H-pyrazolo[3,4-d]pyrimidin-4-yl-amide, MS: 429.1 (M+H), was obtained and used without further purification in the next step.

Step 4 Preparation of pyridine-2-carboxylic acid [3-(2-chloro-phenyl)-6-(2,4-difluoro-phenoxy)-1H-pyrazolo[3,4-d]pyrimidin-4-yl]-amide

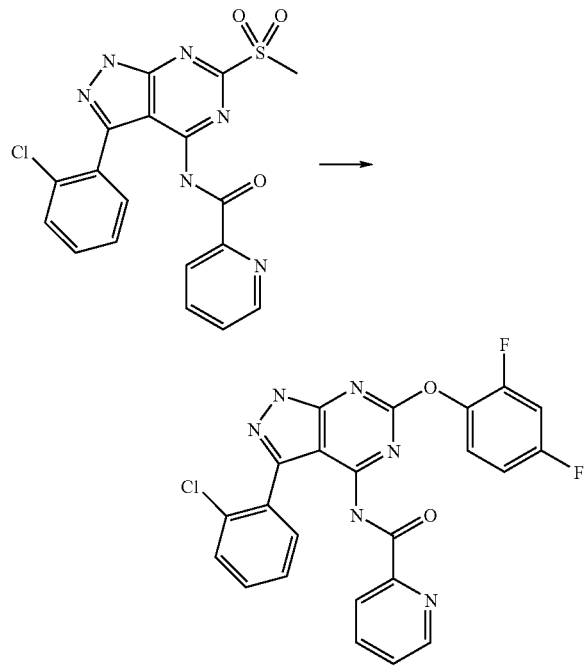

To pyridine-2-carboxylic acid[3-2(2-chloro-phenyl)-6-methanesulfonyl-1H-pyrazolo[3,4-d]pyrimidin-4-yl]-amide (105 mg, 0.24 mmol) in anhydrous NMP (2 ml) was added anhydrous potassium carbonate (25 mg, 0.18 mmol) and 2,4-difluoro-phenol (47 mg, 0.36 mmol) in 0.5 ml NMP. The mixture was heated 2 h at 120° C. After cooling the reaction mixture was partition between 50 ml ethylacetate and 20 ml brine. The organic layer was washed 2 more times with brine, dried with sodium sulfate and concentrated in vacuo. The crude mixture was chromtographed twice using first 5% methanol in methylen chloride and next 50% ethylactate in hexane, to afford 18 mg of the title compound as a white solid, MS: 479 (M+H).

Additional compounds prepared according to the above example are shown in Table 1.

Example 4

This example illustrates a synthesis of (R)-1-[6-(2,4-Difluoro-phenoxy)-3-(2-ethoxy-5-fluoro-phenyl)-1H-pyrazolo[3,4-d]pyrimidin-4-ylamino]-propan-2-ol Step 1. Preparation of 4,6-Dichloro-2-methylsulfsanyl-pyrimidine-5-carbaldehyde

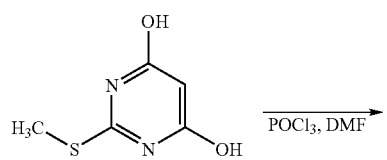

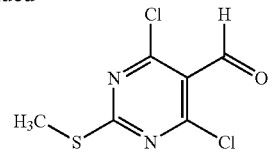

Phosphorous oxychloride (213 mL, 2.3 mol) was cooled in a sodium chloride-water ice bath to 1.8° C. under nitrogen. Dimethyl formamide (71.4 mL, 0.92 mol) was added dropwise over 45 minutes with stirring. The reaction mixture was allowed to warm up to room temperature and was stirred at room temperature for 30 minutes, and followed by stirring at 40° C. for 20 minutes. The reaction mixture was then heated to 57° C., and 2-Methylsulfanyl-pyrimidine-4,6-diol (50.0 g, 0.307 mol) was added in 5.0 g portions over 90 minutes. The reaction mixture was stirred for one hour at 55° C., and then heated to 110° C. with stirring for 17.5 hours. The reaction mixture was cooled and volatiles were removed under reduced pressure. The residue was poured into one lire of ice water. The resulting precipitate was isolated by filtration, washed with water, then with heptanes, and was dried to provide 25.2 g of crude 4,6-Dichloro-2-methylsulfanyl-pyrimidine-5-carbaldehyde. Mass Spec. M+H=224.

Step 2. Preparation of 4-Chloro-6-methylsulfanyl-1H-pyrazolo[3,4-d]pyrimidine

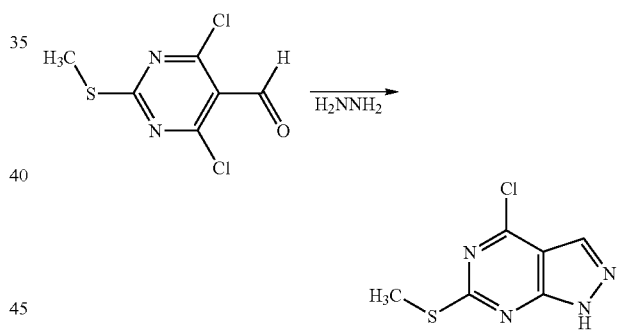

4,6-Dichloro-2-methylsulfanyl-pyrimidine-5-carbaldehyde (7.54 g, 0.0338 mol) was added to 80 mL of dioxane and stirred for 10 minutes at room temperature. Diisopropyl ethylamine (6.03 mL, 0.0340 mol) was added and the mixture was cooled in an ice bath with stirring for 10 minutes. Anhydrous hydrazine (1.08 mL, 0.0338 mmol) was added dropwise over three minutes, and stirring was continued for an additional five minutes. The ice bath was removed, and the reaction mixture was heated to reflux with stirring for two hours. The reaction mixture was then stirred at room temperature for 16 hours. The reaction mixture was concentrated under reduced pressure, and the residue was added to 20 mL of 2 N HCl and 100 mL EtOAc. The resulting suspension was stirred and filtered, ad the solid was washed with water followed by EtOAc. The organic phase of the filtrate was collected, and the aqueous phase was extracted three times with 150 mL EtOAc. The combined organic phases were dried (MgSO$_4$), filtered, and the filtrate was evaporated under reduced pressure. The resulting solid was washed with diethyl ether/hexanes (1:1) and the solid was dried to provide 3.13 g of crude 4-Chloro-6-methylsulfanyl-1H-pyrazolo[3,4-d]pyrimidine. Mass Spec. M+H=201.

Step 3. Preparation of 4-Chloro-6-methylsulfanyl-1-(2-trimethylsilanyl-ethoxymethyl)-1H-pyrazolo[3,4-d]pyrimidine

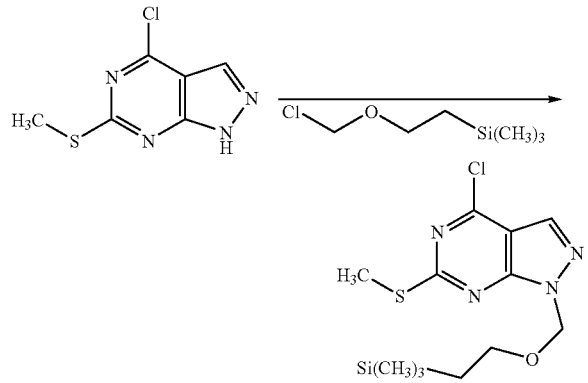

4-Chloro-6-methylsulfanyl-1H-pyrazolo[3,4-d]pyrimidine (497 mg, 2.477 mmol) was dissolved in 5 mL dry DMF, and the reaction mixture was cooled to 0° C. Sodium hydride (109 mg of 60% suspension in mineral oil) was added, and the reaction mixture was stirred for five minutes. (2-Chloromethoxy-ethyl)-trimethyl-silane (0.52 mL, 2.922 mmol) was then aded, and the reaction mixture was stirred for 10 minutes. The reaction mixture was quenched by addition to water, and was partitioned between water and ethyl acetate. The organic layer was separated, dried over MgSO$_4$, filtered, and evaporated under reduced pressure. The residue was purified via flash chromatography using 5% EtOAc in hexanes to give 391 mg of 4-Chloro-6-methylsulfanyl-1-(2-trimethylsilanyl-ethoxymethyl)-1H-pyrazolo[3,4-d]pyrimidine.

Step 4. Preparation of (R)-1-[6-Methylsulfanyl-1-(2-trimethylsilanyl-ethoxymethyl)-1H-pyrazolo[3,4-d]pyrimidin-4-ylamino]-propan-2-ol

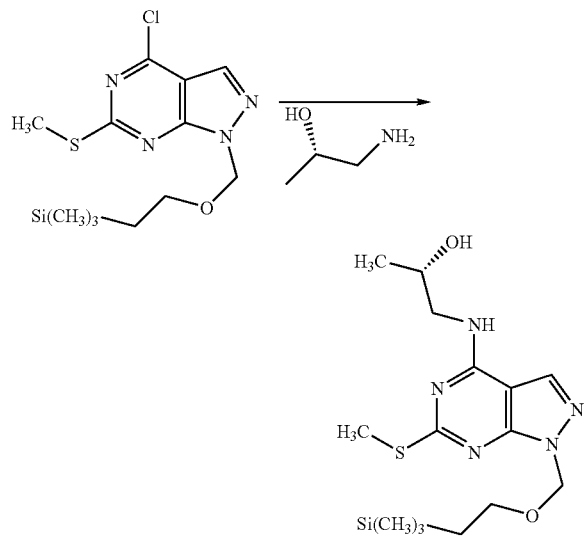

4-Chloro-6-methylsulfanyl-1-(2-trimethylsilanyl-ethoxymethyl)-1H-pyrazolo[3,4-d]pyrimidine (391 mg, 1.182 mmol) was dissloved in 5 mL of dry THF. Triethylamine (239 mg, 2.363 mmol) was added, and the reaction mixture was stirred for four hours. (S)-1-Amino-propan-2-ol (93 mg, 1.241 mmol) was then added, and the reaction mixture was stirred for 64 hours. The reaction mixture was quenched by addition to water, and was partitioned between water and ethyl acetate. The organic layer was separated, dried over MgSO$_4$, filtered, and evaporated under reduced pressure to give (R)-1-[6-Methylsulfanyl-1-(2-trimethylsilanyl-ethoxymethyl)-1H-pyrazolo[3,4-d]pyrimidin-4-ylamino]-propan-2-ol (469 mg). Mass Spec. M+H=370.

Step 5. Preparation of (R)-1-[6-Methanesulfonyl-1-(2-trimethylsilanyl-ethoxymethyl)-1H-pyrazolo[3,4-d]pyrimidin-4-ylamino]-propan-2-ol

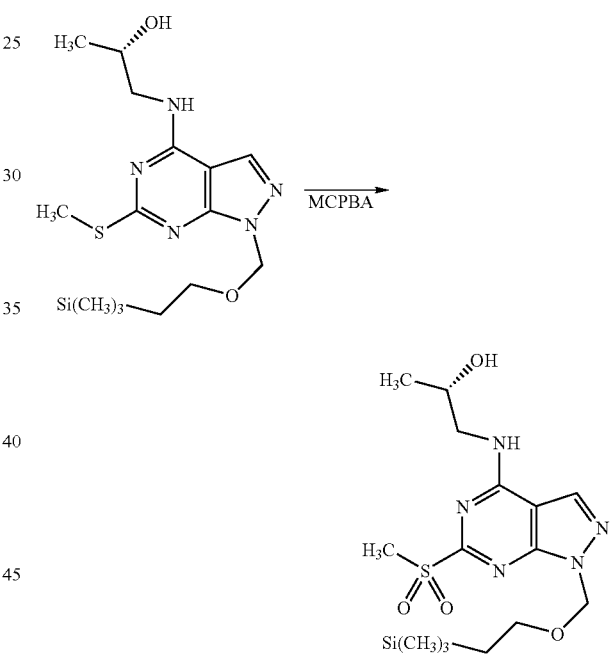

1-[6-Methylsulfanyl-1-(2-trimethylsilanyl-ethoxymethyl)-1H-pyrazolo[3,4-d]pyrimidin-4-ylamino]-propan-2-ol (456 mg, 1.239 mmol) was dissolved in a mixture of 6 mL of THF and 2 mL MeOH. Meta-chloro perbenzoic acid (447 mg of 77% MCPBA, 2.592 mmol) was added, and the reaction mixture was stirred for two hours. The reaction mixture was quenched by addition to water, and was partitioned between water and ethyl acetate. The organic layer was separated, dried over MgSO$_4$, filtered, and evaporated under reduced pressure to give 529 mg of (R)-1-[6-Methanesulfonyl-1-(2-trimethylsilanyl-ethoxymethyl)-1H-pyrazolo[3,4-d]pyrimidin-4-ylamino]-propan-2-ol. Mass Spec. M+H=402.

Additional compounds prepared according to the above example are shown in Table 1.

Step 6. Preparation of (R)-1-[6-(2,4-Difluoro-phenoxy)-1-(2-trimethylsilanyl-ethoxymethyl)-1H-pyrazolo[3,4-d]pyrimidin-4-ylamino]-propan-2-ol

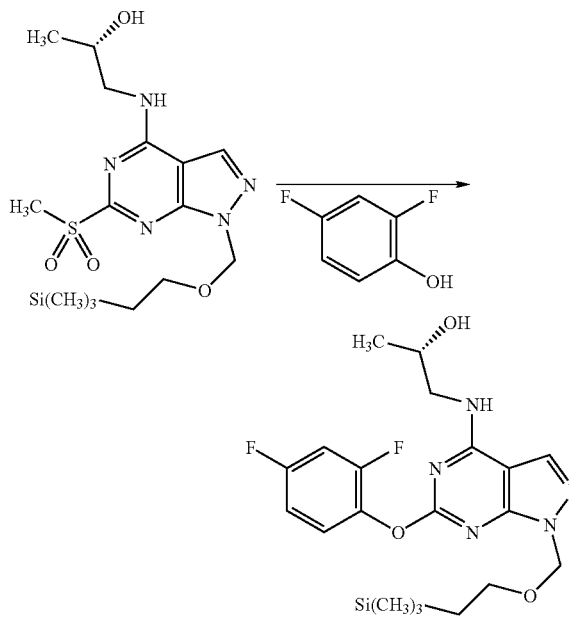

2,4-Difluorophenol (510 mg, 3.922 mmol) was dissolved in 5 mL dry DMF, and sodium hydride (152 mg of 60% suspension in mineral oil, 3.791 mmol) was added. The reaction mixture was stirred for 25 minutes, and then (R)-1-[6-Methanesulfonyl-1-(2-trimethylsilanyl-ethoxymethyl)-1H-pyrazolo[3,4-d]pyrimidin-4-ylamino]-propan-2-ol (525 mg, 1.307 mmol) was added. The reaction mixture was heated to 100° C. for four hours with stirring, then was stirred for 16 hours at room temperature. The reaction mixture was quenched by addition to water, and was partitioned between water and ethyl acetate. The organic layer was separated, dried over MgSO₄, filtered, and evaporated under reduced pressure. The residue was purified by flash chromatography (8% MeOH in methylene chloride) to give 258 mg of (R)-1-[6-(2,4-Difluoro-phenoxy)-1-(2-trimethylsilanyl-ethoxymethyl)-1H-pyrazolo[3,4-d]pyrimidin-4-ylamino]-propan-2-ol. Mass Spec. M+H=452.

Step 7. Preparation of (R)-1-[6-(2,4-Difluoro-phenoxy)-1H-pyrazolo[3,4-d]pyrimidin-4-ylamino]-propan-2-ol

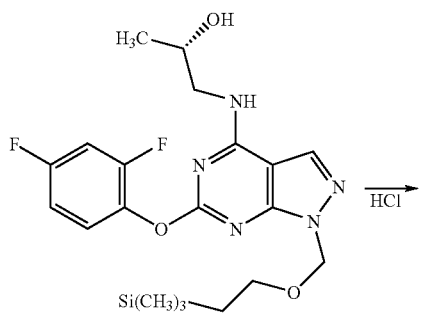

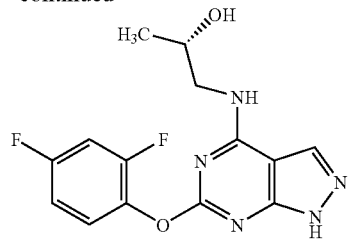

(R)-1-[6-(2,4-Difluoro-phenoxy)-1-(2-trimethylsilanyl-ethoxymethyl)-1H-pyrazolo[3,4-d]pyrimidin-4-ylamino]-propan-2-ol (258 mg) was dissolved in 8 mL MeOH, and 0.6 nL of 6M HCl was added. The reaction mixture was heated to 80° C. for 3.5 hours, then cooled. The reaction mixture was quenched by addition to water, and was partitioned between water and ethyl acetate. The organic layer was separated, dried over MgSO₄, filtered, and evaporated under reduced pressure. The residue was purified by flash chromatography (10% MeOH in methylene chloride) to give 116 mg of (R)-1-[6-(2,4-Difluoro-phenoxy)-1H-pyrazolo[3,4-d]pyrimidin-4-ylamino]-propan-2-ol. Mass Spec. M+H=322.

Step 8. Preparation of (R)-1-[6-(2,4-Difluoro-phenoxy)-3-iodo-1H-pyrazolo[3,4-d]pyrimidin-4-ylamino]-propan-2-ol

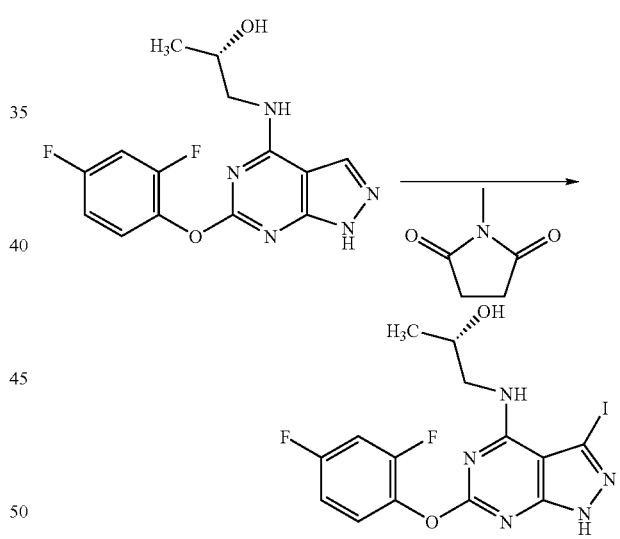

N-iodo succinimide (35 mg. 0.157 mmol) was dissolved in 3 mL of DMF, and (R)-1-[6-(2,4-Difluoro-phenoxy)-1H-pyrazolo[3,4-d]pyrimidin-4-ylamino]-propan-2-ol (42 mg, 0.131 mmol) was added. The reaction mixture was heated to 80° C. for two hours, after which an additional 35 mg of N-iodo succinimide was added. After heating for two more hours at 80° C., an additional 35 mg of N-iodo succinimide was added. The reaction mixture was heated at 80° C. for 5 more hours, then was cooled to room temperature. The reaction mixture was quenched by addition to water, and was partitioned between water and ethyl acetate. The organic layer was separated, dried over MgSO₄, filtered, and evaporated under reduced pressure to give 64 mg of 1-[6-(2,4-Difluoro-phenoxy)-3-iodo-1H-pyrazolo[3,4-d]pyrimidin-4-ylamino]-propan-2-ol. Mass Spec. M+H=448.

Step 9. Preparation of (R)-1-[6-(2,4-Difluoro-phenoxy)-3-(2-ethoxy-5-fluoro-phenyl)-1H-pyrazolo[3,4-d]pyrimidin-4-ylamino]-propan-2-ol

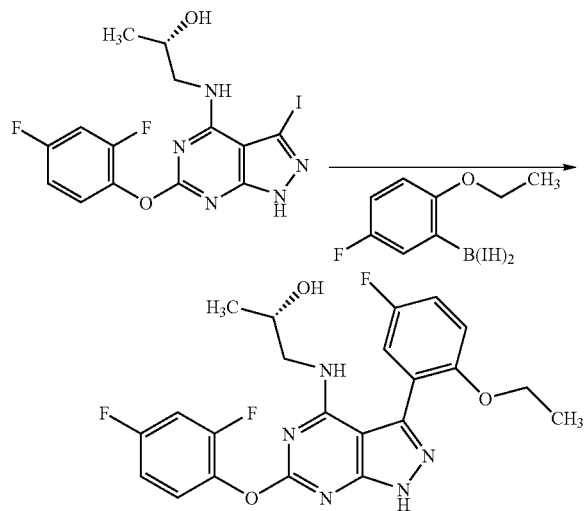

1-[6-(2,4-Difluoro-phenoxy)-3-iodo-1H-pyrazolo[3,4-d]pyrimidin-4-ylamino-propan-2-ol (200 mg, 0.447 mmol), 5-fluoro-2-ethoxyphenyl boronic acid (246 mg), K₃PO₄ (285 mg), and Tetrakis(triphenylphosphine) palladium(0) CH₂Cl₂ (73 mg) were added to 2 mL dioxane in a microwave vial. The vial was sealed and the reaction mixture was heated to 180° C. for 10 minutes. The reaction mixture was partitioned between water and ethyl acetate, and the organic layer was separated, dried over MgSO₄, filtered, and evaporated under reduced pressure. The residue was filtered through silica gel using 10% MeOH in methylene chloride, then purified by preparative scale thin layer chromatography using 10% MeOH in methylene chloride, to give 62.9 mg of (R)-1-[6-(2,4-Difluoro-phenoxy)-3-(2-ethoxy-5-fluoro-phenyl)-1H-pyrazolo[3,4-d]pyrimidin-4-ylamino]-propan-2-ol. Mass Spec. M+H=460.

Additional compounds prepared according to the above example are shown in Table 1.

Example 5

This example illustrates a synthesis of (S)-3-[3-(2-Chloro-phenyl)-6-(2,4-difluoro-phenoxy)-1H-pyrazolo[3,4-d]pyrimidin-4-yloxy]-propane-1,2-diol.

Step 1. Preparation of 3-(2-Chloro-phenyl)-4-(2,2-dimethyl-[1,3]dioxolan-4-ylmethoxy)-6-methylsulfanyl-1H-pyrazolo[3,4-d]pyrimidine

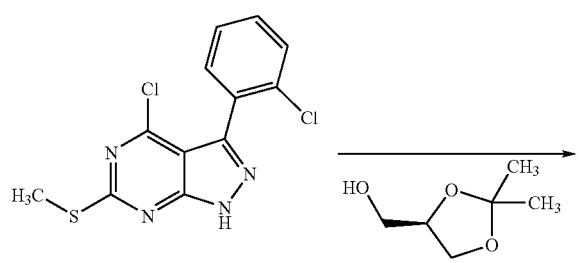

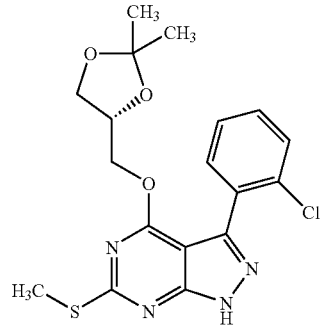

To (R)-2,2-dimethyl-1,3-dioxolane-4-ethanol (2.12 g) in 10 mL dioxane was added sodium hydride (0.656 g) at 0° C. The resulting mixture was stired for 10 minutes, and then 4-Chloro-3-(2-chloro-phenyl)-6-methylsulfanyl-1H-pyrazolo[3,4-d]pyrimidine (1.0 g, 3.213 mmol) was added. The reaction mixture was heated to reflux for one hour, then cooled to room temperature. Water (150 mL) and ethyl acetate (300 mL) was added, and the layers separated. The aqueous layer was washed four times with ethyl acetate, and the combined organic layers were washed with brine, dried over MgSO₄, filtered, and concentrated under reduced pressure. The residue was purified by flash chromatography (20% to 30% EtOAc in hexanes) to yield 1.03 g of 3-(2-Chloro-phenyl)4-(2,2-dimethyl-[1,3]dioxolan 4-ylmethoxy)-6-methylsulfanyl-1H-pyrazolo[3,4-d]pyrimidine. Mass Spec. M+H=407. Mp.=119.5-122.3° C.

Step 2. Preparation of (S)-3-(2-Chloro-phenyl)-4-(2, 2-dimethyl-[1,3]dioxolan-4-ylmethoxy)-6-methylsulfonyl-1H-pyrazolo[3,4-d]pyrimidine

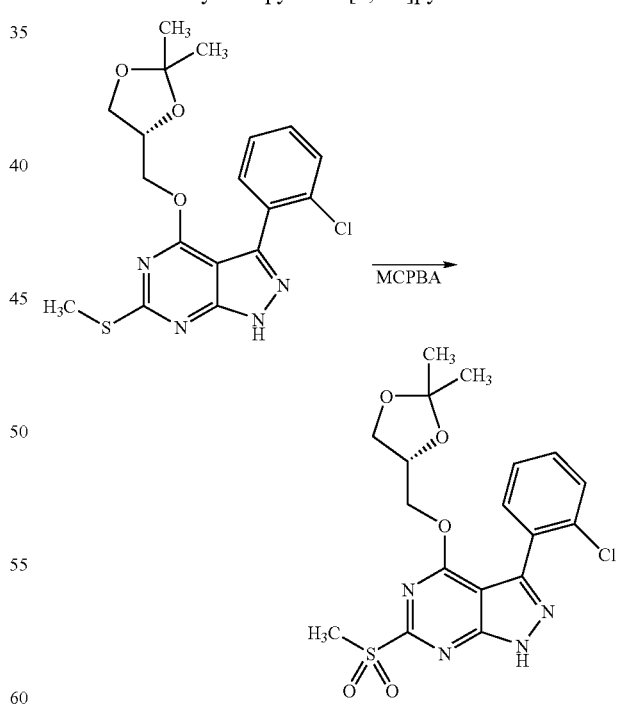

3-(2-Chloro-phenyl)-4-(2,2-dimethyl-[1,3]dioxolan-4-ylmethoxy)-6-methylsulfanyl-1H-pyrazolo[3,4-d]pyrimidine (1.2 g, 2.95 mmol) was treated with meta-chloroperbenzoic acid using the procedure of step 5 of Example 1 to provide 1.342 g of (S)-3-(2-Chloro-phenyl)-4-(2,2-dimethyl-[1,3]dioxolan-4-ylmethoxy)-6-methylsulfonyl-1H-pyrazolo[3,4-d]pyrimidine. Mass Spec. M+H=440. Mp.=161.0-162.3° C.

Step 3. Preparation of (S)-3-(2-Chloro-phenyl)-6-(2,4-difluoro-phenoxy)-4-(2,2-dimethyl-[1,3]dioxolan-4-ylmethoxy)-1H-pyrazolo[3,4-d]pyrimidine

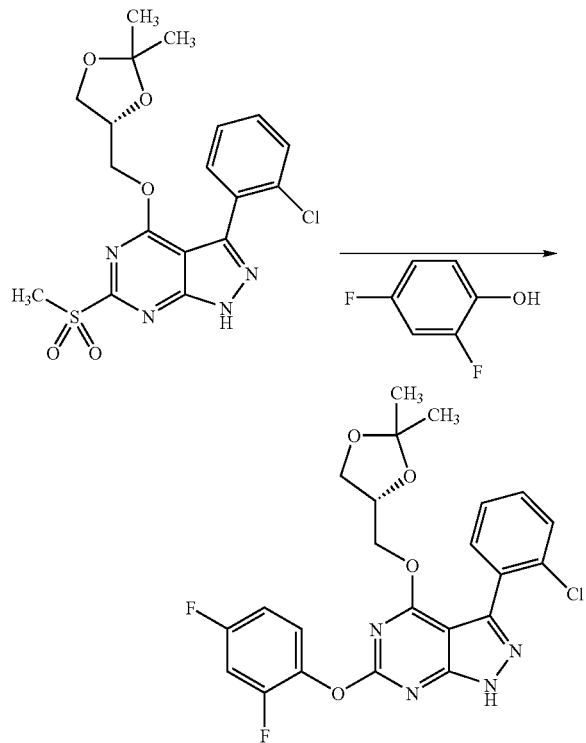

Powdered KOH (1.0 g) was taken up in 4 mL of 2,4-difluorophenol, and the resulting mixture was heated at 120° C. for 15 minutes. (S)-3-(2-Chloro-phenyl)-4-(2,2-dimethyl-[1,3]dioxolan-4-ylmethoxy)-6-methylsulfonyl-1H-pyrazolo[3,4-d]pyrimidine (1.34 g, 0.305 mmol) was added, and the reaction mixture was stirred for one hour at 120° C. The reaction mixture was cooled to room temperature, partitioned between water (100 mL) and EtOAc (300 ML0, and the layers were separated. The organic layer was washed three times with 2N aqueous NaOH, once with brine, dried over MgSO₄, filtered, and concentrated under reduced pressure. The residue was purified by preparative scale TLC (50% MeOH in methylene chloride to provide 1.395 mg of (S)-3-(2-Chloro-phenyl)-6-(2,4-difluoro-phenoxy)-4-(2,2-dimethyl-[1,3]dioxolan-4-ylmethoxy)-1H-pyrazolo[3,4-d]pyrimidine. Mass Spec. M+H=489. Mp.=70.1-75.9° C.

Step 4. Preparation of (S)-3-[3-(2-Chloro-phenyl)-6-(2,4-difluoro-phenoxy)-1H-pyrazolo[3,4-d]pyrimidin-4-yloxy]-propane-1,2-diol

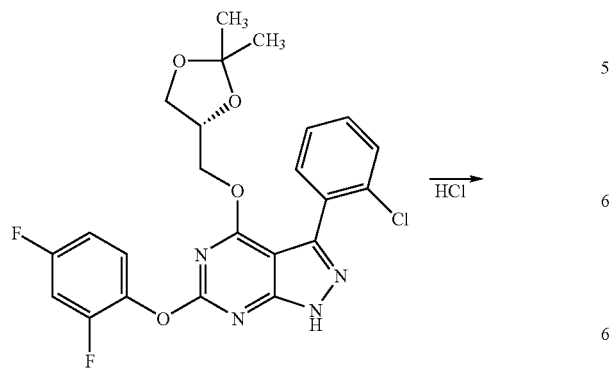

(S)-3-(2-Chloro-phenyl)-6-(2,4-difluoro-phenoxy)-4-(2,2-dimethyl-[1,3]dioxolan-4-ylmethoxy)-1H-pyrazolo[3,4-d]pyrimidine (1.395 g) was taken up in 30 mL dioxane, and 25 mL of 4N HCl was added. The reaction mixture was stirred at room temperature for 25 minutes, and then the reaction mixture was partitioned between water (100 mL) and EtOAc (300 mL). The organic phase was washed with brine, dried over MgSO₄, filtered, and concentrated under reduced pressure. The residue was eluted through silica gel with 30% EtOAc in methylene chloride to provide 886.4 mg of (S)-3-[3-(2-Chloro-phenyl)-6-(2,4-difluoro-phenoxy)-1H-pyrazolo[3,4-d]pyrimidin-4-yloxy]-propane-1,2-diol. Mass Spec. M+H=449. Mp.=179.2-181.3° C.

Additional compounds prepared according to the above example are shown in Table 1.

Example 6

This example illustrates a synthesis of C-[3-(2-Chloro-phenyl)-6-(2,4-difluoro-phenoxy)-1H-pyrazolo[3,4-d]pyrimidin-4-yl]-N,N-dimethyl-methanesulfonamide.

Step 1. Preparation of 4-Chloro-3-(2-chloro-phenyl)-6-methylsufanyl-1-(2-trimethylsilanyl-ethoxymethyl)-1H-pyrazolo[3,4-d]pyrimidine

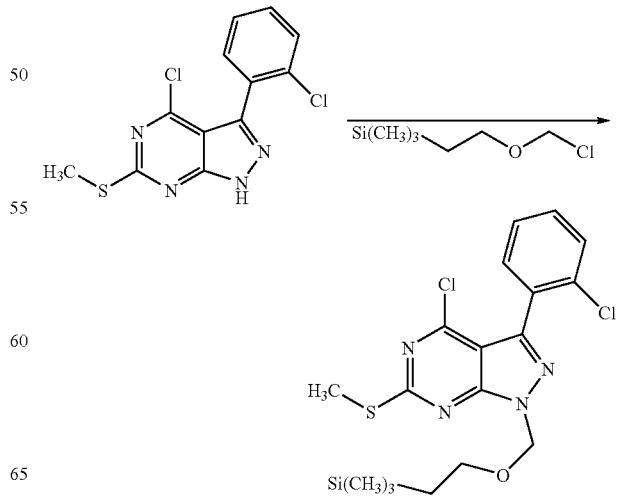

4-Chloro-3-(2-chloro-phenyl)-6-methylsulfanyl-1H-pyrazolo[3,4-d]pyrimidine (10.0 g, 0.032 mol) was added to 100 mL of dry DMF, and the resulting solution was cooled to 0° C. (2-Chloromethoxy-ethyl)-trimethyl-silane (6.8 mL, 0.038 mol) was added dropwise, and the reaction mixture was stirred for five minutes. Sodium hydride (1.40 g, 0.0333 mol) was then added, and the reaction mixture was stirred for 30 minutes at 0° C. The reaction mixture was partitioned between water and ethyl acetate. The layers were separated, and the aqueous layer was washed twice with ethyl acetate. The combined organic layers were washed with brine, washed with water, dried over MgSO₄, filtered, and concentrated under reduced pressure. The residue was purified by flash chromatography (0% to 10% hexanes in EtOAc) to afford 8.55 g of 4-Chloro-3-(2-chloro-phenyl)-6-methylsulfanyl-1-(2-trimethylsilanyl-ethoxymethyl)-1H-pyrazolo[3,4-d]pyrimidine.

Step 2. Preparation of C-[3-(2-Chloro-phenyl)-6-methylsulfanyl-1-(2-trimethylsilanyl-ethoxymethyl)-1H-pyrazolo[3,4-d]pyrimidin-4-yl]-N,N-dimethyl-methanesulfonamide

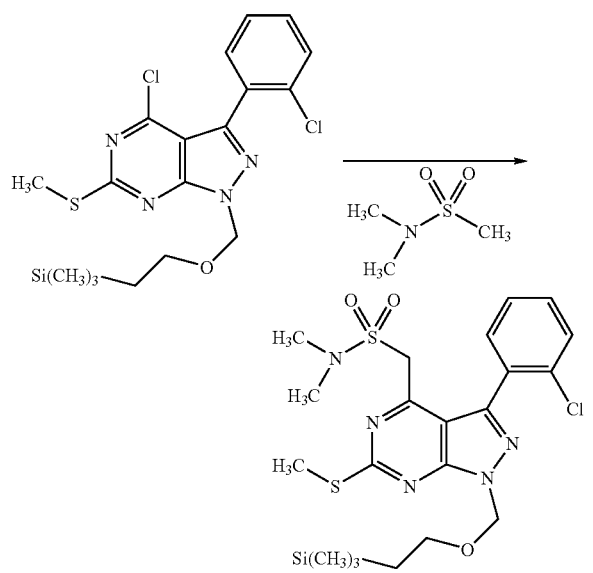

To a solution of N,N-dimethyl methanesulfonamide (419 mg, 3.40 mmol) in 5 mL dry THF at 5° C. was added n-BuLi (2.2 mL of 1.6M solution in hexanes 3.50 mmol) dropwise. To this stirring solution was added dropwise a solution of 4-Chloro-3-(2-chloro-phenyl)-6-methylsulfanyl-1-(2-trimethylsilanyl-ethoxymethyl)-1H-pyrazolo[3,4-d]pyrimidine (0.500 g, 1.13 mmol) in 1 mL dry THF. The reaction mixture was stirred for 2 hours and allowed to warm to room temperature during this time. The reaction was quenched by addition of 10 mL water and 1 mL of 1.2M HCl, and the resulting aqueous solution was extracted twice with 20 mL methylene chloride. The combined organic layers were dried over MgSO₄, filtered, and concentrated under reduced pressure. The residue was purified by flash chromatography (0% to 30% EtOAc in hexanes) to give 421 mg of C-[3-(2-Chloro-phenyl)-6-methylsulfanyl-1-(2-trimethylsilanyl-ethoxymethyl)-1H-pyrazolo[3,4-d]pyrimidin-4-yl]-N,N-dimethyl-methanesulfonamide.

Step 3. Preparation of C-[3-(2-Chloro-phenyl)-6-methanesulfonyl-1-(2-trimethylsilanyl-ethoxymethyl)-1H-pyrazolo[3,4-d]pyrimidin-4-yl]-N,N-dimethyl-methanesulfonamide

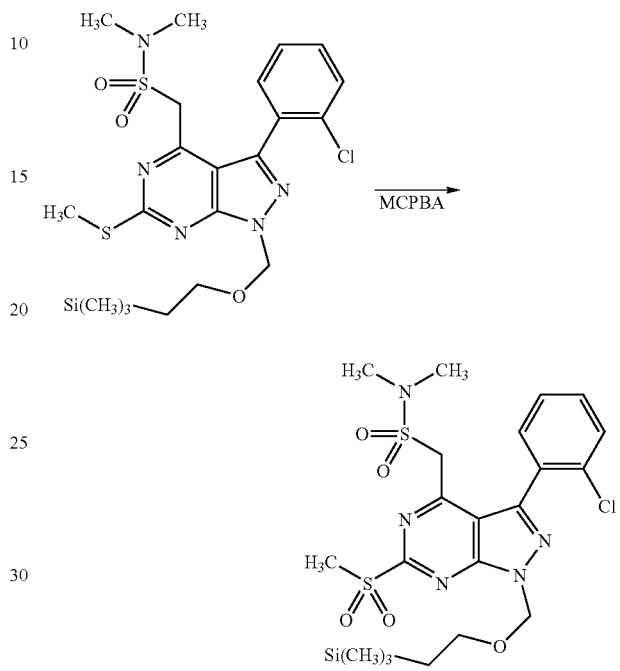

C-[3-(2-Chloro-phenyl)-6-methylsulfanyl-1-(2-trimethylsilanyl-ethoxymethyl)-1H-pyrazolo[3,4-d]pyrimidin-4-yl]-N,N-dimethyl-methanesulfonamide (421 mg, 0.997 mmol) was treated with meta-chloroperbenzoic acid using the procedure of step 5 of Example 1 to provide 398 mg of C-[3-(2-Chloro-phenyl)-6-methylsulfonyl-1-(2-trimethylsilanyl-ethoxymethyl)-1H-pyrazolo[3,4-d]pyrimidin-4-yl]-N,N-dimethyl-methanesulfonamide. Mass Spec. M+H=560.

Step 4. Preparation of C-[3-(2-Chloro-phenyl)-6-(2,4-difluoro-phenoxy)-1-(2-trimethylsilanyl-ethoxymethyl)-1H-pyrazolo[3,4-d]pyrimidin-4-yl]-N,N-dimethyl-methanesulfonamide

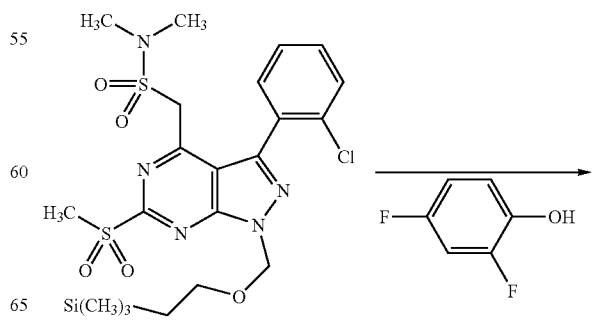

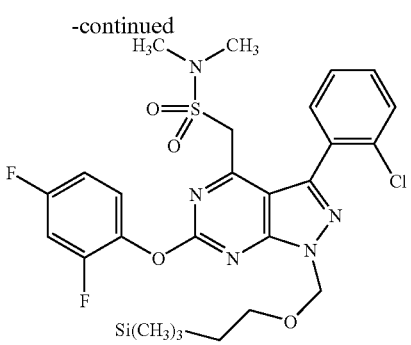

C-[3-(2-Chloro-phenyl)-6-methylsulfonyl-1-(2-trimethylsilanyl-ethoxymethyl)-1H-pyrazolo[3,4-d]pyrimidin-4-yl]-N,N-dimethyl-methanesulfonamide (398 mg) was treated with 2,4-difluorophenol in the presence of KOH using the procedure of step 6 of Example 4 to afford 287 mg of C-[3-(2-Chloro-phenyl)-6-(2,4-difluoro-phenoxy)-1-(2-trimethylsilanyl-ethoxymethyl)-1H-pyrazolo[3,4-d]pyrimidin-4-yl]-N,N-dimethyl-methanesulfonamide. Mass Spec. M+H=610.

Step 5. Preparation of C-[3-(2-Chloro-phenyl)-6-(2,4-difluoro-phenoxy)-1H-pyrazolo[3,4-d]pyrimidin-4-yl]-N,N-dimethyl-methanesulfonamide

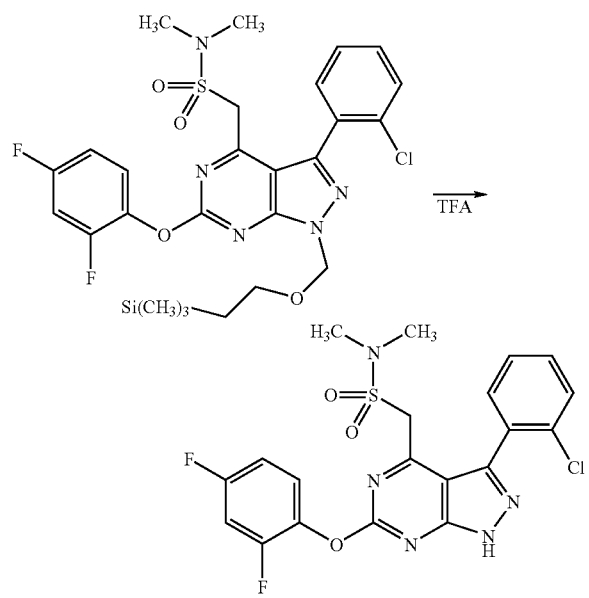

C-[3-(2-Chloro-phenyl)-6-(2,4-difluoro-phenoxy)-1-(2-trimethylsilanyl-ethoxymethyl)-1H-pyrazolo[3,4-d]pyrimidin-4-yl]-N,N-dimethyl-methanesulfonamide (273 mg, 0.447 mmol) was dissolved in 5 mL chloroform, and 2.5 mL of trifluoroacetic acid was added. The reaction mixture was stirred for 22 hours at room temperature, and was then concentrated to dryness under reduced pressure. The residue was dissolved in 7 mL of MeOH, and sodium borohydride (109 mg, 4.47 mmol) was added. The reaction mixture was stirred for 15 minutes, then concentrated under reduced pressure. The residue was partitioned between 100 mL EtOAc and 100 mL brine, and the organic layer was separated, dried (MgSO$_4$), filtered and concentrated under reduced pressure. The residue was purified via flash chromatography (0% to 40% EtOAc in hexanes) to yield 167 mg of C-[3-(2-Chloro-phenyl)-6-(2,4-difluoro-phenoxy)-1H-pyrazolo[3,4-d]pyrimidin-4-yl]-N,N-dimethyl-methanesulfonamide. Mass Spec. M+H=481.

Additional compounds prepared according to the above example are shown in Table 1.

Example 7

This example illustrates a synthesis of (R)-1-[3-Cyclopentyl-6-(2,4-difluoro-phenoxy)-1H-pyrazolo[3,4-d]pyrimidin-4-ylamino]-propan-2-ol.

Step 1. Preparation of Cyclopentyl-(4,6-dichloro-2-methylsulfanyl-pyrimidin-5-yl)-methanol

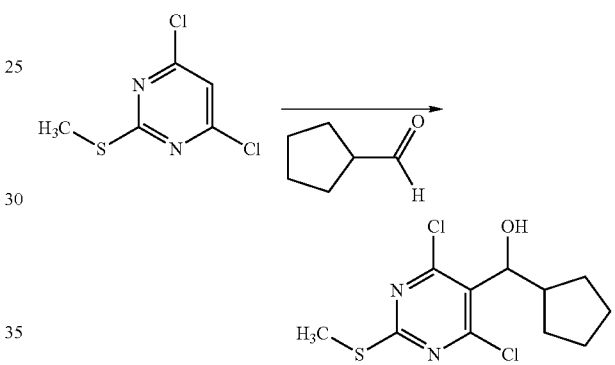

4,6-Dichloro-2-methylsulfanyl-pyrimidine (8.0 g, 41.01 mmol) was dissolved in 500 mL dry THF and cooled to −78° C. Lithium diusopropylamine (36.9 mL of 2.0 M solution in hexanes) was added dropwise, and the reaction mixture was stirred for 20 minutes at −78° C. Cyclopentane-carboxaldehyde (8.05 g, 82.02 mmol was added, and the reaction mixture was stirred for 45 minutes at −78° C. The reaction was quenched by addition of saturated aqueous ammonium chloride. The aqueous mixture was extracted with ethyl acetate, and the combined organic layers were washed with water, washed with brine, dried (MgSO$_4$), filtered, and evaporated under reduced pressure. The residue was purified by flash chromatography (5% to 40% EtOAc in hexanes) to yield 9.76 g of cyclopentyl-(4,6-dichloro-2-methylsulfanyl-pyrimidin-5-yl)-methanol. Mass Spec. M+H=294.

Step 2. Preparation of Cyclopentyl-(4,6-dichloro-2-methylsulfanyl-pyrimidin-5-yl)-methanone

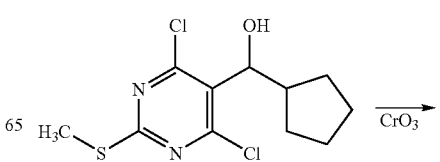

-continued

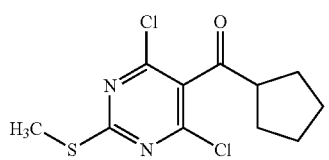

Cyclopentyl-(4,6-dichloro-2-methylsulfanyl-pyrimidin-5-yl)-methanol (8.1 g, 27.62 mmol) was dissolved in 100 mL dry acetone and stirred under nitrogen at 0° C. CrO₃ (11.05 g, 110.497 mmol) was added in portions over three minutes. The reaction mixture was stirred for 20 minutes. The reaction was quenched by addition of 15 mL isopropanol, followed by basificaction with saturated aqueous sodium bicarbonate. The resulting solution was filtered through Celite, and the Celite was washed with acetone. The resulting solution was dried over Na₂SO₄, filtered, and concentrated under reduced pressure to give 3.1 g of Cyclopentyl-(4,6-dichloro-2-methylsulfanyl-pyrimidin-5-yl)-methanone. Mass Spec. M+H=292.

Step 3. Preparation of 4-Chloro-3-cyclopentyl-6-methylsulfanyl-1H-pyrazolo[3,4-d]pyrimidine

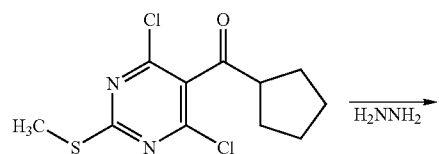

Cyclopentyl-(4,6-dichloro-2-methylsulfanyl-pyrimidin-5-yl)-methanone (2.0 g, 6.868 mmol) was dissolved in 25 mL dry THF and stirred at 0° C. under nitrogen. N,N-diisopropylethylamine (2.392 mL, 13.763 mmol) was added dropwise, and the reaction mixture was stirred for five minutes. Hydrazine (0.205 mL, 6.525 mmol) was added dropwise, and the reaction was stirred for 16 hours, during which time the reaction mixture was allowed to warm to room temperature. The reaction mixture was partitioned between water and ethyl acetate, and the organic phase was separated, washed with water, washed with brine, dried (MgSO₄), filtered and evaporated under reduced pressure to give 2.09 g of 4-Chloro-3-cyclopentyl-6-methylsulfanyl-1H-pyrazolo[3,4-d]pyrimidine. Mass Spec. M+H=270.

Step 3. Preparation of (R)-1-(3-Cyclopentyl-6-methylsulfanyl-1H-pyrazolo[3,4-d]pyrimidin-4-ylamino)-propan-2-ol

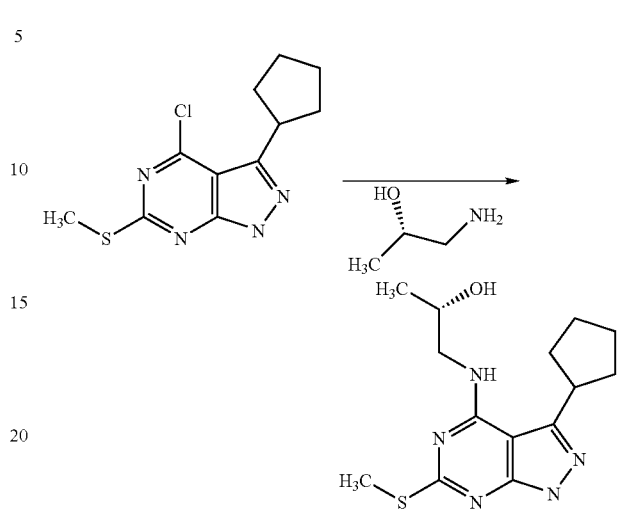

4-Chloro-3-cyclopentyl-6-methylsulfanyl-1H-pyrazolo[3,4-d]pyrimidine (500 mg, 1.860 mmol) was dissolved in 25 mL dry THF, and (S)-1-Amino-propan-2-ol (1.758 mL, 22.32 mmol) was added. The reaction mixture was heated to reflux for three hours, then cooled to room temperature. The reaction mixture was partitioned between water and ethyl acetate, and the organic phase was separated, washed with water, washed with brine, dried (MgSO₄), filtered and evaporated under reduced pressure to give 0.56 g of (R)-1-(3-Cyclopentyl-6-methylsulfanyl-1H-pyrazolo[3,4-d]pyrimidin-4-ylamino)-propan-2-ol. Mass Spec. M+H=309.

Step 4. Preparation of (R)-1-(3-Cyclopentyl-6-methylsulfonyl-1H-pyrazolo[3,4-d]pyrimidin-4-ylamino)-propan-2-ol

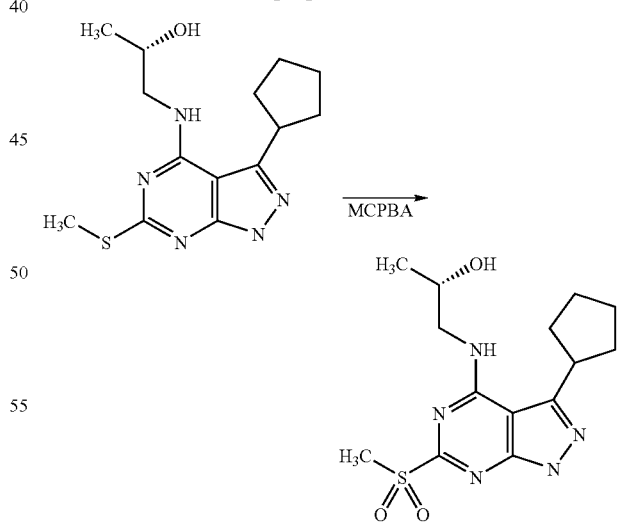

(R)-1-(3-Cyclopentyl-6-methylsulfanyl-1H-pyrazolo[3,4-d]pyrimidin-4-ylamino)-propan-2-ol was treated with meta-chloroperbenzoic acid using the procedure of step 5 of Example 1 to provide 0.60 g of (R)-1-(3-Cyclopentyl-6-methylsulfonyl-1H-pyrazolo[3,4-d]pyrimidin-4-ylamino)-propan-2-ol. Mass Spec. M+H=340.

Step 5. Preparation of (R)-1-[3-Cyclopentyl-6-(2,4-difluoro-phenoxy)-1H-pyrazolo[3,4-d]pyrimidin-4-ylamino]-propan-2-ol

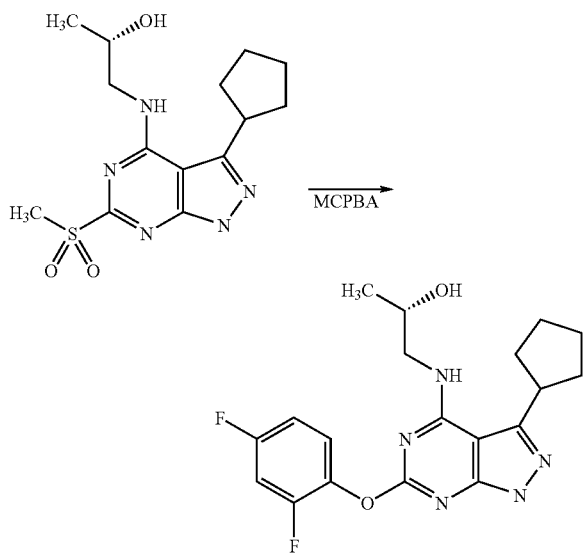

(R)-1-(3-Cyclopentyl-6-methylsulfonyl-1H-pyrazolo[3,4-d]pyrimidin-4-ylamino)-propan-2-ol was treated with 2,4-difluorophenol in the presence of KOH using the procedure of step 6 of Example 4 to afford 0.56 mg of (R)-1-[3-Cyclopentyl-6-(2,4-difluoro-phenoxy)-1H-pyrazolo[3,4-d]pyrimidin-4-ylamino]-propan-2-ol. Mass Spec. M+H=390.

Example 8

This example illustrates a synthesis of (R)-1-[3-(2-Chlorophenyl)-6-(2,4-difluoro-phenoxy)-1H-pyrazolo[3,4-b]pyrazin-5-ylamino]-propan-2-ol.

Step 1. Preparation of (2-chlorophenyl)-(3,5-dichloropyrazin-2-yl)-methanol.

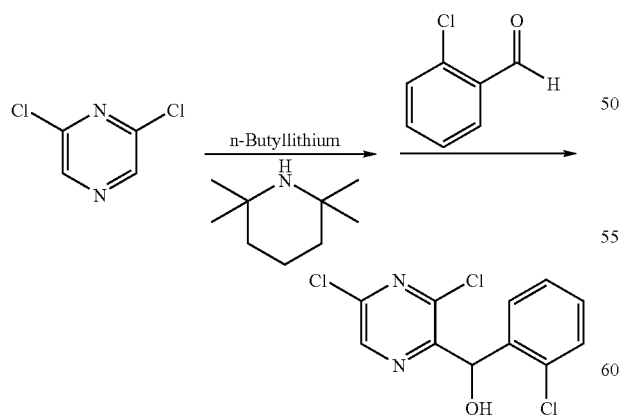

To a −20° C. solution of n-butyllithium (2.5 M in hexane, Aldrich, 26.5 mmol) in dry tetrahydrofuran (200 mL) under argon was added 2,2,6,6-tetramethylpiperidine (Aldrich, 11.5 mL, 66.5 mmol, 1.22 eq). The resulting solution was warmed to 0° C. over 0.5 hour period. The solution was then cooled to −78° C., and a solution of 2,6-dichloropyrazine (Aldrich, 8.24 g, 55.3 mmol, 1.0 eq) in tetrahydrofuran was slowly added via a syringe. After addition was complete, the resulting mixture was stirred at −78° C. for an additional 1 hour after which 2-chlorobenzaldehyde (Aldrich, 9.3 mL, 83 mmole, 1.5 eq) was added drop wise via a syringe. The reaction mixture was stirred for an additional 1 hour, quenched with hydrochloric acid (18 mL, 220 mmol, 4 eq)/ethanol (75 mL)/tetrahydrofuran (90 mL) mixture, and then warmed to room temperature. The reaction mixture was diluted with aqueous saturated sodium bicarbonate solution and extracted with ether. The organic layer was separated and washed with brine, dried over sodium sulfate, filtered, and concentrated to give a crude oil which was purified via chromatography using dichloromethane/hexanes (1:1) as the eluent to give (2-chlorophenyl)-(3,5-dichloropyrazin-2-yl) methanol (12.8 g, 44 mmol, 80% yield). Mass spec M+1=290.

Step 2. Preparation of (2-chlorophenyl)-(3,5-dichloropyrazin-2-yl)methanone

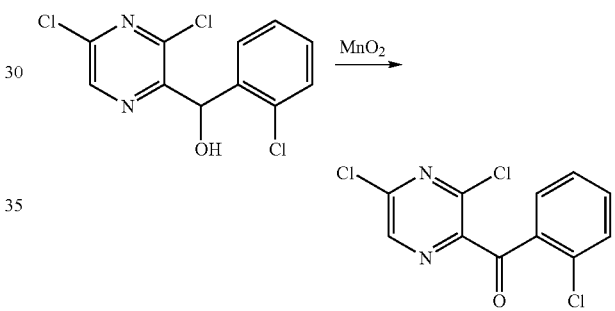

To a dichloromethane solution of (2-chlorophenyl)-(3,5-dichloropyrazin-2-yl)methanol (7.1 g, 24.5 mmol) was added portion wise solid manganese (IV) oxide (25 g, 245 mmol) and the resulting mixture was stirred at room temperature overnight. The reaction mixture was filtered and the filtrate was concentrated to give (2-chlorophenyl)-(3,5-dichloropyrazin-2-yl)methanone (6.02 g, 21 mmol, 85% yield). Mass spec., M+1=288.

Step 3. Preparation of [3-chloro-5-(2,4-difluorophenoxyl)pyrazin-2-yl]-(2-chlorophenyl)-methanone

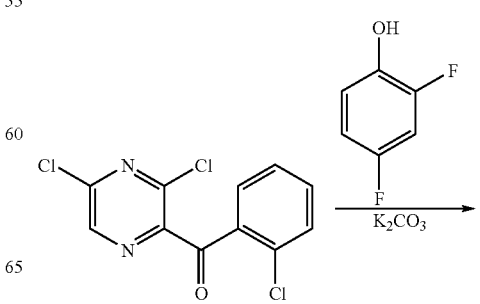

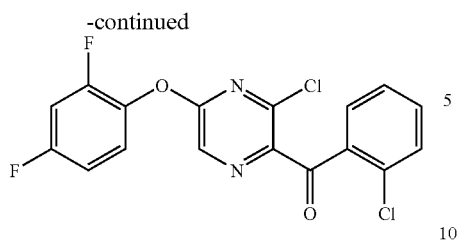

To a dimethylformamide, i.e., DMF, (25 mL) solution of (2-chlorophenyl)-(3,5-dichloropyrazin-2-yl)methanone (2.1 g, 7.3 mmol, 1.0 eq) under nitrogen was added 2,4-difluorophenol (0.7 mL, 7.3 mmol, 1.0 eq) and potassium carbonate (1.21 g, 8.76 mmol, 1.2 eq). The resulting mixture was stirred overnight at room temperature and then concentrated. The residue was dissolved in dichloromethane and washed with water and brine. The organic layer was dried over sodium sulfate, filtered and concentrated to give a crude oil which was purified via a chromatography using dichloromethane/hexanes (1:1) as the eluent to give [3-chloro-5-(2,4-difluorophenoxyl)pyrazin-2-yl]-(2-chlorophenyl)methanone (2.46 g, 6.45 mmol, 88% yield). Mass spec. M+1=382.

Step 4. Preparation of 3-(2-chlorophenyl)-6-(2,4-difluorophenoxy)-1H-pyrazolo[3,4-b]pyrazine

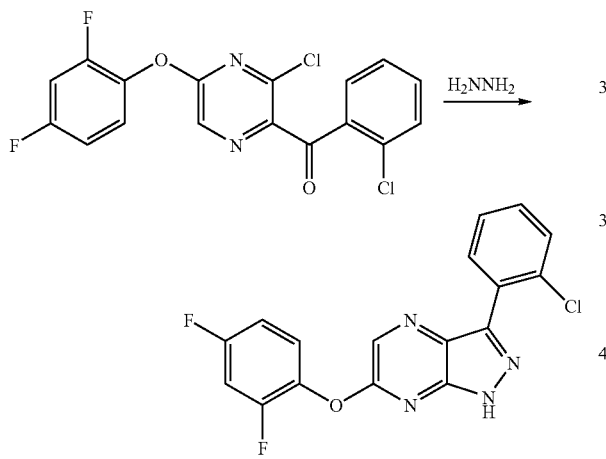

To a solution of [3-chloro-5-(2,4-difluorophenoxyl) pyrazin-2-yl]-(2-chlorophenyl)methanone (0.73 g, 1.9 mmol, 1.0 eq) in ethanol was added hydrazine hydrate (0.19 mL, 3.8 mmol, 2.0 eq). The resulting mixture was refluxed under nitrogen for 0.5 hours. The reaction mixture was cooled and filtered to give 3-(2-chlorophenyl)-6-(2,4-difluorophenoxy)-1H-pyrazolo[3,4-b]pyrazine (0.285 g, 0.8 mmol, 42% yield) as a solid. MP=240.5-241.5° C. Mass spec. M+1=359.

Step 5. Preparation of 5-Chloro-3-(2-chloro-phenyl)-6-(2,4-difluoro-phenoxy)-1H-pyrazolo[3,4-b]pyrazine

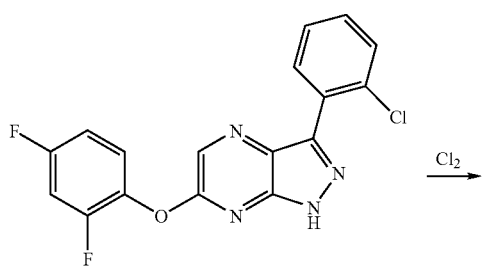

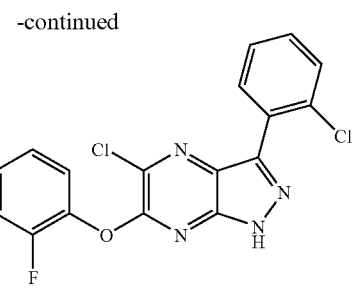

A suspension of 3-(2-chlorophenyl)-6-(2,4-difluorophenoxy)-1H-pyrazolo[3,4-b]pyrazine (2.70 g, 7.5 mmol) in 500 mL carbon tetrachloride was bubbled with chlorine gas for 16 hours at room temperature while stirring. The reaction mixture was concentrated under reduced pressure, and the residue was purified by chromatography (methylene chloride/hexanes 2:3 to 1:0) to give 1.21 g of 5-Chloro-3-(2-chloro-phenyl)-6-(2,4-difluoro-phenoxy)-1H-pyrazolo[3,4-b]pyrazine. Mass spec. M+1=394.

Step 6. Preparation of (R)-1-[3-(2-Chloro-phenyl)-6-(2,4-difluoro-phenoxy)-1H-pyrazolo[3,4-b]pyrazin-5-ylamino]-propan-2-ol

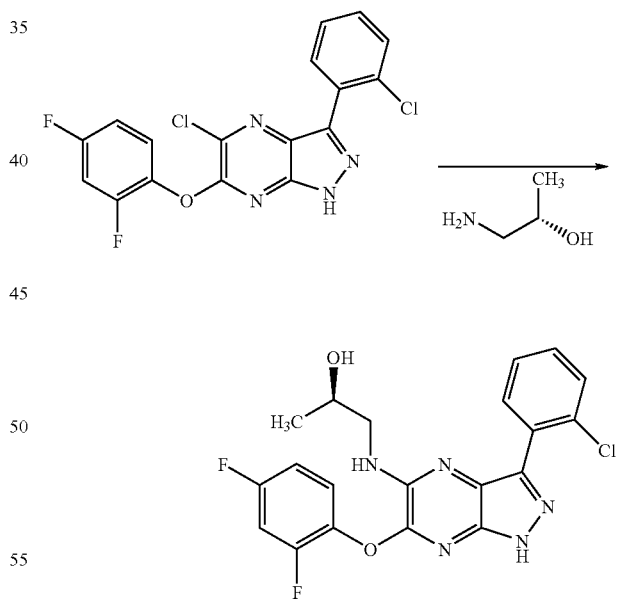

To a stirring ethanol (100 mL) suspension of 5-Chloro-3-(2-chloro-phenyl)-6-(2,4-difluoro-phenoxy)-1H-pyrazolo[3,4-b]pyrazine (0.66 g, 1.7 mmol) under nitrogen at room temperature was added (S)-1-amino-2-propanol (0.63 g, 8.4 mmol). The reaction mixture was heated to reflux and stirred for 16 hours at reflux. The reaction mixture was cooled and concentrated under reduced pressure. The residue was chromatographed (2% MeOH in hexanes) to yield 82 mg of (R)-1-[3-(2-Chloro-phenyl)-6-(2,4-difluoro-phenoxy)-1H-pyrazolo[3,4-b]pyrazin-5-ylamino]-propan-2-ol. Mass spec., M+1=433.

Example 9

This example illustrates the synthesis of (S)-1-[3-(2-Chloro-phenyl)-6-(2,4-difluoro-phenoxy)-1H-pyrazolo[4,3-c]pyridin-4-ylamino]-propan-2-ol.

Step 1. Preparation of (2-Chloro-phenyl)-(2,4,6-trifluoro-pyridin-3-yl)-methanol

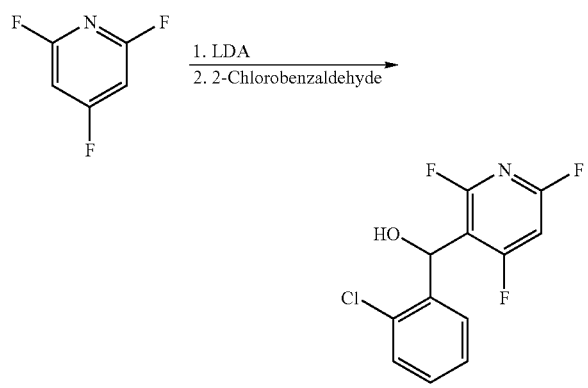

2,4,6-Trifluoropyridine (7.5 g, 56.36 mmol) was taken up in 9 mL of dry THF, and the reaction mixture was cooled to −78° C. under argon with stirring. Lithium diisopropylamine (42.3 mL of 2M solution in THF) was added dropwise, and the solution was stirred for 10 minutes. 2-Chlorobenzaldehyde (9.5 mL, 1.5 equiv) was added dropwise via syringe, and the reaction mixture was stirred for 15 minutes. The reaction was quenched by addition of saturated ammonium chloride and water, and the aqueous mixture was extracted once with EtOAc. The combined organic layers were washed with saturated brine and water, dried over MgSO$_4$, filtered and evaporated. The residue was purified by FLASH column chromatography using 5%-10% EtOAc/Hexanes to yield 8.02 g of (2-Chloro-phenyl)-(2,4,6-trifluoro-pyridin-3-yl)-methanol. Mass spec., M+1=275.

Step 2. Preparation of (2-Chloro-phenyl)-(2,4,6-trifluoro-pyridin-3-yl)-methanone

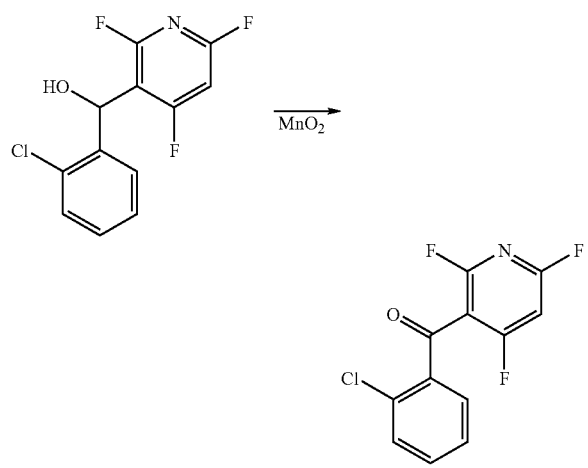

(2-Chloro-phenyl)-(2,4,6-trifluoro-pyridin-3-yl)-methanol (8.02 g, 29.3 mmol) was taken up in 80 mL of dry toluene, and manganese dioxide 26 g) was added. The reaction mixture was refluxed for 2.5 hours, after which 2.5 g of additional MnO$_2$ was added. The reaction mixture was refluxed for another hour and an additional 2.5 g of MgO$_2$ was added. The reaction mixture was refluxed for three hours, and was then hot filtered through Celite. The Celite plug was washed with hot EtOAc (in several portions), and the organic solvents were combined. The solvent was evaporated under reduced pressure, and the residue was subject to flash chromatography 5% to 10% EtOAc in hexanes) to give 2.55 g of (2-Chloro-phenyl)-(2,4,6-trifluoro-pyridin-3-yl)-methanone. Mass Spec. M−H=270.

Step 3. Preparation of (S)-(2-Chloro-phenyl)-[4,6-difluoro-2-(2-hydroxy-propylamino)-pyridin-3-yl]-methanone and (S)-(2-Chloro-phenyl)-[2,6-difluoro-4-(2-hydroxy-propylamino)-pyridin-3-yl]-methanone

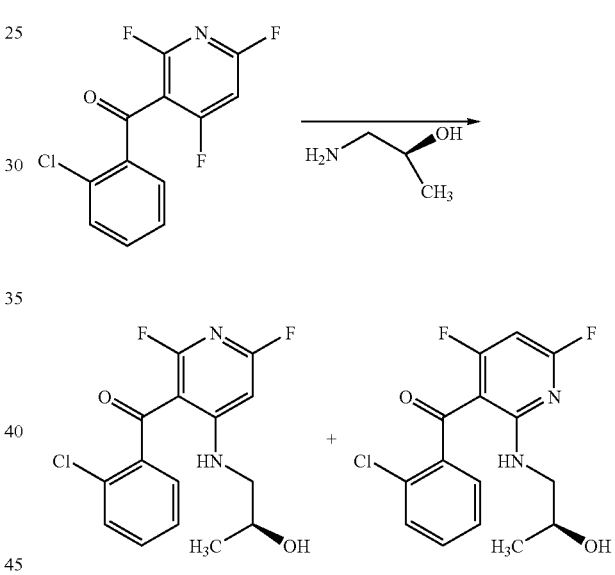

(S)-(2-Chloro-phenyl)-(2,4,6-trifluoro-pyridin-3-yl)-methanone (2.0 g, 7.36 mmol) was taken up in 30 mL dry THF and cooled to −78° C. under argon with stirring. N,N-diisopropylethylamine (1.4 mL) and (S)-1-amino-2-propanol (0.64 mL) were added, and the reaction mixture was allowed to slowly warm to −10° C. with stirring. The reaction mixture was stirred for 16 hours at −10° C., and was then quenched by addition of saturated ammonium chloride and water. The aqueous mixture was extracted with EtOAc, and the combined organic layers were washed with saturated brine and water, dried over MgSO$_4$, filtered and evaporated. The residue was purified by FLASH column chromatography using 5%-30% EtOAc/Hexanes to yield 652 mg of (S)-(2-Chloro-phenyl)-[4,6-difluoro-2-(2-hydroxy-propylamino)-pyridin-3-yl]-methanone in a first fraction, and 1.338 g of (2-Chloro-phenyl)-[2,6-difluoro-4-(2-hydroxy-propylamino)-pyridin-3-yl]-methanone in a second fraction. Mass Spec. M+H=327 for each isomer. H$^1$ NMR was used to confirm purity of the individual isomers.

Step 4. Preparation of (S)-(2-Chloro-phenyl)-[6-(2,4-difluoro-phenoxy)-4-fluoro-2-(2-hydroxy-propylamino)-pyridin-3-yl]-methanone

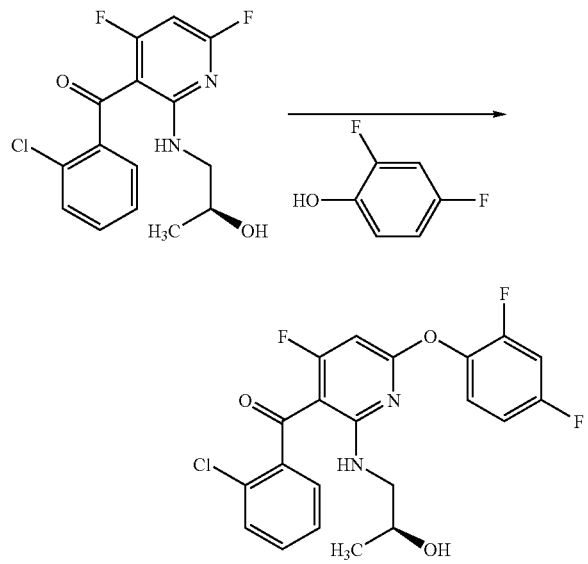

(S)-2,4-difluorophenol (0.77 mL) was placed in a flask and cooled to 0° C. with stirring, and potassium tert-butoxide (8.1 mL of 1 M THF solution) was added. The reaction mixture was stirred for 5 minutes at 0° C., and then was allowed to warm to room temperature. A solution of (2-Chloro-phenyl)-[4,6-difluoro-2-(2-hydroxy-propylamino)-pyridin-3-yl]-methanone (650 mg, 1.79 mmol) in 5 mL dry THF was added dropwise to the stirring solution, and stirring was continued for five minutes after addition. The reaction was then quenched by addition of saturated ammonium chloride and water, and the aqueous mixture was extracted with EtOAc. The combined organic layers were washed with saturated brine and water, dried over MgSO₄, filtered and evaporated. The residue was purified by preparative scale TLC (30% EtOAc in hexanes) to yield 795 mg of (S)-(2-Chloro-phenyl)-[6-(2,4-difluoro-phenoxy)-4-fluoro-2-(2-hydroxy-propylamino)-pyridin-3-yl]-methanone. Mass Spec. M+H=437.

Step 5. Preparation of (S)-1-[3-(2-Chloro-phenyl)-6-(2,4-difluoro-phenoxy)-1H-pyrazolo[4,3-c]pyridin-4-ylamino]-propan-2-ol

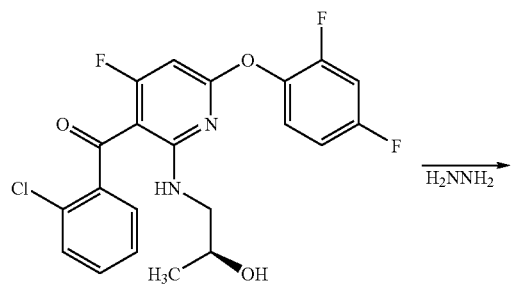

-continued

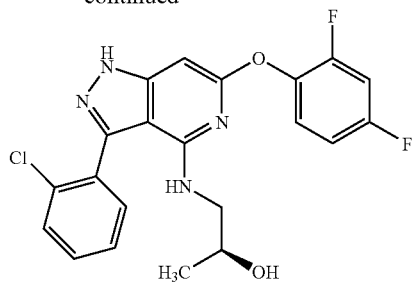

1-[3-(2-Chloro-phenyl)-6-(2,4-difluoro-phenoxy)-1H-pyrazolo[4,3-c]pyridin-4-ylamino]-propan-2-ol (690 mg, 1.6 mmol) was taken up in a mixture of 15 mL dioxane and 2 mL EtOH. N,N-diisopropylethylamine (0.3 mL) and anhydrous hydrazine (0.15 mL) were added, and the reaction mixture was slowly heated to 90° C. with stirring. The reaction mixture was stirred for six hours at 90° C., then was cooled to room temperature and quenched by addition of water and partitioned with ethyl acetate, followed by back extraction of the aqueous phase with additional ethyl acetate. The combined organic phases were washed with saturated brine and water, dried over MgSO₄, filtered and concentrated under reduced pressure. The residue was purified by preparative scale TLC (3.5% MeOH in methylene chloride), then recrystallized from methylene chloride/hexanes to give 246 mg of (S)-1-[3-(2-Chloro-phenyl)-6-(2,4-difluoro-phenoxy)-1H-pyrazolo[4,3-c]pyridin-4-ylamino]-propan-2-ol. Mass spec., M+1=432. Mp=171.2-172° C.

Example 10

This example illustrates the synthesis of (S)-1-[3-(2-Chloro-phenyl)-6-(2,4-difluoro-phenoxy)-1H-pyrazolo[3,4-b]pyridin-4-ylamino]-propan-2-ol.

Step 1. Preparation of (S)-(2-Chloro-phenyl)-[6-(2,4-difluoro-phenoxy)-2-fluoro-4-(2-hydroxy-propylamino)-pyridin-3-yl]-methanone

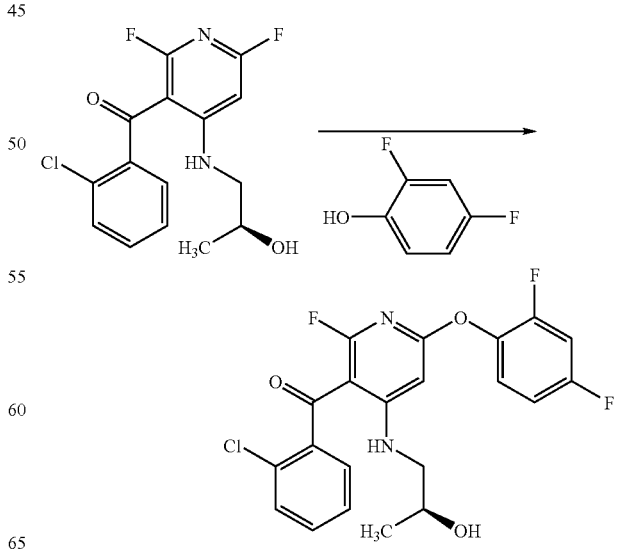

(S)-2,4-difluorophenol (0.45 mL) was placed in a flask and cooled to 0° C. via ice bath with stirring, and potassium tert-butoxide (3.1 mL of 1 M THF solution) was added. The reaction mixture was stirred for 5 minutes at 0° C. A solution of (2-Chloro-phenyl)-[2,6-difluoro-4-(2-hydroxy-propylamino)-pyridin-3-yl]-methanone (610 mg, 1.87 mmol) in 8 mL THF was added dropwise. After addition the ice bath was remove, and the reaction mixture was allowed to stir for two hours, during which time the reaction mixture warmed to room temperature. The reaction was then quenched by addition of saturated ammonium chloride and water, and the aqueous mixture was extracted with EtOAc. The combined organic layers were washed with saturated brine and water, dried over MgSO$_4$, filtered and evaporated. The residue was purified by preparative scale TLC (30% EtOAc in hexanes) to yield 864 mg of a mixture of (S)-(2-Chloro-phenyl)-[6-(2,4-difluoro-phenoxy)-2-fluoro-4-(2-hydroxy-propylamino)-pyridin-3-yl]-methanone together with the isomer (2-Chloro-phenyl)-[2-(2,4-difluoro-phenoxy)-6-fluoro-4-(2-hydroxy-propylamino)-pyridin-3-yl]-methanone as a minor product. This crude product mixture was used directly in the next step without separation.

Step 1. Preparation of (S)-1-[3-(2-Chloro-phenyl)-6-(2,4-difluoro-phenoxy)-1H-pyrazolo[3,4-b]pyridin-4-ylamino]-propan-2-ol

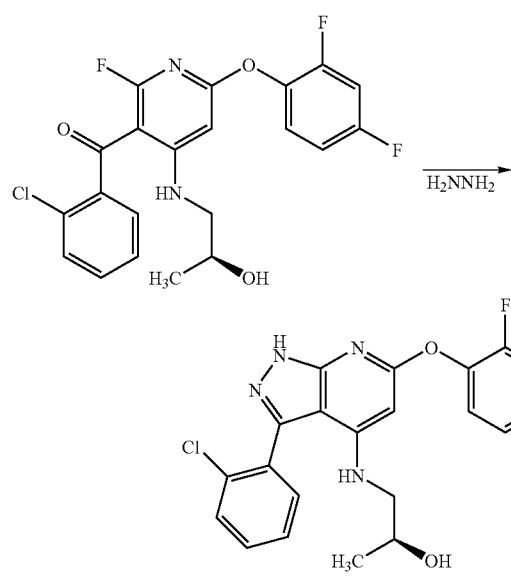

Crude (S)-(2-Chloro-phenyl)-[6-(2,4-difluoro-phenoxy)-2-fluoro-4-(2-hydroxy-propylamino)-pyridin-3-yl]-methanone (837 mg, 1.92 mmol) was treated with hydrazine using the procedure of step 5 of Example 9 to afford 148 mg of (S)-1-[3-(2-Chloro-phenyl)-6-(2,4-difluoro-phenoxy)-1H-pyrazolo[3,4-b]pyridin-4-ylamino]-propan-2-ol. Mass spec., M+1=432. Mp=237.9-238.5° C.

Example 11

This example illustrates a p38 (MAP) kinase in vitro assay useful for evaluating the compounds of the invention.

The p38 MAP kinase inhibitory activity of compounds of this invention in vitro was determined by measuring the transfer of the γ-phosphate from γ-$^{33}$P-ATP by p-38 kinase to Myelin Basic Protein (MBP), using a minor modification of the method described in Ahn, et al., *J. Biol. Chem.* 266:4220-4227 (1991).

The phosphorylated form of the recombinant p38 MAP kinase was co-expressed with SEK-1 and MEKK in *E. Coli* (see, Khokhlatchev, et al., *J. Biol. Chem.* 272:11057-11062 (1997)) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis (beta-aminoethyl ether)-N,N,N',N'-tetraacetic acid, 1 mM sodium ortho-vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedford, Mass.) and quantitated using a scintillation counter (Packard, Meriden, Conn.).

Using the above procedure, the compounds of the invention were found to be inhibitors of p38 MAP kinase. For example, 3-[3-(2-Chloro-phenyl)-6-(2,4-difluoro-phenoxy)-1H-pyrazolo[3,4-d]pyrimidin-4-ylamino]-propane-1,2-diol exhibited a p38 IC$_{50}$ (uM) of 0.004.

Example 12

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q. s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula Ia;

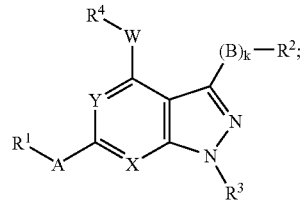

Ia or a pharmaceutically acceptable salt thereof,
wherein:
$R^1$ is 2-halophenyl or 2,4-dihalophenyl;
$R^2$ is 2-chlorophenyl, 4-hydroxyphenyl, 4methoxyphenyl, 4-benzyloxyphenyl, 3-benzyloxyphenyl, 4-dimethylaminophenyl, 4-aminophenyl, 4-fluorophenyl, 3-fluorophenyl, 2-fluorophenyl, 3-trifluoromethylphenyl, pyrid-3-yl, 4-(pyrid-2-yl)phenyl, 3-isopropoxyphenyl, 3,5-dimethylphenyl, 1,3-benzodioxol-5-yl, 3-morpholinophenyl, 4-morpholinophenyl, 3-(4-methyl-piperazin-1-yl)-phenyl, 4-(4-methyl-piperazin-1-yl)-phenyl, N-methyl-N-(2-methoxyethyl)-phenyl, 2,4-difluorophenyl, 4-isopropyloxyphenyl, 3-(2-pyridin-2-yl-ethoxy)-phenyl, or thien-2-yl;
$R^3$ is hydrogen or alkyl;
$R^4$ is hydrogen, alkyl, heteroalkyl, heterocyclyl, hydroxycycloalkyl, aryl, heteroaryl, aralkyl, heteroaralkyl, $-C(=O)-R^b$, or $-SO_2-R^b$;
wherein
$R^b$ is alkyl, heteroalkyl, aryl, aralkyl, heteroaryl, or heterocyclyl;
X and Y are nitrogen;
W is O, $S(O)_m$, $CH_2$ or $NR^f$,
wherein
m is from 0 to 2, and
$R^f$ is hydrogen, alkyl, heteroalkyl, heterocyclyl, hydroxycycloalkyl, $-C(=O)-R^g$ or $-SO_2-R^g$,
wherein
$R^g$ is alkyl, aryl, aralkyl, heteroaryl, heteroalkyl or heterocyclyl;

A is O or S;
k is 0 or 1
B is O, S(O)$_j$, CH(OR$^i$), NR$^j$, or C(=O),
wherein
j is 0, 1 or 2;
R$^i$ is hydrogen or alkyl,
R$^j$ is hydrogen, alkyl, —C(=O)—R$^k$, or —SO$_2$R$^m$,
wherein
R$^k$ is alkyl, aryl or aralkyl; and
R$^m$ is alkyl.

2. The compound of claim 1, wherein k is 0.
3. The compound of claim 2, wherein R$^3$ is hydrogen.
4. The compound of claim 3, wherein W is NR$^f$ or O.
5. The compound of claim 1, wherein R$^4$ is alkyl, heteroalkyl, heterocyclyl, hydroxycycloalkyl, —C(=O)—R$^b$ or —SO$_2$—R$^b$.
6. The compound of claim 1, wherein R$^4$ is heteroalkyl, heterocyclyl, heteroaralkyl, hydroxycycloalkyl, or —C(=O)—R$^b$.
7. The compound of claim 5, wherein R$^4$ is heteroalkyl.
8. The compound of claim 7, wherein R$^4$ is hydroxyalkyl.
9. The compound of claim 6, wherein R$^4$ is heterocyclyl.
10. The compound of claim 6, wherein R$^4$ is heteroaralkyl.
11. The compound of claim 6, wherein R$^4$ is —C(=O)—R$^b$.
12. The compound of claim 6, wherein R$^4$ is hydroxycycloalkyl.
13. A composition comprising;
(a) a pharmaceutically acceptable excipient; and
(b) a compound of claim 1.
14. A method for treating rheumatoid arthritis or osteoarthritis said method comprising administering to a patient a therapeutically effective amount of a compound of claim 1.
15. A compound selected from the group consisting of;
[3-(2-Chloro-phenyl)-6-(2,4-difluoro-phenoxy)-1H-pyrazolo[3,4-d]pyrimidin-4-yl]-dimethyl-amine;
3-(2-Chloro-phenyl)-N*6*-(2,4-difluoro-phenyl)-N*4*,N*4*dimethyl-1H-pyrazolo[-3,4-d]pyrimide-4,6-diamine;
1-[3-(2-Chloro-phenyl)-6-(2,4-difluoro-phenoxy)-1H-pyrazolo[3,4-d]pyrimidin-4-ylamino]-propan-2-ol;
3-[3-(2-Chloro-phenyl)-6-(2,4-difluoro-phenoxy)-1H-pyrazolo[3,4-d]pyrimidin-4-ylamino]-propane-1,2-diol;
2-[3-(2-Chloro-phenyl)-6-(2,4-difluoro-phenoxy)-1H-pyrazolo[3,4-d]pyrimidin-4-ylamino]-propan-1-ol;
1-[3-(2-Chloro-phenyl)-6-(2,4-difluoro-phenylsulfanyl)-1H-pyrazolo[3,4-d]-pyrimidin-4-ylamino]-propan-2-ol;
1-[3-(2-Chloro-phenyl)-6-(2-fluoro-phenoxy)-1H-pyrazolo[3,4-d]pyrimidin-4-ylamino]-propan-2-ol;
3-[3-(2-Chloro-phenyl)-6-(2-fluoro-phenoxy)-1H-pyrazolo[3,4-d]pyrimidin-4-ylamino]-propane-1,2-diol;
3-[3-(2-Chloro-phenyl)-6-(2-fluoro-phenoxy)-1H-pyrazolo[3,4-d]pyrimidin-4-ylamino]-propane-1,2-diol;
2-[3-(2-Chloro-phenyl)-6-(2-fluoro-phenoxy)-1H-pyrazolo[3,4-d]pyrimidin-4-ylamino]-propan-1-ol;
2-[3-(2-Chloro-phenyl)-6-(2,4-difluoro-phenylsulfanyl)1H-pyrazolo[3,4-d]-pyrimidin-4-ylamino]-propan-1-ol;
3-(2-Chloro-phenyl)-4-(1,1-dioxo-1lambda*6*thiomorpholin-4-yl)-6-(2-fluoro-phenoxy)-1H-pyrazolo[3,4-d]pyrimidine;
[3-(2-Chloro-phenyl)-6-(2-fluoro-phenoxy)-1H-pyrazolo[3,4-d]pyrimidin-4-yl]-(3-methanosulfonyl-propyl)-amine;
[3-(2-Chloro-phenyl)-6-(2-fluoro-phenoxy)-1H-pyrazolo[3,4-d]pyrimidin-4-yl]-(2-methanesulfonyl-ethyl)-amine;
[3-(2-Chloro-phenyl)-6-(2-fluoro-phenoxy)-1H-pyrazolo[3,4-d]pyrimidin-4-yl]-(tetrahydro-pyran-4-yl)-amine;
1-[6-(2,4-Difluoro-phenoxy)-3-(2,4-difluoro-phenyl)-1H-pyrazolo[3,4-d]pyrimidin-4-ylamino]-propan-2-ol;
Pyridine-2-carboxylic acid [3-(2-chloro-phenyl)-6-(2,4-difluoro-phenoxy)-1H-pyrazolo-[3,4-d]pyrimidin-4-yl]-amide;
1-[3-(2-Chloro-phenyl)-6-(2,4-difluoro-phenoxy)-1H-pyrazolo[3,4-d]pyrimidin-4-ylamino]-propan-2-ol;
3-[3-(2-Chloro-phenyl)-6-(2,4-difluoro-phenoxy)-1H-pyrazolo[3,4-d]pyrimidin-4-ylamino]-propane-1,2-diol;
1-[3-(2-Chloro-phenyl)-6-(2-fluoro-phenoxy)-1H-pyrazolo[3,4-d]pyrimidin-4-ylamino]-propan-2-ol;
1-[3-(2-Chloro-phenyl)-6-(2,4-difluoro-phenoxy)-1H-pyrazolo[3,4-d]pyrimidin-4-ylamino]-propan-2-ol;
2-{[3-(2-Chloro-phenyl)-6-(2,4-difluoro-phenoxy)-1H-pyrazolo[3,4-d]pyrimidin-4-yl]-methyl-amino}-ethanol;
1-[6-(2,4-Difluoro-phenoxy)-3-(2-fluoro-phenyl)-1H-pyrazolo[3,4-d]pyrimidin-4-ylamino]-propan-2-ol;
1-[6-(2,4-Difluoro-phenoxy)-3-furan-3-yl-1H-pyrazolo[3,4-d]pyrimidin-4-ylamino]-propan-2-ol;
[3-(2-Chloro-phenyl)-6-(2,4-difluoro-phenoxy)-1H-pyrazolo[3,4-d]pyrimidin-4-yl]-(1-methanesulfonyl-piperidin-4-yl)-amine;
[3-(2-Chloro-phenyl)-6-(2,4-difluoro-phenoxy)-1H-pyrazolo[3,4-d]pyrimidin-4-yl]-(2,2-dimethyl-[1,3]dioxolan-4-ylmethyl)-amine;
2-{2-[3-(2-Chloro-phenyl)-6-(2,4-difluoro-phenoxy)-1H-pyrazolo[3,4-d]pyrimidin-4-ylamino]-ethoxy}-ethanol;
6-[3-(2-Chloro-phenyl)-6-(2,4-difluoro-phenoxy)-1H-pyrazolo[3,4-d]pyrimidin-4-ylamino]-hexane-1,2,3,4,5-pentanol;
2-{[3-(2-Chloro-phenyl)-6-(2,4-difluoro-phenoxy)-1H-pyrazolo[3,4-d]pyrimidin-4-yl]-ethyl-amino}-ethanol;
1-[6-(2,4Difluoro-phenoxy)-3-(2-methoxy-phenyl)-1H-pyrazolo[3,4-d]-pyrimidin-4-ylamino]-propan-2-ol;
1-[6-(2,4-Difluoro-phenoxy)-3-(3-methoxy-phenyl)-1H-pyrazolo[3,4-d]-pyrimidin-4-ylamino]-propan-2-ol;
1-[6-(2,4-Difluoro-phenoxy)-3-(4-methoxy-phenyl)-1H-pyrazolo[3,4-d]pyrimidin-4-ylamino]-propan-2-ol;
1-[6-(2,4-Difluoro-phenoxy)-3-o-tolyl-1H-pyrazolo[3,4-d]pyrimidin-4-ylamino]-propan-2-ol;
1-[6-(2,4-Difluoro-phenoxy)-3-o-tolyl-1H-pyrazolo[3,4-d]pyrimidin-4-ylamino]-propan-2-ol;
3-(2-Chloro-phenyl)-6-(2,4-difluoro-phenoxy)-4-(1,1-dioxo-1lambda*6*-[1,2]thiazinan-2-yl)-1H-pyrazolo[3,4-d]pyrimidine;
1-[3-(2-Chloro-4-methoxy-phenyl)-6-(2,4-difluoro-phenoxy)-1H-pyrazolo[3,4-d]pyrimidin-4-ylamino]-propan-2-ol;
1-[6-(2,4-Difluoro-phenoxy)-3-(4-methoxy-2-methyl-phenyl)-1H-pyrazolo[3,4-d]-pyrimidin-4-ylamino]-propan-2-ol;
1-[6-(2,4-Difluoro-phenoxy)-3-(2,5-dimethoxy-phenyl)-1H-pyrazolo[3,4-d]-pyrimidin-4-ylamino]-propan-2-ol;
3-(2-Chloro-phenyl)-6-(2,4-difluoro-phenoxy)-4-(4-methyl-piperazin-1-yl)-1H-pyrazolo[3,4-d]pyrimidine;
[3-(2-Chloro-phenyl)-6-(2,4-difluoro-phenoxy)-1H-pyrazolo[3,4-d]pyrimidin-4-yl]-(3-morpholin-4-yl-propyl)-amine;

[3-(2-Chloro-phenyl)-6-(2,4-difluoro-phenoxy)-1H-pyrazolo[3,4-d]pyrimidin-4-yl]-(2-morpholin-4-yl-ethyl)-amine;

N'-[3-(2-Chloro-phenyl)-6-(2,4-difluoro-phenoxy)-1H-pyrazolo[3,4-d]pyrimidin-4-yl]-N,N-dimethyl-propane-1,3-diamine;

[3-(2-Chloro-phenyl)-6-(2,4-difluoro-phenoxy)-1H-pyrazolo[3,4-d]pyrimidin-4-yl]-[3-(4-methyl-piperazin-1-yl)-propyl]-amine;

3-[3-(2-Chloro-phenyl)-6-(2,4-difluoro-phenoxy)-1H-pyrazolo[3,4-d]pyrimidin-4-ylamino]-pentane-1,5-diol;

[3-(2-Chloro-phenyl)-6-(2,4-difluoro-phenoxy)-1H-pyrazolo[3,4-d]pyrimidin-4-yl]-[2-(tetrahydro-pyran-4-yl)-ethyl]-amine;

[3-(2-Chloro-phenyl)-6-(2,4-difluoro-phenoxy)-1H-pyrazolo[3,4-d]pyrimidin-4-yl]-(tetrahydro-furan-2-ylmethyl)amine;

3-(2-Chloro-phenyl)-6-(2,4-difluoro-phenoxy)-4-morpholin-4-yl-1H-pyrazolo[3,4-d]pyrimidine;

3-(2-Chloro-phenyl)-6-(2,4-difluoro-phenoxy)-4-(4methanesulfonyl-piperazin-1-yl)-1H-pyrazolo[3,4-d]pyrimidine;

[3-(2-Chloro-phenyl)-6-(2,4-difluoro-phenoxy)-1H-pyrazolo[3,4-d]pyrimidin-4-ylamino]-acetic acid tert-butyl ester;

1-[3-(2-Chloro-phenyl)-6-(2,4-difluoro-phenoxy)-1H-pyrazolo[3,4-d]pyrimidin-4-yl]-piperidin-4-ol;

{1-[3-(2-Chloro-phenyl)-6-(2,4-difluoro-phenoxy)-1H-pyrazolo[3,4-d]pyrimidin-4-yl]-piperidin-4-yl}-methanol;

2-{1-[3-(2-Chloro-phenyl)-6-(2,4-difluoro-phenoxy)-1H-pyrazolo[3,4-d]pyrimidin-4-yl]-piperidin-4-yl}-ethanol;

1-[3-(2-Chloro-phenyl)-6-(2,4-difluoro-phenoxy)-1H-pyrazolo[3,4-d]pyrimidin-4-ylamino]-butane-2,3-diol;

[3-(2-Chloro-phenyl)-6-(2,4-difluoro-phenoxy)-1H-pyrazolo[3,4-d]pyrimidin-4-ylamino]-acetic acid;

2-[3-(2-Chloro-phenyl)-6-(2,4-difluoro-phenoxy)-1H-pyrazolo[3,4-d]pyrimidin-4-ylamino]-butane-1,3-diol;

[3-(2-Chloro-phenyl)-6-(2,4-difluoro-phenoxy)-1H-pyrazolo[3,4-d]pyrimidin-4-yl]-pyridin-2-ylmethyl-amine;

3-(2-Chloro-phenyl)-6-(2,4-difluoro-phenoxy)-4-(tetrahydro-pyran-4-yloxy)-1H-pyrazolo[3,4-d]pyrimidine;

1-[3-(2-Chloro-phenyl)-6-(2,4-difluoro-phenoxy)-1H-pyrazolo[3,4-d]pyrimidin-4-yl]-azetidin-3-ol;

{1-[3-(2-Choro-phenyl)-6-(2,4-difluoro-phenoxy)-1H-pyrazolo[3,4-d]pyrimidin-4-yl]-pyrrolidin-2-yl}-methanol;

1-[3-(2-Chloro-phenyl)-6-(2,4-difluoro-phenoxy)-1H-pyrazolo[3,4-d]pyrimidin-4-yl]-piperidin-3-ol;

2-[3-(2-Chloro-phenyl)-6-(2,4-difluoro-phenoxy)-1H-pyrazolo[3,4-d]pyrimidin-4-ylamino]-propane-1,3-diol;

3-{3-Chloro-4-[6-(2,4-difluoro-phenoxy)-4-(2-hydroxy-propylamino)-1H-pyrazolo[3,4-d]pyrimidin-3-yl]-phenoxy}-propane-1,2-diol;

2-[3-(2-Chloro-phenyl)-6-(2,4-difluoro-phenoxy)-1H-pyrazolo[3,4-d]pyrimidin-4-ylamino]-cyclohexanol;

2-[3(2-Chloro-phenyl)-6-(2,4-difluoro-phenoxy)-1H-pyrazolo[3,4-d]pyrimidin-4-ylamino]-cyclohexanol;

2-[3-(2-Chloro-phenyl)-6-(2,4-difluoro-phenoxy)-1H-pyrazolo[3,4-d]pyrimidin-4-ylamino]-2-methyl-propan-1-ol;

2-[3-(2-Chloro-phenyl)-6-(2,4-difluoro-phenoxy)-1H-pyrazolo[3,4-d]pyrimidin-4-ylamino]-butane-1,3-diol;

2-[3-(2-Chloro-phenyl)-6-(2,4-difluoro-phenoxy)-1H-pyrazolo[3,4-d]pyrimidin-4-ylamino]-butane-1,3-diol;

3-[3-(2-Chloro-phenyl)-6-(2,4-difluoro-phenoxy)-1H-pyrazolo[3,4-d]pyrimidin-4-ylamino]-propionic acid tert-butyl ester;

3-[3-(2-Chloro-phenyl)-6-(2,4-difluoro-phenoxy)-1H-pyrazolo[3,4-d]pyrimidin-4-ylamino]-propionic-acid;

[3-(2-Chloro-phenyl)-6-(2,4-difluoro-phenoxy)-1H-pyrazolo[3,4-d]pyrimidin-4-yl]-(3-fluoro-oxetan-3-ylmethyl)-amine;

[3-(2-Chloro-phenyl)-6-(2,4-difluoro-phenoxy)-1H-pyrazolo[3,4-d]pyrimidin-4-yl]-(1-methoxymethyl-cyclopropylmethyl)-amine;

2-[3-(2-Chloro-phenyl)-6-(2,4-difluoro-phenoxy)-1H-pyrazolo[3,4-d]pyrimidin-4-ylamino]-butane-1,3-diol;

3-[3-(2-Chloro-phenyl)-6-(2,4-difluoro-phenoxy)-1H-pyrazolo[3,4-d]pyrimidin-4-ylamino]-1-morpholin-4-yl-propan-1-one;

4-[3-(2-Chloro-phenyl)-6-(2,4-difluoro-phenoxy)-1H-pyrazolo[3,4-d]pyrimidin-4-ylamino]-butyric acid tert-butyl ester;

4-[3-(2-Chloro-phenyl)-6-(2,4-difluoro-phenoxy)-1H-pyrazolo[3,4-d]pyrimidin-4-ylamino]-butyric acid;

4-[3-(2-Chloro-phenyl)-6-(2,4-difluoro-phenoxy)-1H-pyrazolo[3,4-d]pyrimidin-4-ylamino]1-morpholin-4-yl-butan-1-one;

2-[3-(2-Chloro-phenyl)-6-2,4-difluoro-phenoxy)-1H-pyrazolo[3,4-d]pyrimidin-4-ylamino]-2-hydroxymethyl -propane-1,3-diol;

2-[3-(2-Chloro-phenyl)-6-(2,4-difluoro-phenoxy)-1H-pyrazolo[3,4-d]pyrimidin-4-ylamino]-cyclopentanol;

[3-(2-Chloro-phenyl)-6-(2,4-difluoro-phenoxy)-1H-pyrazolo[3,4-d]pyrimidin-4-yl]-(hexahydro-furo[2,3-b]furan-3-yl)-amine;

1-[3-(5-Chloro-2-methoxy-phenyl)-6(2,4-difluoro-phenoxy)-1H-pyrazolo[3,4-d]-pyrimidin-4-ylamino]-propan-2-ol;

1-[6-(2,4-Difluoro-phenoxy)-3-(5-fluoro-2-methoxy-phenyl)-1H-pyrazolo[3,4]pyrimidin-4-ylamino]-propan-2-ol;

1-[6-(2,4-Difluoro-phenoxy)-3-(4-fluoro-2-methoxy-phenyl)-1H-pyrazolo[3,4-d]pyrimidin-4-ylamino]-propan-2-ol;

1-[3-(5-Chloro-2-methyl-phenyl)-6-(2,4-difluoro-phenoxy)-1H-pyrazolo[3,4-d]pyrimidin-4-ylamino]-propan-2-ol;

5-[3-(2-Chloro-phenyl)-6-(2,4-difluoro-phenoxy)-1H-pyrazolo[3,4-d]pyrimidin-4-yloxy]-cyclohexane-1,3-diol;

[3-(2-Chloro-phenyl)-6-(2,4-difluoro-phenoxy)-1H-pyrazolo[3,4-d]pyrimidin-4-yl]-[2-(2-methyl-2H-tetrazol-5-yl)-ethyl]-amine;

N-{2-[3-(2-Chloro-phenyl)-6-(2,4-difluoro-phenoxy)-1H-pyrazolo[3,4-d]pyrimidin-4-ylamino]-ethyl}-methanesulfonamide;

2-[3-(2-Chloro-phenyl)-6-(2,4-difluoro-phenoxy)-1H-pyrazolo[3,4-d]pyrimidin-4-ylamino]-2-ethyl-propane-1,3-diol;

2-[3-(2-Chloro-phenyl)-6-(2,4-difluoro-phenoxy)-1H-pyrazolo[3,4-d]pyrimidin-4-ylamino]-2-methyl-propane-1,3-diol;

1-[3-(2-Chloro-phenyl)-6-(2,4-difluoro-phenoxy)-1H-pyrazolo[3,4-d]pyrimidin-4-ylamino]-3-methoxy-propan-2-ol;

1-[6-(2,4-Difluoro-phenoxy)-3-(2,4-dimethoxy-phenyl)-1H-pyrazolo[3,4-d]-pyrimidin-4-ylamino]-propan-2-ol;

1-[6-(2,4-Difluoro-phenoxy)-3-(2-methoxymethyl-phenyl)-1H-pyrazolo[3,4-d]pyrimidin-4-ylamino]-propan-2-ol;

1[6-(2,4-Difluoro-phenoxy)-3-(2-methoxy-pyridin-3-yl)-1H-pyrazolo[3,4-d]pyrimidin-4-ylamino]-propan-2-ol;

3-(2-Chloro-phenyl)-6-(2,4-difluoro-phenoxy)-4-(4-pyrimidin-2-yl-piperazin-1yl)-1H-pyrazolo[3,4-d]pyrimidine;

1-[6-(2,4-Difluoro-phenoxy )-3-(2,4-dimethoxy-pyrimidin-5-yl)-1H-pyrazolo[3,4-d]pyrimidin-4-ylamino]-propan-2-ol;

1-[3-(2-Chloro-phenyl)-6-(2,4-difluoro-phenoxy)-1H-pyrazolo[3,4-d]pyrimidin-4-yl[-pyrrolidin-3-ol;

[3-(2-Chloro-phenyl)-6-(2,4-difluoro-phenoxy)-1H-pyrazolo[3,4-d]pyrimidin-4-yl]-[2-(2H-tetrazol-5-yl)-ethyl]-amine;

4-3-(2-Chloro-phenyl)-6-(2,4-difluoro-phenoxy)-1H-pyrazolo[3,4-d]pyrimidin-4-ylamino]-tetrahydro-pyran-3-ol;

3-(2-Chloro-phenyl)-6-(2,4-difluoro-phenoxy)-1H-pyrazolo[3,4-d]pyrimidin-4-ylamine -2-[3-(2-Chloro-phenyl)-6-(2,4-difluoro-phenoxy)-1H-pyrazolo[3,4-d]pyrimidin-4-ylamino]-N,N-dimethyl-acetamide;

1-[3-(4-Chloro-2-methyl-phenyl)-6-(2,4-difluoro-phenoxy)-1H-pyrazolo[3,4-d]pyrimidin-4-ylamino]-propan-2-ol;

1-[3-(2-Chloro-phenyl)-6-(2,4-difluoro-phenoxy)-1H-pyrazolo[3,4-d]pyrimidin-4-ylamino]-2-methyl-propan-2-ol;

1-[6-(2,4-Difluoro-phenoxy)-3-pyrimidin-5-yl-1H-pyrazolo[3,4-d]pyrimidin-4-ylamino]-propan-2-ol;

[3-(2-Chloro-phenyl)-6-(2,4-difluoro-phenoxy)-1H-pyrazolo[3,4-d]pyrimidin-4-yl]-(2-[1,2,4]triazol-1-yl-ethyl)-amine;

2-[3-(2-Chloro-phenyl)-6-(2,4-difluoro-plenoxy)-1H-pyrazolo[3,4-d]pyrimidin-4-ylamino]-1-morpholin-4-yl -ethanone;

1-[3-(2-Chloro-phenyl)-6-(4-fluoro-phenoxy)-1H-pyrazolo[3,4-d]pyrimidin-4-ylamino]-propan-2-ol;

4-[3-(2-Chloro-phenyl)-6-(2,4-difluoro-phenoxy)-1H-pyrazolo[3,4-d]pyrimidin-4-ylamino]-tetrahydro-furan-3-ol;

1-[3-(2-Chloro-phenyl)-6-(4-fluoro-phenoxy)-1H-pyrazolo[3,4-d]pyrimidin-4-ylamino]-aminosulfonyl ethylamine;

1-[6-(2,4-Difluoro-phenoxy)-3-(4-methyl-thiophen-3-yl)-1H-pyrazolo[3,4-d]pyrimidin-4-ylamino]-propan-2-ol;

1-[3-(2,5-Dichloro-phenyl)-6-(2,4-difluoro-phenoxy)-1H-pyrazolo[3,4-d]-pyrimidin-4-ylamino]-propan-2-ol;

1-[6-(2,4-Difluoro-phenoxy)-3-(2-ethoxy-phenyl)-1H-pyrazolo[3,4-d]pyrimidin-4-ylamino]-propan-2-ol;

1-[6-(2,4-Difluoro-phenoxy)-3-(2,3-dimethoxy-phenyl)-1H-pyrazolo[3,4-d]pyrimidin-4-ylamino]-propan-2-ol;

1-[6-(2-Chloro-4-fluoro-phenoxy)-3-(2-chloro-phenyl)-1H-pyrazolo[3,4-d]pyrimidin-4-ylamino]-propan-2-ol;

N-[3-(2-Chloro-phenyl)-6-(2,4-difluoro-phenoxy)-1H-pyrazolo[3,4-d]pyrimidin-4-yl]-N'-pyrimidin-2yl-ethane-1,2-diamine;

(3-{[3-(2-Chloro-phenyl)-6-(2,4-difluoro-phenoxy)-1H-pyrazolo[3,4-d]pyrimidin-4-ylamino]-methyl}-oxetan-3-yl)-methanol;

3-(2-Chloro-phenyl)-6-(2,4-difluoro-phenoxy)-4-(2,2-dimethyl-[1,3]dioxolan-4-ylmethoxy)-1H-pyrazolo[3,4-d]pyrimidine;

3-[3-(2-Chloro-phenyl)-6-(2,4-difluoro-phenoxy)-1H-pyrazolo[3,4-d]pyrimidin-4-yloxy]-propane-1,2-diol;

2-[3-(2-Chloro-phenyl)-6-(2,4-difluoro-phenoxy)-1H-pyrozolo[3,4-d]pyrimidin-4-ylamino]-3-hydroxy-propionic acid tert-butyl ester;

1-[3-(2-Chloro-phenyl)-6-(2,4-dichloro-phenoxy)-1H-pyrazolo[3,4-d]pyrimidin-4-ylamino]-propan-2-ol;

2-[3-(2-Chloro-phenyl)-6-(2,4-difluoro-phenoxy)-1H-pyrazolo[3,4-d]pyrimidin-4-ylamino]-3-hydroxy-butyric acid tert-butyl ester;

1-{2-[3-(2-Chloro-phenyl)-6-(2,4-difluoro-phenoxy)-1H-pyrazolo[3,4-d]pyrimidin-4-ylamino]-ethyl}-pyrrolidine-2,5-dione;

[3-(2-Chloro-phenyl)-6-(2,4-difluoro-phenoxy)-1H-pyrazolo[3,4-d]pyrimidin-4-yl]-(2-methanesulfonyl-ethyl)-amine;

6-[3-(2-Chloro-phenyl)-6-(2,4-difluoro-phenoxy)-1H-pyrazolo[3,4-d]pyrimidin-4-yloxy]-hexahydro-furo[3,2-b]furan-3-ol;

1-[3-(2-Chloro-phenyl)-6-(3-fluoro-phenoxy)-1H-pyrazolo[3,4-d]pyrimidin-4-ylamino]-propan-2-ol;

2-[3-(2-Chloro-phenyl)-6-(2,4-difluoro-phenoxy)-1H-pyrazolo[3,4-d]pyrimidin-4-ylamino]-3-hydroxy-propionic acid;

1-[3-(2-Chloro-phenyl)-6-(2,3-difluoro-phenoxy)-1H-pyrazolo[3,4-d]pyrimidin-4-ylamino]propan-2-ol;

1-[3-(2-Chloro-phenyl)-6-(3,4-difluoro-phenoxy)-1H-pyrazolo[3,4-d]pyrimidin-4-ylamino]-propan-2-ol;

2-[3-(2-Chloro-phenyl)-6-(2,4-difluoro-phenoxy)-1H-pyrazolo[3,4-d]pyrimidin-4-ylamino]-3-hydroxy-butyric acid;

2-[3-(2-Chloro-phenyl)-6-(2,4-difluoro-phe noxy)-1H-pyrazolo[3,4-d]pyrimidin-4-ylamino]-3-hydroxy-1-morpholin-4-yl-propan-1-one;

2-[3-(2-Chloro-phenyl)-6-(2,4-difluoro-phenoxy)-1H-pyrazolo[3,4-d]pyrimidin-4-ylamino]-3-hydroxy-1-morpholin-4-yl-butan-1-one;

2-Amino-3-methyl-butyric acid 2-[3-(2-chloro-phenyl)-6-(2,4-difluoro-phenoxy)-1H-pyrazolo[3,4-d]pyrimidin-4-ylamino]-1-methyl-ethyl ester;

[3-(2-Chloro-phenyl)-6-(2,4-difluoro-phenoxy)-1H-pyrazolo[3,4-d]pyrimidin-4-yl]-[2-(1H-tetrazol-5-yl)-ethyl]-amine;

3-(2-Chloro-phenyl)-6-(2,4-difluoro-phenoxy)-4-methanesulfonylmethyl-1H-pyrazolo[3,4-d]pyrimidine;

1-}2-[3-(2-Chloro-phenyl)-6-(2,4-difluoro-phenoxy)-1H-pyrazolo[3,4-d]pyrimidin-4-ylamino]-ethyl}-imidazolidin-2-one;

2-[3-(2-Chloro-phenyl)-6-(2,4-difluoro-phenoxy)-1H-pyrazolo[3,4-d]pyrimidin -4-ylamino]-3-hydroxy-N,N-dimethyl-propionamide;

2-[3-(2-Chloro-phenyl)-6-(2,4-difluoro-phenoxy)-1H-pyrazolo[3,4-d]pyrimidin-4-ylamino]-3-hydroxy-N,N-dimethyl-butyramide;

N-[3-(2-Chloro-phenyl)-6-(2,4-difluoro-phenoxy)-1H-pyrazolo[3,4-d]pyrimidin-4-yl]-N-methyl-methanesulfonamide;

1-[3-(2-Chloro-phenyl)-6-(2,4,6-trifluoro-phenoxy)-1H-pyrazolo[3,4-d]pyrimidin-4-ylamino]-propan-2-ol;

6-(2,4-Difluoro-phenoxy)-4-(1,1-dioxo-1lambda*6*-[1,2]thiazinan-2-yl)-3-phenyl-1H-pyrazolo[3,4-d]pyrimidine;

3-(2-Chloro-phenyl)-6-(2,4-difluoro-phenoxy)-4-(1,1-dioxo-1lambda*6*-isothiazolidin-2-yl)-1H-pyrazolo[3,4-d]pyrimidine;

3-[3-(2-Chloro-phenyl)-6-(2,4-difluoro-phenoxy)-1H-pyrazolo[3,4-d]pyrimidin-4-ylamino]-2-methyl-butan-2-ol;

1-[3-(2-Chloro-phenyl)-6-(2-fluoro-phenoxy)-1H-pyrazolo[3,4-d]pyrimidin-4-ylamino]-2-methyl-propan-2-ol;

4-[3-(2-Chloro-phenyl)-6-(2,4-difluoro-phenoxy)-1H-pyrazolo[3,4-d]pyrimidin-4-ylamino]-2-methyl-butan-2-ol;

3-(2-Chloro-phenyl)-6-(2,4-difluoro-phenoxy)-4-[2-(2,2-dimethyl-[1,3]dioxolan-4-yl)-ethoxy]-1H-pyrazolo[3,4-d]pyrimidine;

[3-(2-Chloro-phenyl)-6-(2,4-difluoro-phenoxy)-1H-pyrazolo[3,4-d]pyrimidin-4-yl]-methanol;

1-[6-(2,4-Difluoro-phenoxy)-3-(2-ethoxy-4-fluoro-phenyl)-1H-pyrazolo[3,4-d]pyrimidin-4-ylamino]-propan-2-ol;

1-[6-(2,4-Difluoro-phenoxy)-3-(2-ethoxy-5-fluoro-phenyl)-1H-pyrazolo[3,4-d]pyrimidin-4-ylamino]-propan-2-ol;

Tetrahydro-furan-2-carboxylic acid {3-[3-(2-chloro-phenyl)-6-(2,4-difluom-phenoxy)-1H-pyrazolo[3,4-d]pyrimidin-4-ylamino]-propyl}-amide;

4-[3-(2-Chloro-phenyl)-6-(2,4-difluoro-phenoxy)-1H-pyrazolo[3,4-d]pyrimidin-4-yloxy]-butane-1,2-diol;

1-[3-(2-Chloro-phenyl)-6-(2,4-difluoro-phenoxy)-1H-pyrazolo[3,4-d]pyrimidin-4-yloxy]-propan-2-one;

3-(2-Chloro-phenyl)-6-(2,4-difluoro-phenoxy)-4-ethoxy-1H-pyrazolo[3,4-d]pyrimidine;

[3-(2-Chloro-phenyl)-6-(2,4-difluoro-phenoxy)-1H-pyrazolo[3,4-d]pyrimidin-4yl]-[2-(2-methyl-imidazol-1-yl)-ethyl]-amine;

1-[6-(2,4-Difluoro-phenoxy)-3-(2,4-difluoro-phenyl)-1H-pyrazolo[3,4-d]pyrimidin-4-ylamino]-2-methyl-propan-2-ol;

1-[3-(2-Chloro-phenyl)-6-(2,4-difluoro-phenoxy)-1H-pyrazolo[3,4-d]pyrimidin-4-yloxy]-propan-2-ol;

1-[3-(2-Chloro-phenyl)-6-(2,4-difluoro-phe noxy)-1H-pyrazolo[3,4d]pyrimidin-4-yloxy]-2-methyl-propan-2-ol;

3-(2-Chloro-phenyl)-6-(2,4-difluoro-phenoxy)-4-[3-(2,2-dimethyl-[1,3]dioxolan-4-yl)-propoxy]-1H-pyrazolo[3,4-d]pyrimidine;

5-[3-(2-Chloro-phenyl)-6-(2,4-difluoro-phenoxyy-1H-pyrazolol 3,4-d]pyrimidin-4-yloxy]-pentane-1,2-diol;

2-[6-(2,4-Difluoro-phenoxy)-3-(2,4-difluoro-phenyl)-1H-pyrazolo[3,4-d]pyrimidin-4-ylamino]-butane-1,3-diol;

2-(6-(2,4-Difluoro-phenoxy)-3-(2,4-difluoro-phenyl)-1H-pyrazolo[3,4-d]pyrimidin-4-ylamino]-propane-1,3-diol;

1-[6-(2,4-Difluoro-phenoxy)-3-(4-fluoro-2-methoxy-phenyl)-1H-pyrazolo[3,4-d]pyrimidin-4-ylamino]-2-methyl-propan-2-ol;

1-[6-(2,4-Difluoro-phenoxy)-3-(5-fluoro-2-methoxy-phenyl)-1H-pyrazolo[3,4-d]pyrimidin-4-ylamino]-2-methyl-propan-2-ol;

1-[6-(2,4-Difluoro-phenoxy)-3-(2-ethoxy-5-fluoro-phenyl)-1H-pyrazolo[3,4-d]pyrimidin-4-ylamino]-2-methyl-propan-2-ol;

1-[3-(2-Chloro-phenyl)-6-(4-fluoro-phenoxy)-1H-pyrazolo[3,4-d]pyrimidin-4-ylamino]-2-methyl-propan-2-ol;

1-[6-(2,4-Difluoro-phenoxy)-3-(2-trifluoromethoxy-phenyl)-1H-pyrazolo[3,4-d]pyrimidin-4-ylamino]-2-methyl-propan-2-ol;

{2-[3-(2-Chloro-phenyl)-6-(2,4-difluoro-phenoxy)-1H-pyrazolo[3,4-d]pyrimidin-4-ylamino]-ethyl}-urea;

3-[3-(2-Chloro-phenyl)-6-(2,4-difluoro-phenoxy)-1H-pyrazolo[3,4-d]pyrimidin-4-ylsulfanyl]-propan-1-ol;

1-[6-(2,4-Difluoro-phenoxy)-3-(2-ethoxy-4-fluoro-phenyl)-1H-pyrazolo[3,4-d]pyrimidin-4-ylamino]-2-methyl-propan-2-ol;

1-[6-(2,4-Difluoro-phenoxy)-3-(1-methyl-1H-pyrrol-2-yl)-1H-pyrazolo[3,4-d]pyrimidin-4-ylamino]-propan-2-ol;

1-{2-[3-(2-Chloro-phenyl)-6-(2,4-difluoro-phenoxy)-1H-pyrazolo[3,4-d]pyrimidin-4-ylamino]-ethyl}-pyrrolidin-2-one;

3-[6-(2,4-Difluoro-phenoxy)-3-(2,4-difluoro-phenyl)-1H-pyrazolo[3,4-d]pyrimidin-4-yloxy]-propane-1,2-diol;

3-(2-Chloro-phenyl)-6-(2,4-difluoro-phenoxy)-4-(2-morpholin-4-yl-ethoxy)-1H-pyrazolo[3,4-d]pyrimidine;

2-[6-(2,4-Difluoro-phenoxy)-3-(2,4-difluoro-phenyl)-1H-pyrazolo[3,4d]pyrimidin-4-ylamino]-2-methyl-propane-1,3-diol;

5-{2-[3-(2-Chloro-phenyl)-6-(2,4-difluoro-phenoxy)-1H-pyrazolo[3,4-d]pyrimidin-4-ylamino]-ethyl}-4-methyl-2,4-dihydro-[1,2,4]triazol-3-one;

[3-(2-Chloro-phenyl)-6-(2,4-difluoro-phenoxy)-1H-pyrazolo[3,4-d]pyrimidin-4-yl]-(2-[1,3,4]oxadiazol -2-yl-ethyl)-amine;

3-(2-Chloro-phenyl)-6-(2,4-difluoro-phenoxy)-4-[2-(4-methyl-piperazin-1-yl)-ethoxy]-1H-pyrazolo[3,4-d]pyrimidine;

3-(2-Chloro-phenyl)-6-(2,4-difluoro-phenoxy)-4-[2-(4-methanesulfonyl piperazin-1-yl)-ethoxy]-1H-pyrazolo[3,4-d]pyrimidine;

2-[3-(2-Chloro-phenyl)-6-(2,4-difluoro-phenoxy)-1H-pyrazolo[3,4-d]pyrimidin-4-ylamino]-ethanesulfonic acid amide;

2-[3-(2-Chloro-4-fluoro-phenyl)-6-(2,4-difluoro-phenoxy)-1H-pyrazolo[3,4-d]pyrimidin-4-ylamino]-propane-1,3-diol;

1-{2-[3-(2-Chloro-phenyl)-6-(2,4-difluoro-phenoxy)-1H-pyrazolo[3,4-d]pyrimidin-4-yloxy]-ethyl}-imidazolidin-2-one;

[3-(2-Chloro-phenyl)-6-(2,4-difluoro-phenoxy)-1H-pyrazolo[3,4-d]pyrimidin-4-yl]-[2-(2-methoxymethyl-2H-[1,2,4]triazol-3-yl)-ethyl]-amine;

[3-(2-Chloro-phenyl)-6-(2,4-difluoro-phenoxy)-1H-pyrazolo[3,4-d]pyrimidin-4-yl]-[2-(1-methoxymethyl-1H-[1,2,4]triazol-3-yl)-ethyl]-amine;

3-{2-(3-(2-Chloro-phenyl)-6-(2,4-difluoro-phenoxy)-1H-pyrazolo[3,4-d]pyrimidin-4-ylamino]-ethyl}-oxazolidin-2-one;

[3-(2-Chloro-phenyl)-6-(2,4-difluoro-phenoxy)-1H-pyrazolo[3,4-d]pyrimidin-4-yl]-[2-(1-methyl-1H-imidazol-2-yl)-ethyl]-amine;

2-[3-(4-Chloro-2-fluoro-phenyl)-6-(2,4-difluoro-phenoxy)-1H-pyrazolo[3,4-d]pyrimidin-4-ylamino]-2-methyl-propane-1,3-diol;

[3-(2-Chloro-phenyl)-6-(2,4-difluoro-phenoxy)-1H-pyrazolo[3,4-d]pyrimidin-4-yl]-[2-(4H-[1,2,4]triazol-3-yl-ethyl]-amine;

2-[3-(4-Chloro-2-fluoro-phenyl)-6-(2,4-difluoro-phenoxy)-1H-pyrazolo[3,4-d]pyrimidin-4-ylamino]-propane-1,3diol;

[3-(2-Chloro-phenyl)-6-(2,4-difluoro-phenoxy)-1H-pyrazolo[3,4-d]pyrimidin-4-yl]-[1,4]dioxan-2-ylmethyl-amine;

{2-[3-(2-Chloro-phenyl)-6-(2,4-difluoro-phenoxy )-1H-pyrazolo[3,4-d]pyrimidin-4-yloxy]-ethyl}-diethyl-amine;

3-(2-Chloro-phenyl)-6-(2,4-difluoro-phenoxy)-4-(2-pyrrolidin-1-yl-ethoxy)-1H-pyrazolo[3,4-d]pyrimidine;

3-(2-Chloro-phenyl)-6-(2,4-difluoro-phenoxy)-4-(1-methyl-piperidin-4-ylmethoxy)-1H-pyrazolo[3,4-d]pyrimidine;

{2-[3-(2-Chloro-phenyl)-6-(2,4-difluoro-phenoxy)-1H-pyrazolo[3,4-d]pyrimidin-4-yloxy]-ethyl}-dimethyl-amine;

[3-(2-Chloro-phenyl)-6-(2,4-difluoro-phenoxy)-1H-pyrazolo[3,4-d]pyrimidin-4-yl]-methanesulfonamide;

C-[3-(2-Chloro-phenyl)-6-(2,4-difluoro-phenoxy)-1H-pyrazolo[3,4-d]pyrimidin-4-yl]-N-methyl-methane-sulfonamide;

Methoxy-acetic acid N'-[3-(2-chloro-phenyl)-6-(2,4-difluoro-phenoxy)-1H-pyrazolo[3,4-d]pyrimidin-4-yl]-hydrazide;

[3-(2-Chloro-phenyl)-6-(2,4-difluoro-phenoxy)-1H-pyrazolo[3,4-d]pyrimidin-4-yl]-hydrazine;

3-[3-(4-Chloro-2-fluoro-phenyl)-6-(2,4-difluoro-phenoxy)-1H-pyrazolo[3,4-d]pyrimidin-4-yloxy]-propane-1,2-diol;

{3-[3-(2-Chloro-phenyl)-6-(2,4-difluoro-phenoxy)-1H-pyrazolo[3,4-d]pyrimidin-4-yloxy]-propyl}-dimethyl-amine;

1-[3-(2-Chloro-phenyl)-6-(2,4-difluoro-phenoxy)-1H-pyrazolo[3,4-d]pyrimidin-4-ylamino]-propan-2-one;

3-(2-Chloro-phenyl)-6-(2,4-difluoro-phenoxy)-4-[3-(4-methyl-piperazin-1-yl)propoxy]-1H-pyrazolo[3,4-d]pyrimidine;

3-(2-Chloro-phenyl)-6-(2,4-difluoro-phenoxy)-4-(3-morpholin-4-yl-propoxy)-1H-pyrazolo[3,4-d]pyrimidine;

3-(2-Chloro-phenyl)-6-(2,4-difluoro-phenoxy)-4-[2-(2-methyl-imidazol-1-yl)-ethoxy]-1H-pyrazolo[3,4-d]pyrimidine;

1-{2-[3-(2-Chloro-phenyl)-6-(2,4-difluoro-phenoxy)-1H-pyrazolo[3,4-d]pyrimidin-4-ylamino]-ethyl}-3-methyl-imidazolidin-2-one;

[3-(2-Chloro-phenyl)-6-(2,4-difluoro-phenoxy)-1H-pyrazolo[3,4-d]pyrimidin-4-yl]-(3-methanesulfonyl-propyl)-amine;

3-(2-Chloro-phenyl)-6-(2,4-difluoro-phenoxy)-4-(3-methanesulfonyl-propoxy)-1H-pyrazolo[3,4-d]pyrimidine;

4-{2-[3-(2-Chloro-phenyl)-6-(2,4-difluoro-phenoxy)-1H-pyrazolo[3,4-d]pyrimidin-4-ylamino]-ethyl}-2,4-dihydro-[1,2,4]triazol-3-one;

C-[3-(2-Chloro-phenyl)-6-(2,4-difluoro-phenoxy)-1H-pyrazolo[3,4-d]pyrimidin-4-yl]-N,N-dimethyl-methanesulfonamide;

1-[3-Cyclopentyl-6-(2,4-difluoro-phenoxy)-1H-pyrazolo[3,4-d]pyrimidin-4-ylamino]-propan-2-ol;

1-[6-(2,4-Difluoro-phenoxy)-3-iodo-1H-pyrazolo[3,4-d]pyrimidin-4-ylamino]-propan-2-ol;

1-[3-tert-Butyl-6-(2,4-difluoro-phenoxy)-1H-pyrazolo[3,4-d]pyrimidin-4-ylamino]-propan-2-ol; and 1-[3-Cyclopropyl-6-(2,4-difluoro-phenoxy-1H-pyrazolo[3,4-d]pyrimidin-4-ylamino]-propan-2-ol.

16. A compound of formula V:

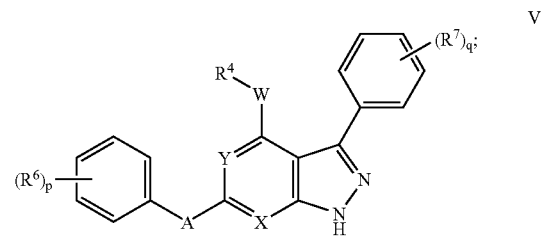

or a pharmaceutically acceptable salt thereof;
wherein:
$R^4$ is hydrogen, alkyl, heteroalkyl, heterocyclyl, hydroxycycloalkyl, aryl, heteroaryl, aralkyl, heteroaralkyl, —C(=O)—$R^b$, or —SO$_2$—$R^b$;
wherein
$R^b$ is alkyl, heteroalkyl, aryl, aralkyl, heteroaryl, or heterocyclyl;

X and Y are nitrogen;

W is O, S(O)$_m$, CH$_2$ or NR$^f$,
wherein
m is from 0 to 2, and
$R^f$ is hydrogen, alkyl, heteroalkyl, heterocyclyl, hydroxycycloalkyl, —C(=O)—$R^g$ or —SO$_2$—$R^g$,
wherein
$R^g$ is alkyl, aryl, aralkyl, beleroaryl, heteroalkyl or heterocyclyl;

A is O or S;
each of p and q is independently from 0 to 4;
each $R^6$ is independently halo, alkyl, alkoxy, haloalkyl, or cyano; and
each $R^7$ is independently halo, alkyl, haloalkyl, cyano, heteroalkyl, heterocyclyl, hydroxycycloalkyl or —C(=O)—$R^m$,
wherein
$R^m$ is alkyl, heteroalkyl, aryl, aralkyl, heteroaryl or heterocyclyl.

* * * * *